US011707029B2

(12) United States Patent
Marks et al.

(10) Patent No.: US 11,707,029 B2
(45) Date of Patent: Jul. 25, 2023

(54) OILSEED PLANTS HAVING REDUCED POD SHATTER

(71) Applicants: Regents of the University of Minnesota, Minneapolis, MN (US); The Board of Trustees of Illinois State University, Normal, IL (US)

(72) Inventors: Michael David Marks, Roseville, MN (US); John C. Sedbrook, Bloomington, IL (US); Ratan Chopra, St. Paul, MN (US); Maliheh Esfahanian, Bloomington, IL (US)

(73) Assignees: Regents of the University of Minnesota, Minneapolis, MN (US); The Board of Trustees of Illinois State University, Normal, IL (US)

( * ) Notice: Subject to any disclaimer, the term of this patent is extended or adjusted under 35 U.S.C. 154(b) by 0 days.

(21) Appl. No.: 16/104,478

(22) Filed: Aug. 17, 2018

(65) Prior Publication Data
US 2019/0053458 A1 Feb. 21, 2019

Related U.S. Application Data

(60) Provisional application No. 62/547,684, filed on Aug. 18, 2017.

(51) Int. Cl.
| | |
|---|---|
| *A01H 5/10* | (2018.01) |
| *A01H 6/20* | (2018.01) |
| *C12N 15/82* | (2006.01) |
| *C07K 14/415* | (2006.01) |
| *C12N 9/24* | (2006.01) |

(52) U.S. Cl.
CPC ............ *A01H 6/20* (2018.05); *C07K 14/415* (2013.01); *C12N 9/2402* (2013.01); *C12N 15/8213* (2013.01); *C12N 15/8266* (2013.01); *C12Y 302/01015* (2013.01); *C12N 9/24* (2013.01)

(58) Field of Classification Search
None
See application file for complete search history.

(56) References Cited

U.S. PATENT DOCUMENTS

| | | |
|---|---|---|
| 2008/0160530 A1 | 7/2008 | Li |
| 2015/0143573 A1 | 5/2015 | Denolf et al. |
| 2017/0051299 A1 | 2/2017 | Fabijanski et al. |
| 2019/0053457 A1 | 2/2019 | Marks et al. |
| 2020/0131523 A1 | 4/2020 | Marks et al. |
| 2020/0308596 A1 | 10/2020 | Marks et al. |
| 2020/0370062 A1 | 11/2020 | Marks et al. |

FOREIGN PATENT DOCUMENTS

| | | |
|---|---|---|
| WO | WO 2000/036114 | 6/2000 |
| WO | WO 2006/052912 | 5/2006 |
| WO | WO 2013/112578 | 8/2013 |
| WO | WO 2017/004375 | 1/2017 |
| WO | WO 2017/117633 | 7/2017 |
| WO | WO 2018/140782 | 8/2018 |

OTHER PUBLICATIONS

Van Gelderen et al, Molecular Plant 9: 857-869, Jun. 2016 (Year: 2016).*
Sedbrook et al, Plant Science 227: 122-132, 2014 (Year: 2014).*
Baud et al., "Physiological and developmental regulation of seed oil production," Prog Lipid Res., 49(3):235-49, Jul. 2010.
Belide et al., "Modification of seed oil composition in *Arabidopsis* by artificial microRNA-mediated gene silencing," Frontiers in plant science, 3:168, Jul. 2012.
Bell, "Factors affecting the nutritional value of canola meal: a review," Canadian Journal of Animal Science, 73(4):679-697, Dec. 1993.
Bligh et al., "A rapid method of total lipid extraction and purification," Canadian Journal of Biochemistry and Physiology, 37(8):911-917, Aug. 1959.
Boateng et al., "Producing stable pyrolysis liquids from the oil-seed presscakes of mustard family plants: Pennycress (*Thlaspi arvense* L.) and Camelina (*Camelina sativa*)," Energy & Fuels, 24(12):6624-6632, Nov. 2010.
Calver et al., "Identification of target genes and processes involved in erucic acid accumulation during seed development in the biodiesel feedstock Pennycress (*Thlaspi arvense* L.)," J. Plant Physiol., 208:7-16, Jan. 2017.
Chopra et al., "The adaptable use of *Brassica* NIRS calibration equations to identify pennycress variants to facilitate the rapid domestication of a new winter oilseed crop," Industrial Crops and Products, 128:55-61, Feb. 2019.
Chopra et al., "Transcriptome profiling and validation of gene based single nucleotide polymorphisms (SNPs) in sorghum genotypes with contrasting responses to cold stress," BMC Genomics, 16(1):1040, Dec. 2015.
Chopra et al., "Translational genomics using *Arabidopsis* as a model enables the characterization of pennycress genes through forward and reverse genetics," The Plant Journal, 96(6):1093-1105, Dec. 2018.
Crevillén et al., "Epigenetic reprogramming that prevents transgenerational inheritance of the vernalized state," Nature, 515(7528):587-90, Nov. 2014.
Dorn et al., "D e novo assembly of the pennycress (*Thlaspi arvense*) transcriptome provides tools for the development of a winter cover crop and biodiesel feedstock," The Plant Journal, 75(6):1028-38, Sep. 2013.
Fauser et al., "Both CRISPR/C as-based nucleases and nickases can be used efficiently for genome engineering in *Arabidopsis thaliana*," Plant J., 79(2):348-359, Jul. 2014.
Ferrándiz et al., "Negative regulation of the SHATTERPROOF genes by FRUITFULL during *Arabidopsis* fruit development," Science, 289(5478):436-438, Jul. 2000.

(Continued)

*Primary Examiner* — Elizabeth F McElwain
(74) *Attorney, Agent, or Firm* — Fish & Richardson P.C.

(57) ABSTRACT

This document relates to materials and methods for domesticating oilseed (e.g., pennycress) plants. For example, oilseed plants having reduced seedpod shatter, as well as materials and methods for making and using oilseed plants having reduced seedpod shatter are provided.

4 Claims, 34 Drawing Sheets

Specification includes a Sequence Listing.

(56) References Cited

OTHER PUBLICATIONS

Girin et al., "Brassicaceae INDEHISCENT genes specify valve margin cell fate and repress replum formation," Plant J., 63(2):329-338, Jul. 2010.

Golebiowski et al., "Near infrared reflectance spectroscopy of oil in intact canola seed (Brassica napus L.). II. Association between principal components and oil content," Journal of near Infrared Spectroscopy, 13(5):255-264, Oct. 2005.

Han et al., "Functional characterization of beta-ketoacyl-CoA synthase genes from Brassica napus L," Plant molecular biology, 46(2):229-39, May 2001.

Kim et al., "Toward production of jet fuel functionality in oilseeds: identification of FatB acyl-acyl carrier protein thioesterases and evaluation of combinatorial expression strategies in Camelina seeds," Journal of Experimental Botany, 66(14):4251-4265, May 2015.

Liljegren et al., "SHATTERPROOF MADS-box genes control seed dispersal in Arabidopsis," Nature, 404(6779):766-770, Apr. 2000.

McGinn et al., "Molecular tools enabling pennycress (Thlaspi arvense) as a modelplant and oilseed cash cover crop," Plant Biotechnology Journal, 17(4):776-788, Apr. 2019.

Montero de Espinosa et al., "Plant oils: The perfect renewable resource for polymer science?!" European Polymer Journal, 47(5):837-852, May 2011.

Moser et al., "Composition and physical properties of cress (Lepidium sativum L.) and field pennycress (Thlaspi arvense L.) oils," Industrial Crops and Products, 30(2):199-205, Sep. 2009.

Moser et al., "Production and evaluation of biodiesel from field pennycress (Thlaspi arvense L.) oil," Energy & Fuels, 23(8):4149-4155, Jul. 2009.

Phippen et al., "Soybean seed yield and quality as a response to field pennycress residue," Crop Science, 52(6):2767-2773, Nov. 2012.

Riu et al., "[Detection of erucic acid and glucosinolate in intact rapeseed by near-infrared diffuse reflectance spectroscopy]," Spectroscopy and Spectral Analysis, Dec. 2006, 26(12):2190-2192, (with English abstract).

Roeder et al., "The role of the REPLUMLESS homeodomain protein in patterning the Arabidopsis fruit," Curr. Biol., 13(18):1630-1635, Sep. 2003.

Rosas et al., "One-step, codominant detection of imidazolinone resistance mutations in weedy rice (Oryza sativa L.)," Electron. J. Biotechnol., 17:95-101, Mar. 2014.

Roscoe et al., "Mutations in the fatty acid elongation 1 gene are associated with a loss of β-ketoacyl-CoA synthase activity in low erucic acid rapeseed," FEBS letters, 492(1-2):107-11, Mar. 2001.

Sedbrook et al., "New approaches to facilitate rapid domestication of a wild plant to an oilseed crop: example pennycress (Thlaspi arvense L.)," Plant Sci., 227:122-32, Oct. 2014.

Sedbrook et al., "New approaches to facilitate rapid domestication of a wild plant to an oilseed crop: example pennycress (Thlaspi arvense L.)," Plant Science, 227:122-132, Oct. 2014.

Sidhu et al., "Diode Array Near Infrared Spectrometer Calibrations for Composition Analysis of Single Plant Canola (Brassica napus) Seed," Applied Engineering in Agriculture, 30(1):69-76, Jan. 2014.

Steinert et al., "Highly efficient heritable plant genome engineering using Cas9 orthologues from Streptococcus thermophilus and Staphylococcus aureus," Plant J., 84:1295-305, Dec. 2015.

Warwick et al., "The biology of Canadian weeds. 9. Thlaspi arvense L.(updated)," Canadian Journal of Plant Science, 82(4):803-823, Oct. 2002.

Wu et al., "Zero erucic acid trait of rapeseed (Brassica napus L.) results from a deletion of four base pairs in the fatty acid elongase 1 gene," Theoretical and applied genetics, 116(4):491-9, Feb. 2008.

Xin et al., "Mid-infrared spectral characteristics of lipid molecular structures in Brassica carinata seeds: relationship to oil content, fatty acid and glucosinolate profiles, polyphenols, and condensed tannins," J. Agric. Food Chem., 62(32):7977-7988, Aug. 2014.

Britt, "From stinkweed to oilseed," Nat. Food, 1:24-25, Jan. 2020.

Chopra et al., "Identification and stacking of crucial traits required for the domestication of pennycress," Nat. Food, 1:84-91, Jan. 2020.

Claver et al., "Identification of target genes and processes involved in erucic acid accumulation during seed development in the biodiesel feedstock Pennycress (Thlaspi arvense L.)," Journal of plant physiology, 208:7-16, Jan. 2017.

Downey and Craig, "Genetic control of fatty acid biosynthesis in rapeseed (Brassica napus L.)," Journal of the American Oil Chemists' Society, Jul;41(7):475-8, Jul. 1964.

Fourmann et al., "The two genes homologous to Arabidopsis FAE1 co-segregate with the two loci governing erucic acid content in Brassica napus," Theor. Appl. Genet., 96(6-7):852-8, May 1998.

James et al., "Directed Tagging of the Arabidopsis Fatty Acid Elongation1 (FAE1) Gene with the Maize Transposon Activator," The Plant Cell, 7:309-319, Mar. 1995.

Javidfar and Cheng, "Single locus, multiallelic inheritance of erucic acid content and linkage mapping of FAE1 gene in yellow mustard," Crop Science, 53(3):825-32, May 2013.

Xie et al., "RNA-Guided Genome Editing in Plants Using a CRISPR-Cas System," Molecular Plant, Nov. 2013, 6(6):1975-1983.

Katavic et al., "Alteration of Seed Fatty Acid Composition by an Ethyl Methanesulfonate-induced Mutation in Arabidopsis thaliana Affecting Diacylglycerol Acyltransferase Activity," Plant Physiology, May 1995, 108(1):399-409.

Lu et al., "Arabidopsis Mutants Deficient in Diacylglycerol Acyltransferase Display Increased Sensitivity to Abscisic Acid, Sugars, and Osmotic Stress During Germination and Seedling Development," Plant Physiology, Jul. 2002, 129(3):1352-1358.

Lu et al., "Expression pattern of diacylglycerol acyltransferase-1, an enzyme involved in triacylglycerol biosynthesis, in Arabidopsis thaliana," Plant Mol. Biology, May 2003, 52(1):31-41.

Routaboul et al., "The TAG1 locus of Arabidopsis encodes for a diacylglycerol acyltransferase," Plant Physiol Biochemistry, Nov. 1999, 37(11):831-840.

Sanyal et al., "Stearic sunflower oil as a sustainable and healthy alternative to palm oil. A review," Agron. Sustain. Development, May 17, 2017, 37:18, 11 pages.

Vogel et al., "Expression of the Arabidopsis WRINKLED 1 transcription factor leads to higher accumulation of palmitate in soybean seed," Plant Biotechnol. Journal, Jan. 17, 2019, 17(7):1369-1379.

Zarhloul et al., "Breeding high-stearic oilseed rape (Brassica napus) with high- and low-erucic background using optimised promoter-gene constructs," Mol. Breeding, Sep. 2006, 18(3):241-251.

Zou et al., "The Arabidopsis thaliana TAG1 mutant has a mutation in a diacylglycerol acyltransferase gene.," The Plant Journal, Sep. 1999, 19(6):645-653.

Bal et al., "The Biochemistry of Headgroup Exchange During Triacylglycerol Synthesis in Canola," The Plant Journal, 103(1):83-94, Jan. 2020.

Kano-Murakami et al., "A rice homeotic gene, OSH1, causes unusual phenotypes in transgenic tobacco," FEBS letters, 334(3):365-8, Nov. 1993.

Yu et al., "Modulation of brassinosteroid-regulated gene expression by Jumonji domain-containing proteins ELF6 and REF6 in Arabidopsis," Proceedings of the National Academy of Sciences, 105(21):7618-23, May 2008.

Ballester et al., "Shattering fruits: variations on a dehiscent theme," Curr. Opin. Plant Biology, Feb. 2017, 35:68-75.

Bennett et al., "Morphogenesis in pinoid mutants of Arabidopsis thaliana," Plant Journal, Oct. 1995, 8(4):505-520.

Blacklock et al., "Substrate specificity of Arabidopsis 3-ketoacyl-CoA synthases," Biochem. Biohpys. Res. Communications, Jun. 5, 2006, 346(2):583-590.

Joubes et al., "The VLCFA elongase gene family in Arabidopsis thaliana: phylogenetic analysis, 3D modelling and expression profiling," Plant Mol. Biology, May 9, 2008, 67(5):547-566.

Millar et al., "Very-long-chain fatty acid biosynthesis is controlled through the expression and specificity of the condensing enzyme," Plant Journal, Jul. 1997, 12(1):121-131.

Morineau et al., "Dual Fatty Acid Elongase Complex Interactions in Arabidopsis," PLoS One, Sep. 1, 2016, 11(9):e0160631, 20 pages.

(56) References Cited

OTHER PUBLICATIONS

Wang et al., "A functional genomics resource for *Brassica napus*: development of an EMS mutagenized population and discovery of FAE1 point mutations by TILLING," New Phytologist, Dec. 2008, 180(4):751-765.

Batsale et al., "Biosynthesis and Functions of Very-Long-Chain Fatty Acids in the Responses of Plants to Abiotic and Biotic Stresses," Cells, May 21, 2021, 10:1284, 26 pages.

Claver et al., "Functional analysis of β-ketoacyl-CoA synthase from biofuel feedstock Thlaspi arvense reveals differences in the triacylglycerol biosynthetic pathway among Brassicaceae," Plant Mol. Biology, 104(3):283-296, Aug. 1, 2020.

Dorn et al., "A draft genome of field pennycress (*Thlaspi arvense*) provides tools for the domestication of a new winter biofuel crop," DNA Research, Apr. 2015, 22(2):121-131.

ENA Accession No. PRJEB46635, "Chromosome-level Thlaspi arvense genome provides new tools for translational research and for a newly domesticated cash cover crop of the cooler climates," dated Aug. 2, 2021, 2 pages.

GenBank Accession No. AAC49186.1, "beta-ketoacyl-CoA synthase [*Simmondsia chinensis*]," dated Oct. 31, 1995, 2 pages.

GenBank Accession No. AZNP01000000.1. "Thlaspi arvense cultivar MN106, whole genome shotgun sequencing project," dated Mar. 19, 2015, 1 page.

GenBank Accession No. NP_195178.1, "3-ketoacyl-CoA synthase 18 [*Arabidopsis thaliana*]," dated Jan. 22, 2014, 2 pages.

Geng et al., "Genomic analysis of field pennycress (*Thlaspi arvense*) provides insights into mechanisms of adaptation to high elevation," BMC Biology, Jul. 22, 2021, 19:143, 14 pages.

Gigolashvili et al., "The R2R3-MYB transcription factor HAG1/MYB28 is a regulator of methionine-derived glucosinolate biosynthesis in *Arabidopsis thaliana*," Plant Journal, 51(2):247-261, Jul. 2007.

Haslam et al., "Extending the story of very-long-chain fatty acid elongation," Plant Science, 210:93-107, Sep. 2013.

Kafri et al., "The regulatory utilization of genetic redundancy through responsive backup circuits," Proc. Nat. Acad. Sci. USA, 103(31):11653-11658, Aug. 2006.

Lassner et al., "A jojoba beta-Ketoacyl-CoA synthase cDNA complements the canola fatty acid elongation mutation in transgenic plants," Plant Cell, 8(2):281-292, Feb. 1996.

Nunn et al., "Chromosome-level Thlaspi arvense genome provides new tools for translational research and for a newly domesticated cash cover crop of the cooler climates," bioRxiv, Aug. 1, 2021, 48 pages.

Shen et al., "Resistance gene candidates identified by PCR with degenerate oligonucleotide primers map to clusters of resistance genes in lettuce," Mol. Plant Microbe Interactions, 11(8):815-823, Aug. 1998.

Tresch et al., "Inhibition of saturated very-long-chain fatty acid biosynthesis by mefluidide and perfluidone, selective inhibitors of 3-ketoacyl-CoA synthases," Phytochemistry, Apr. 2012, 76:162-171.

Yang et al., "Comprehensive analysis of KCS gene family in Citrinae reveals the involvement of CsKCS2 and CsKCS11 in fruit cuticular wax synthesis at ripening," Plant Science, Sep. 2021, 310:110972, 11 pages.

Zeng et al. (Plant cell, 26:2648-2659, Jun. 2014).

Blande et al. (GenBank Sequence Accession No. GEVK01020461.1, Published Nov. 4, 2016).

GenBank Accession No. KT223025.1, "Thlaspi arvense cultivar French 3-ketoacyl-CoA synthase (FAE1) mRNA, complete cds," Nov. 29, 2015, 2 pages.

\* cited by examiner

WT pennycress SPT
SEQ ID NO:1

ATGATATCACAAGAGAAGAGAGAGAAGAGAAGAGAGTGATGGGAGATAAGAAATTGATTTCATCG
TCTTCTTCTATTGCCTCGGTTTACGATACTCGTAATAATAACAATCATCATCACCCACCGTCTTCC
TCCGACGAGATTTCTCAGTTTCTCCGGCATATTTTCGACCGTTCTTCTCCTCTCCCTTCTTACTAT
TCTCCGGCGACGATGACGACGGCGCCAATCGGAGTGCACGGCGACCCACATGCAGACAACCCCCGG
AGCTTCGTTTCTCATCCGCCGTCTGACTCTGCGCTCCCGTCGAAGCGCCCCGCTGATTACTCTGAG
GTTTTAATAGGCTCCGCCGTTGGATCAGCCTCCGCCGTTGGATCAGGCTCAGCCCCGTGTTTTGGT
TTCTCCGGAGGTAATAACATTGCCCAAGGAAACAGCTCAGGGACTCGAGTTTCGTCTTCTTCCGTT
GGAGCTAGCGGGAATGACACCGACGAGTACGATTGCGAAAGCGAGgtctctctctctatgtgca
tgttctaaaagttcccatctttgtctgtttcctgagaaaatgttatactgtgactttctctaacgg
atctgtactttcttttctcaccattcaagtgagcaaattaaatttgccttttttttctgtgtgtgt
gttttttagtgaagtttgtgaatgttaataatgcacacagagtgtttgttgatttgcttgaatga
aatcagGAAGGAGTAGAAGCTGTGGTTGATGATGATCTTCCCTCAAAGTCTGGTCCTTCTCGTAGC
TCATCAAAGCGATGCAGAGCTGCTGAAGTTCATAATTTGTCTGAAAAGgttttttatttgctcctt
gtttttgttttctctcccaaaatcacattccttttttactcagagattgatgtgatcttgttctgac
agAGGAGGAGAAGTAGGATCAACGAAAAAATGAAAGCTTTACAAAGTCTCATCCCAAATTCAAACA
AGgtaaaaatacatacaaatgctgaatcattctctcatttgtctcttgttattgtgtctgattata
taatgtccattgcaatgcgttgatgattggtgggaagACGGATAAGGCTTCAATGCTTGATGAAGC
TATAGAGTATCTGAAACAGCTTCAGCTTCAAGTCCAGgtcacaaaatatccattctcaaaaagata
tgatacattcacttttcccgaatcaatcttatgaacagattactctgtgttttgcagATGTTGACA
ATGAGGAATGGAATAAACTTGCATCCTCTGTGCTTACCTGGAACTACATTACACCCATTGCAACTC
TCTCAGGTTCGAGGGATGCCTCAAGAAGCAACCAATGATCATCTGCTTAATCACACCAACCAATTC
GGTTCGACCTCTAACGCACCTGAGATGATCAACACCGTGCCTTCCTCATACTCGTTGGAACCTTCC
GTCCGCAGTCACTTTGGACCTTTCCCTCTCCTTACTTCACACGCGgtgcgtggtttcataacacat
tttcaatctataaacctagattcttgaaagctagtgttcttactagaaatttattgttttttcgt
aaagGAGATGAGTCGAGAAGGTGGACTAACTCATCACAGGTTGAGCATTGGTCATTCCAACACAAA
CTTAACCGgtaaagtcttcctgatttctgaattctcgtgaagaagttttttaagacattgacaatgt
taaaaatgttgcgacgtttgggtatttgcagGGGCACAAGCTGTGTTTAATGGACAAGAACAACCT
GACATAAAGATCGACTTACTTGA

FIG. 2A

WT pennycress SPT
SEQ ID NO:2

MISQREEREEKRVMGDKKLISSSSSIASVYDTRNNNNHHHPPSSSDEISQFLRHIFDRSSPLPSYY
SPATMTTAAIGVHGDPHADNPRSFVSHPPSDSALPSKRPADYSEVLIGSAVGSASAVGSGSAPCFG
FSGGNNIAQGNSSGTRVSSSSVGASGNDTDEYDCESEEGVEAVVDDDLPSKSGPSRSSSKRCRAAE
VHNLSEKRRRSRINEKMKALQSLIPNSNKTDKASMLDEAIEYLKQLQLQVQMLTMRNGINLHPLCL
PGTTLHPLQLSQVRGMPQEATNDHLLNHTNQFGSTSNAPEMINTVPSSYSLEPSVRSHFGPFPLLT
SHAEMSREGGLTHHRLSIGHSNTNLTGAQAVFNGQEQPDIKDRLT

FIG. 2B modified pennycress SPT (spt-1)
SEQ ID NO:3

ATGATATCACAAAGAGAAGAGAGAGAAGAGAAGAGAGTGATGGGAGATAAGAAATTGATTTCATCG
TCTTCTTCTATTGCCTCGGTTTACGATACTCGTAATAATAACAATCATCATCACCCACCGTCTTCC
TCCGACGAGATTTCTCAGTTTCTC*T*GGCATATTTTCGACCGTTCTTCTCCTCTCCCTTCTTACTAT
TCTCCGGCGACGATGACGACGGCGGCAATCGGAGTGCACGGCGACCCACATGCAGACAACCCCCGG
AGCTTCGTTTCTCATCCGCCGTCTGACTCTGCGCTCCCGTCGAAGCGCCCCGCTGATTACTCTGAG
GTTTTAATAGGCTCCGCCGTTGGATCAGCCTCCGCCGTTGGATCAGGCTCAGCCCCGTGTTTTGGT
TTCTCCGGAGGTAATAACATTGCCCAAGGAAACAGCTCAGGGACTCGAGTTTCGTCTTCTTCCGTT
GGAGCTAGCGGGAATGACACCGACGAGTACGATTGCGAAAGCGAGgtctctctctctatgtgca
tgttctaaaagttcccatctttgtctgtttcctgagaaaatgttatactgtgactttctctaacgg
atctgtactttcttttctcaccattcaagtgagcaaattaaatttgcctttttttctgtgtgtgt
gttttttagtgaagtttgtgaatgttaataatgcacacagagtgtttgttgatttgcttgaatga
aatcagGAAGGAGTAGAAGCTGTGGTTGATGATGATCTTCCCTCAAAGTCTGGTCCTTCTCGTAGC
TCATCAAAGCGATGCAGAGCTGCTGAAGTTCATAATTTGTCTGAAAAGgttttttatttgctcctt
gttttgttttctctcccaaaatcacattcctttttactcagagattgatgtgatcttgttctgac
agAGGAGGAGAAGTAGGATCAACGAAAAAATGAAAGCTTTACAAAGTCTCATCCCAAATTCAAACA
AGgtaaaaatacatacaaatgctgaatcattctctcatttgtctcttgttattgtgtctgattata
taatgtccattgcaatgcgttgatgattggtgggaagACGGATAAGGCTTCAATGCTTGATGAAGC
TATAGAGTATCTGAAACAGCTTCAGCTTCAAGTCCAGgtcacaaaatatccattctcaaaaagata
tgatacattcacttttcccgaatcaatcttatgaacagattactctgtgttttgcagATGTTGACA
ATGAGGAATGGAATAAACTTGCATCCTCTGTGCTTACCTGGAACTACATTACACCCATTGCAACTC
TCTCAGGTTCGAGGGATGCCTCAAGAAGCAACCAATGATCATCTGCTTAATCACACCAACCAATTC
GGTTCGACCTCTAACGCACCTGAGATGATCAACACCGTGCCTTCCTCATACTCGTTGGAACCTTCC
GTCCGCAGTCACTTTGGACCTTTCCCTCTCCTTACTTCACACGCGgtgcgtggtttcataacacat
tttcaatctataaaccctagattcttgaaagctagtgttcttactagaaatttattgttttttcgt
aaagGAGATGAGTCGAGAAGGTGGACTAACTCATCACAGGTTGAGCATTGGTCATTCCAACACAAA
CTTAACCGgtaaagtcttcctgatttctgaattctcgtgaagaagttttttaagacattgacaatgt
taaaaatgttgcgacgtttgggtatttgcagGGGCACAAGCTGTGTTTAATGGACAAGAACAACCT
GACATAAAAGATCGACTTACTTGA

FIG. 2C modified pennycress SPT (spt-1)
SEQ ID NO:4

MISQREEREEKRVMGDKKLISSSSSIASVYDTRNNNNHHHPPSSSDEISQFL*W*HIFDRSSPLPSYY
SPATMTTAAIGVHGDPHADNPRSFVSHPPSDSALPSKRPADYSEVLIGSAVGSASAVGSGSAPCFG
FSGGNNIAQGNSSGTRVSSSSVGASGNDTDEYDCESEEGVEAVVDDDLPSKSGPSRSSSKRCRAAE
VHNLSEKRRRSRINEKMKALQSLIPNSNKTDKASMLDEAIEYLKQLQLQVQMLTMRNGINLHPLCL
PGTTLHPLQLSQVRGMPQEATNDHLLNHTNQFGSTSNAPEMINTVPSSYSLEPSVRSHFGPFPLLT
SHAEMSREGGLTHHRLSIGHSNTNLTGAQAVFNGQEQPDIKDRLT

FIG. 2D

WT pennycress ALC
SEQ ID NO:5

ATGGGCAATCCCGACGACGGTGATCGTCTTCCTCCTCCATCTTCTTCCGACGAACTCTCGAGC
GTTCTCCGGCAGATTCTGTCCCGTGCCCCGATAACTCAACCTTCGTCGTCACCACCGAGGAGA
GTCGTTTCCTCCGCTGAAATGTTCGACCGGACCTTCCCTTTCGTTCCCGGCGGAGCGGTTTCT
TCCGCCGCCTATAAAGTCGCTGGCGAAGACAAATGTGCTTTCGAAAACAAGgtaagctaacat
ttttaagctgtcgagaaacttcactcgcttcgtttatgaattaagctaacatttctttgtaat
ggtaacaacactaaagAGAAATGGAGGAGCTAAACATCGAAATTCGTTGAAGAGAAACAATGA
TGCACAATTCCACAACTTGTCTGAAAAGgttctgtcttttaatcttctaaagattctcgattt
gagaaagaaaagcaattgtgattttaatttatagaatctgaaattatttgcagAGGAGGAGGA
GCAAGATCAACGAGAAAATGAAAGCTTTGCAGAAACTGATACCCAATTCCAACAAGtaaatg
aaaaaagttggaatctttctacttctgaatacaatcgtgagaaacaccgttatgcttttgttt
gtttgtttgtagACTGATAAAGCCTCAATGCTCGATGAAGCTATAGAGTATATGAAGCAGCTT
CAACTTCAAGTGCAGgttttggctttactaagatcatatacaaccaaattataattttttgt
aaaactcagcgcttatttgatcatacaatggataatgcagACTTTAGCAGTCATGAATGGTTT
AGGCCTAA*ACCCAA*TGCGATTACCACCAACACAGACAAGGATCAATGAGGCCTTACACATGCA
GACTCTGCTTGGCGGTTCTCACTCGCTTGTTCACCGTGAACCACCCGAAGCAAGTCAAGAAAT
GTGCTTTTCCGCTGCGGCTCGTCTTTAA

FIG. 3A

WT pennycress ALC
SEQ ID NO:6

MGNPDDGDRLPPPSSSDELSSVLRQILSRAPITQPSSSPPRRVVSSAEMFDRTFPFVPGGAVS
SAAYKVAGEDKCAFENKRNGGAKHRNSLKRNNDAQFHNLSEKRRRSKINEKMKALQKLIPNSN
KTDKASMLDEAIEYMKQLQLQVQTLAVMNGLGLNPMRLPPTQTRINEALHMQTLLGGSHSLVH
REPPEASQEMCFSAAARL

FIG. 3B modified pennycress ALC (alc-1)
SEQ ID NO:7

ATGGGCAATCCCGACGACGGTGATCGTCTTCCTCCTCCATCTTCTTCCGACGAACTCTCGAGC
GTTCTCCGGCAGATTCTGTCCCGTGCCCCGATAACTCAACCTTCGTCGTCACCACCGAGGAGA
GTCGTTTCCTCCGCTGAAATGTTCGACCGGACCTTCCCTTTCGTTCCCGGCGGAGCGGTTTCT
TCCGCCGCCTATAAAGTCGCTGGCGAAGACAAATGTGCTTTCGAAAACAAGgtaagctaacat
ttttaagctgtcgagaaacttcactcgcttcgtttatgaattaagctaacatttctttgtaat
ggtaacaacactaaagAGAAATGGAGGAGCTAAACATCGAAATTCGTTGAAGAGAAACAATGA
TGCACAATTCCACAACTTGTCTGAAAAGgttctgtcttttaatcttctaaagattctcgattt
gagaaagaaaagcaattgtgattttaatttatagaatctgaaattatttgcagAGGAGGAGGA
GCAAGATCAACGAGAAAATGAAAGCTTTGCAGAAACTGATACCCAATTCCAACAAGgtaaatg
aaaaaagttggaatctttctacttctgaatacaatcgtgagaaacaccgttatgcttttgttt
gtttgtttgtagACTGATAAAGCCTCAATGCTCGATGAAGCTATAGAGTATATGAAGCAGCTT
CAACTTCAAGTGCAGgttttttggctttactaagatcatatacaaccaaattataattttttgt
aaaactcagcgcttatttgatcatacaatggataatgcagACTTTAGCAGTCATGAATGGTTT
AGGCCTAAacccaatgcgTCTCATTACCACCAACACAGACAAGGATCAATGAGGCCTTACACA
TGCAGACTCTGCTTGGCGGTTCTCACTCGCTTGTTCACCGTGAACCACCCGAAGCAAGTCAAG
AAATGTGCTTTTCCGCTGCGGCTCGTCTTTAA

FIG. 3C modified pennycress ALC (alc-1)
SEQ ID NO:8

MGNPDDGDRLPPPSSSDELSSVLRQILSRAPITQPSSSPPRRVVSSAEMFDRTFPFVPGGAVS
SAAYKVAGEDKCAFENKRNGGAKHRNSLKRNNDAQFHNLSEKRRRSKINEKMKALQKLIPNSN
KTDKASMLDEAIEYMKQLQLQVQTLAVMNGLGL*IS*LPPTQTRINEALHMQTLLGGSHSLVHRE
PPEASQEMCFSAAARL

FIG. 3D

WT pennycress IND
SEQ ID NO:9

ATGAATTGGAACAAACCTAATGATCTCATCACACAAGAATACCCCTTTCTCCACGATCCTCAT
CTCATGATAGATCCACCTCCCGAAACCCTAAGTCATTTCCAGCCCCGCCGACACTTTTCTCC
GGTCACGGAGGGGAGGAAGAAGAAGAAGAAGATAATGAAGAGGAAGAGATGGATGCGATGAAG
GAGATGCAGTACACGATCGCTGCCATGCAGCCCGTGGACATCGATCCAGCCACCGTTCTAAA
CCGAACCGCCGTAACGTAAGGGTAAGCGACGACACTCAGACGGTGGTGGCTCGTCGGCGTCGA
GAAAAGATAAGCGAGAAGATCCGAATATTGAAGAGGATGGTGCCAGGCGGTGCGAAGATGGAC
ACAGCCTCCATGCTCGACGAAGCCATCCGTTATACCAAGTTCTTGAAACGGCAGGTGAAGCTT
CTTCAGCCTCACTCTCAGCTTGGAGCTCCTATGTCTGACCCCTCTTGCCTTTGTTATTACCAC
AACTCCCAAACCTAA

WT pennycress IND
SEQ ID NO:69

ATGTTTGGCTCAAAAGCAGATCCACCCATAACCCCAATAGTCATGATGGAGCCTCAACCTCAT
CATCTCCTCATGAATTGGAACAAACCTAATGATCTCATCACACAAGAATACCCCTTTCTCCAC
GATCCTCATCTCATGATAGATCCACCTCCCGAAACCCTAAGTCATTTCCAGCCCCGCCGACA
CTTTTCTCCGGTCACGGAGGGGAGGAAGAAGAAGAAGAAGATAATGAAGAGGAAGAGATGGAT
GCGATGAAGGAGATGCAGTACACGATCGCTGCCATGCAGCCCGTGGACATCGATCCAGCCACC
GTTCCTAAACCGAACCGCCGTAACGTAAGGGTAAGCGACGACACTCAGACGGTGGTGGCTCGT
CGGCGTCGAGAAAAGATAAGCGAGAAGATCCGAATATTGAAGAGGATGGTGCCAGGCGGTGCG
AAGATGGACACAGCCTCCATGCTCGACGAAGCCATCCGTTATACCAAGTTCTTGAAACGGCAG
GTGAAGCTTCTTCAGCCTCACTCTCAGCTTGGAGCTCCTATGTCTGACCCCTCTTGCCTTTGT
TATTACCACAACTCCCAAACCTAAATGTTTGGCTCAAAAGCAGATCCACCCATAACCCCAATA
GTCATGATGGAGCCTCAACCTCATCATCTCCTCATGAATTGGAACAAACCTAATGATCTCATC
ACACAAGAATACCCCTTTCTCCACGATCCTCATCTCATGATAGATCCACCTCCCGAAACCCTA
AGTCATTTCCAGCCCCGCCGACACTTTTCTCCGGTCACGGAGGGGAGGAAGAAGAAGAAGAA
GATAATGAAGAGGAAGAGATGGATGCGATGAAGGAGATGCAGTACACGATCGCTGCCATGCAG
CCCGTGGACATCGATCCAGCCACCGTTCCTAAACCGAACCGCCGTAACGTAAGGGTAAGCGAC
GACACTCAGACGGTGGTGGCTCGTCGGCGTCGAGAAAAGATAAGCGAGAAGATCCGAATATTG
AAGAGGATGGTGCCAGGCGGTGCGAAGATGGACACAGCCTCCATGCTCGACGAAGCCATCCGT
TATACCAAGTTCTTGAAACGGCAGGTGAAGCTTCTTCAGCCTCACTCTCAGCTTGGAGCTCCT
ATGTCTGACCCCTCTTGCCTTTGTTATTACCACAACTCCCAAACCTAA

FIG. 4A

WT pennycress IND
SEQ ID NO:10

MNWNKPNDLITQEYPFLHDPHLMIDPPPETLSHFQPPPTLFSGHGGEEEEEEDNEEEEMDAMK
EMQYTIAAMQPVDIDPATVPKPNRRNVRVSDDTQTVVARRRREKISEKIRILKRMVPGGAKMD
TASMLDEAIRYTKFLKRQVKLLQPHSQLGAPMSDPSCLCYYHNSQT

WT pennycress IND
SEQ ID NO:70

MFGSKADPPITPIVMMEPQPHHLLMNWNKPNDLITQEYPFLHDPHLMIDPPPETLSHFQPPPT
LFSGHGGEEEEEEDNEEEEMDAMKEMQYTIAAMQPVDIDPATVPKPNRRNVRVSDDTQTVVAR
RRREKISEKIRILKRMVPGGAKMDTASMLDEAIRYTKFLKRQVKLLQPHSQLGAPMSDPSCLC
YYHNSQT

FIG. 4B modified pennycress IND (ind-1)
SEQ ID NO:11

ATGAATTGGAACAAACCTAATGATCTCATCACACAAGAATACCCCTTTCTCCACGATCCTCAT
CTCATGATAGATCCACCTCCCGAAACCCTAAGTCATTTCCAGCCCCCGCCGACACTTTTCTCC
GGTCACGGAGGGGAGGAAGAAGAAGAAGAAGATAATGAAGAGGAAGAGATGGATGCGATGAAG
GAGATGCAGTACACGATCGCTGCCATGCAGCCCGTGGACATCGATCCAGCCACCGTT*T*CTAAA
CCGAACCGCCGTAACGTAAGGGTAAGCGACGACACTCAGACGGTGGTGGCTCGTCGGCGTCGA
GAAAAGATAAGCGAGAAGATCCGAATATTGAAGAGGATGGTGCCAGGCGGTGCGAAGATGGAC
ACAGCCTCCATGCTCGACGAAGCCATCCGTTATACCAAGTTCTTGAAACGGCAGGTGAAGCTT
CTTCAGCCTCACTCTCAGCTTGGAGCTCCTATGTCTGACCCTCTTGCCTTTGTTATTACCAC
AACTCCCAAACCTAA

FIG. 4C modified pennycress IND (ind-1)
SEQ ID NO:12

MNWNKPNDLITQEYPFLHDPHLMIDPPPETLSHFQPPPTLFSGHGGEEEEEEDNEEEEMDAMK
EMQYTIAAMQPVDIDPATV*S*KPNRRNVRVSDDTQTVVARRRREKISEKIRILKRMVPGGAKMD
TASMLDEAIRYTKFLKRQVKLLQPHSQLGAPMSDPSCLCYYHNSQT

FIG. 4D modified pennycress IND (ind-2)
SEQ ID NO:13

ATGAATTGGAACAAACCTAATGATCTCATCACACAAGAATACCCCTTTCTCCACGATCCTCAT
CTCATGATAGATCCACCTCCCGAAACCCTAAGTCATTTCCAGCCCCGCCGACACTTTTCTCC
GGTCACGGAGGGGAGGAAGAAGAAGAAGAAGATAATGAAGAGGAAGAGATGGATGCGATGAAG
GAGATGCAGTACACGATCGCTGCCATGCAGCCCGTGGACATCGATCCAGCCACCGTTCCTAAA
CCGAACCACCGTAACGTAAGGGTAAGCGACGACACTCAGACGGTGGTGGCTCGTCGGCGTCGA
GAAAAGATAAGCGAGAAGATCCGAATATTGAAGAGGATGGTGCCAGGCGGTGCGAAGATGGAC
ACAGCCTCCATGCTCGACGAAGCCATCCGTTATACCAAGTTCTTGAAACGGCAGGTGAAGCTT
CTTCAGCCTCACTCTCAGCTTGGAGCTCCTATGTCTGACCCCTCTTGCCTTTGTTATTACCAC
AACTCCCAAACCTAA

FIG. 4E modified pennycress IND (ind-2)
SEQ ID NO:14

MNWNKPNDLITQEYPFLHDPHLMIDPPPETLSHFQPPPTLFSGHGGEEEEEEDNEEEEMDAMK
EMQYTIAAMQPVDIDPATVPKPNHRNVRVSDDTQTVVARRRREKISEKIRILKRMVPGGAKMD
TASMLDEAIRYTKFLKRQVKLLQPHSQLGAPMSDPSCLCYYHNSQT

FIG. 4F modified pennycress IND (ind-3; also named rps1-1)
SEQ ID NO:15

ATGAATTGGAACAAACCTAATGATCTCATCACACAAGAATACCCCTTTCTCCACGATCCTCAT
CTCATGATAGATCCACCTCCCGAAACCCTAAGTCATTTCCAGCCCCCGCCGACACTTTTCTCC
GGTCACGGAGGGGAGGAAGAAGAAGAAGAAGATAATGAAGAGGAAGAGATGGATGCGATGAAG
GAGATGCAGTACACGATCGCTGCCATGCAGCCCGTGGACATCGATCCAGCCACCGTTCCTAAA
CCGAACCGCCGTAACGTAAGGGTAAGCGACGACACTCAGACGGTGGTGACTCGTCGGCGTCGA
GAAAAGATAAGCGAGAAGATCCGAATATTGAAGAGGATGGTGCCAGGCGGTGCGAAGATGGAC
ACAGCCTCCATGCTCGACGAAGCCATCCGTTATACCAAGTTCTTGAAACGGCAGGTGAAGCTT
CTTCAGCCTCACTCTCAGCTTGGAGCTCCTATGTCTGACCCCTCTTGCCTTTGTTATTACCAC
AACTCCCAAACCTAA

FIG. 4G modified pennycress IND (ind-3; also named rps1-1)
SEQ ID NO:16

MNWNKPNDLITQEYPFLHDPHLMIDPPPETLSHFQPPPTLFSGHGGEEEEEEDNEEEEMDAMK
EMQYTIAAMQPVDIDPATVPKPNRRNVRVSDDTQTVVTRRRREKISEKIRILKRMVPGGAKMD
TASMLDEAIRYTKFLKRQVKLLQPHSQLGAPMSDPSCLCYYHNSQT

FIG. 4H

WT pennycress SHP1
SEQ ID NO:17

ATGGAAGAGGGTGGGAGTAGTCACGACGCAGAGAGTAGCAAGAAGATAGGGAGAGGGAAGATA
GAGATAAAGAGGATAGAGAACACAACGAATCGTCAAGTAACTTTCTGCAAACGACGCAATGGT
CTTCTCAAGAAAGCTTATGAGCTCTCTGTCTTGTGTGATGCCGAAGTTGCCCTCGTTATCTTC
TCCACTCGTGGCCGTCTCTATGAGTATGCCAACAACAGTGTGAAGGGTACAATTGAAAGGTAC
AAGAAAGCTTGTTCAGATGCCGTCAATCCCCCTCCGTCACCGAAGCTAATACTCAGTACTAT
CAGCAAGAAGCCTCTAAGCTTCGGAGGCAGATTCGAGACATTCAGAACTCAAACAGGCATATT
GTTGGGGAATCACTTGGTTCCTTGAACTTCAAGGAACTCAAAAACCTCGAAGGACGCCTTGAA
AAAGGAATTAGCCGCGTCCGATCCAAGAAGAATGAGTTGTTAGTGGCAGAGATTGAGTATATG
CAGAAGAGGGAAATGGATTTGCAACACGATAACATGTACCTGCGAGCTAAGATATCCGAAGGC
GTGAGGTTGAATCCGGAACAGCACGGATCGAGTGTGATACAAGGAACAGCGATTTACGAATCC
GGTGTGTCTTCTCATGATCAGTCGCAGCATTATAATCGGAACTATATTCCAGTGAACCTTCTT
GAACCAAATCAGCAATTCTCCGGTCAAGACCAACCTCCTCTTCAACTTGTTTAA

FIG. 5A

WT pennycress SHP1
SEQ ID NO:18

MEEGGSSHDAESSKKIGRGKIEIKRIENTTNRQVTFCKRRNGLLKKAYELSVLCDAEVALVIF
STRGRLYEYANNSVKGTIERYKKACSDAVNPPSVTEANTQYYQQEASKLRRQIRDIQNSNRHI
VGESLGSLNFKELKNLEGRLEKGISRVRSKKNELLVAEIEYMQKREMDLQHDNMYLRAKISEG
VRLNPEQHGSSVIQGTAIYESGVSSHDQSQHYNRNYIPVNLLEPNQQFSGQDQPPLQLV

FIG. 5B modified pennycress SHP1 (shp1-1)
SEQ ID NO:19

ATGGAAGAGGGTGGGAATAGTCACGACGCAGAGAGTAGCAAGAAGATAGGGAGAGGGAAGATA
GAGATAAAGAGGATAGAGAACACAACGAATCGTCAAGTAACTTTCTGCAAACGACGCAATGGT
CTTCTCAAGAAAGCTTATGAGCTCTCTGTCTTGTGTGATGCCGAAGTTGCCCTCGTTATCTTC
TCCACTCGTGGCCGTCTCTATGAGTATGCCAACAACAGTGTGAAGGGTACAATTGAAAGGTAC
AAGAAAGCTTGTTCAGATGCCGTCAATCCCCCTCCGTCACCGAAGCTAATACTCAGTACTAT
CAGCAAGAAGCCTCTAAGCTTCGGAGGCAGATTCGAGACATTCAGAACTCAAACAGGCATATT
GTTGGGGAATCACTTGGTTCCTTGAACTTCAAGGAACTCAAAAACCTCGAAGGACGCCTTGAA
AAAGGAATTAGCCGCGTCCGATCCAAGAAGAATGAGTTGTTAGTGGCAGAGATTGAGTATATG
CAGAAGAGGGAAATGGATTTGCAACACGATAACATGTACCTGCGAGCTAAGATATCCGAAGGC
GTGAGGTTGAATCCGGAACAGCACGGATCGAGTGTGATACAAGGAACAGCGATTTACGAATCC
GGTGTGTCTTCTCATGATCAGTCGCAGCATTATAATCGGAACTATATTCCAGTGAACCTTCTT
GAACCAAATCAGCAATTCTCCGGTCAAGACCAACCTCCTCTTCAACTTGTTTAA

FIG. 5C modified pennycress SHP1 (shp1-1)
SEQ ID NO:20

MEEGGNSHDAESSKKIGRGKIEIKRIENTTNRQVTFCKRRNGLLKKAYELSVLCDAEVALVIF
STRGRLYEYANNSVKGTIERYKKACSDAVNPPSVTEANTQYYQQEASKLRRQIRDIQNSRHI
VGESLGSLNFKELKNLEGRLEKGISRVRSKKNELLVAEIEYMQKREMDLQHDNMYLRAKISEG
VRLNPEQHGSSVIQGTAIYESGVSSHDQSQHYNRNYIPVNLLEPNQQFSGQDQPPLQLV

FIG. 5D

WT pennycress SHP2
SEQ ID NO:21

ATGGAGGGTGGTGCGAGTAATGAAGTAGCAGAGAGCAGCAAGAAGATAGGGAGAGGGAAGATA
GAGATAAAGAGGATAGAGAATACTACGAATCGTCAAGTAACTTTCTGCAAACGACGCAATGGT
TTGCTCAAGAAAGCTTACGAGCTCTCCGTCTTGTGTGATGCGGAGGTTGCTCTCGTCATATTC
TCCACTCGAGGTCGTCTCTACGAGTACGCCAACAACAGTGTAAGAGGAACGATCGAAAGGTAC
AAGAAAGCTTGCTCCGACGCCGTGAATCCTCCTTCCGTCACCGAAGCTAATACTCAGTATTAT
CAGCAAGAGTCGTCGAAGCTACGGAGACAGATTCGAGACATTCAGAATCTGAACAGACACATT
CTTGGTGAGTCTCTTGGTTCCTTGAATCTCAAGGAACTAAAGAACCTCGAAGGTAGGCTTGAG
AAAGGCATCAGTCGCGTCCGCTCCAAGAAGCACGAGATGTTAGTTGCAGAGATAGAGTACATG
CAAAAAGGGAAATCGAGCTGCAAAACGATAACATGTATCTCCGATCCAAGATTACGGAAAGG
GCAGGAGTACAGCAGCAGGAATCGAGTGTGATACATCAAGGAACGGTTTACGAGTCGGGTGTA
TCGTCTTCTCATCAGACTGAGCAGTATAACCGGAGTTATATTCCGGTTAATCTGCTCGAACCA
AATCCGAATTCCTCCGACCAAGACCAACCACCTCTCCAACTTGTCTAA

FIG. 6A

WT pennycress SHP2
SEQ ID NO:22

MEGGASNEVAESSKKIGRGKIEIKRIENTTNRQVTFCKRRNGLLKKAYELSVLCDAEVALVIF
STRGRLYEYANNSVRGTIERYKKACSDAVNPPSVTEANTQYYQQESSKLRRQIRDIQNLNRHI
LGESLGSLNLKELKNLEGRLEKGISRVRSKKHEMLVAEIEYMQKREIELQNDNMYLRSKITER
AGVQQQESSVIHQGTVYESGVSSSHQTEQYNRSYIPVNLLEPNPNSSDQDQPPLQLV

FIG. 6B modified pennycress SHP2 (shp2-1)
SEQ ID NO:23

ATGGAGGGTGGTGCGAGTAATGAAGTAGCAGAGAGCAGCAAGAAGATAGGGAGAGGGAAGATA
GAGATAAAGAGGATAGAGAATACTACGAATCGTCAAGTAACTTTCTGCAAACGACGCAATGGT
TTGCTCAAGAAAGCTTACGAGCTCTCCGTCTTGTGTGATGCGGAGGTTACTCTCGTCATATTC
TCCACTCGAGGTCGTCTCTACGAGTACGCCAACAACAGTGTAAGAGGAACGATCGAAAGGTAC
AAGAAAGCTTGCTCCGACGCCGTGAATCCTCCTTCCGTCACCGAAGCTAATACTCAGTATTAT
CAGCAAGAGTCGTCGAAGCTACGGAGACAGATTCGAGACATTCAGAATCTGAACAGACACATT
CTTGGTGAGTCTCTTGGTTCCTTGAATCTCAAGGAACTAAAGAACCTCGAAGGTAGGCTTGAG
AAAGGCATCAGTCGCGTCCGCTCCAAGAAGCACGAGATGTTAGTTGCAGAGATAGAGTACATG
CAAAAAGGGAAATCGAGCTGCAAAACGATAACATGTATCTCCGATCCAAGATTACGGAAAGG
GCAGGAGTACAGCAGCAGGAATCGAGTGTGATACATCAAGGAACGGTTTACGAGTCGGGTGTA
TCGTCTTCTCATCAGACTGAGCAGTATAACCGGAGTTATATTCCGGTTAATCTGCTCGAACCA
AATCCGAATTCCTCCGACCAAGACCAACCACCTCTCCAACTTGTCTAA

FIG. 6C modified pennycress SHP2 (shp2-1)
SEQ ID NO:24

MEGGASNEVAESSKKIGRGKIEIKRIENTTNRQVTFCKRRNGLLKKAYELSVLCDAEVTLVIF
STRGRLYEYANNSVRGTIERYKKACSDAVNPPSVTEANTQYYQQESSKLRRQIRDIQNLNRHI
LGESLGSLNLKELKNLEGRLEKGISRVRSKKHEMLVAEIEYMQKREIELQNDNMYLRSKITER
AGVQQQESSVIHQGTVYESGVSSSHQTEQYNRSYIPVNLLEPNPNSSDQDQPPLQLV

FIG. 6D

WT pennycress PID
SEQ ID NO:25

ATGTTACGGGAATCAGACGGTGAGATGAGCTTAGAGACGACGAACTCGCCGATTAGCAGCGGA
ACAGAGAGCTGCAGCAGTTTCAGCCGGTTATCTTTCGACGCGCCGCCGTCAACCACCGCGATT
ATCCCCGAGGAAGAGAGCCTTCTCTCTATTAAACCGCACCGATCCTCCGATTTCGCATACTCG
GAGATCCGACGGCGGCGGAAACAAGGCCTCACCTTCCGAGATTTTCGACTCATGCGTCGAATC
GGCGCCGGAGACATCGGGACCGTGTACTTGTGCCGTCTCGCCGGAGACGAAGAAGAGAGCCGG
AGCTCGTATTTCGCGATGAAAGTGGTGGACAAAGAAGCGCTTGCGATGAAGAAGAAGATGCAC
AGAGCAGAGATGGAGAAGACGATTCTGAAGATGCTTGACCATCGTTTTGCCGACTCTTTAC
GCCGAGTTTGACGCATCGCATTTCTCTTGCATCGTCATGGAGTATTGCTCCGGCGGAGATTTG
CACTCCCTCCGTCACAAACAGCTCAACCGCAGATTCTCCCTTTCCTCCGCCAGATTTTACGCG
GCTGAAGTTCTTGTGGCGCTGGAATATCTACACATGCTGGGTATCATCTACAGAGATCTGAAG
CCTGAAAATATCTTAGTTAGATCGGACGGTCACATTATGCTCTCTGACTTTGATCTCTCCTTA
TGCTCCGACTCAATCGCAGCCGTTGAATCCTCCACATCTTCACCGGAGAATCAACCCCGTTCT
TCCCGGCGCCGACTCACTCGACTCTCTAGGATCTTCCACCGAGTCTTGCGGTCCAAAAAGGTT
CAGACGCTCGAACCGAACCGTCTCTTTGTTGCCGAACCGGTCACCGCTCGGTCCGGTTCGTTT
GTTGGTACGCATGAATACGTGGCACCAGAAGTCGCCTCAGGTGGGTCTCATGGAAATGCCGTT
GACTGGTGGGCCTTCGGAGTATTCCTCTACGAGATGATCTACGGCCGGACTCCATTCGCCGCG
CCGACGAATGACGTCATCCTTCGTAACATCGTGAAGAGACCGTTGAGTTTCCCGACCGATTCG
CCGTCGACGATGTTCGAGCTTCACGCGCGGGATTGATCTCCGGGTTGCTCAACAAGGATCCG
AACAAACGACTCGGGTCACGGCGAGGCGCGGCGGAGGTTAAAGTGCATCCGTTTTTCAAAGGT
CTAAACTTTGCGCTCATTCGTACATTAACTCCGCCGGAGATTCCCTCCGAGGTCAGGATACCG
AAGAAATCGTCGACGTTCGGTGGTAGAGCTAGTAAACCAGCGGCGTTCGATTACTTTTGA

FIG. 7A

WT pennycress PID
SEQ ID NO:26

MLRESDGEMSLETTNSPISSGTESCSSFSRLSFDAPPSTTAIIPEEESLLSIKPHRSSDFAYS
EIRRRRKQGLTFRDFRLMRRIGAGDIGTVYLCRLAGDEEESRSSYFAMKVVDKEALAMKKKMH
RAEMEKTILKMLDHPFLPTLYAEFDASHFSCIVMEYCSGGDLHSLRHKQLNRRFSLSSARFYA
AEVLVALEYLHMLGIIYRDLKPENILVRSDGHIMLSDFDLSLCSDSIAAVESSTSSPENQPRS
SRRRLTRLSRIFHRVLRSKKVQTLEPNRLFVAEPVTARSGSFVGTHEYVAPEVASGGSHGNAV
DWWAFGVFLYEMIYGRTPFAAPTNDVILRNIVKRPLSFPTDSPSTMFELHARGLISGLLNKDP
NKRLGSRRGAAEVKVHPFFKGLNFALIRTLTPPEIPSEVRIPKKSSTFGGRASKPAAFDYF

FIG. 7B modified pennycress PID (pid-1)
SEQ ID NO:27

ATGTTACGGGAATCAGACGGTGAGATGAGCTTAGAGACGACGAACTCGCCGATTAGCAGCGGA
ACAGAGAGCTGCAGCAGTTTCAGCCGGTTATCTTTCGACGCGCCGCCGTCAACCACCGCGATT
ATCCCCGAGGAAGAGAGCCTTCTCTCTATTAAACCGCACCGATCCTCCGATTTCGCATACTCG
GAGATCCGACGGCGGCGGAAACAAGGCCTCACCTTCCGAGATTTTCGACTCATGCGTCGAATC
GGCGCCGGAGACATCGGGACCGTGTACTTGTGCCGTCTCGCCGGAGACGAAGAAGAGAGCCGG
AGCTCGTATTTCGCGATGAAAGTGGTGGACAAAGAAGCGCTTGCGATGAAGAAGAAGATGCAC
AGAGCAGAGATGGAGAAGACGATTCTGAAGATGCTTGACCATCCGTTTTTGCCGACTCTTTAC
GCCGAGTTTGACGCATCGCATTTCTCTTACATCGTCATGGAGTATTGCTCCGGCGGAGATTTG
CACTCCCTCCGTCACAAACAGCTCAACCGCAGATTCTCCCTTTCCTCCGCCAGATTTTACGCG
GCTGAAGTTCTTGTGGCGCTGGAATATCTACACATGCTGGGTATCATCTACAGAGATCTGAAG
CCTGAAAATATCTTAGTTAGATCGGACGGTCACATTATGCTCTCTGACTTTGATCTCTCCTTA
TGCTCCGACTCAATCGCAGCCGTTGAATCCTCCACATCTTCACCGGAGAATCAACCCCGTTCT
TCCCGGCGCCGACTCACTCGACTCTCTAGGATCTTCCACCGAGTCTTGCGGTCCAAAAAGGTT
CAGACGCTCGAACCGAACCGTCTCTTTGTTGCCGAACCGGTCACCGCTCGGTCCGGTTCGTTT
GTTGGTACGCATGAATACGTGGCACCAGAAGTCGCCTCAGGTGGGTCTCATGGAAATGCCGTT
GACTGGTGGGCCTTCGGAGTATTCCTCTACGAGATGATCTACGGCCGGACTCCATTCGCCGCG
CCGACGAATGACGTCATCCTTCGTAACATCGTGAAGAGACCGTTGAGTTTCCCGACCGATTCG
CCGTCGACGATGTTCGAGCTTCACGCGCGGGATTGATCTCCGGGTTGCTCAACAAGGATCCG
AACAAACGACTCGGGTCACGGCGAGGCGCGGCGGAGGTTAAAGTGCATCCGTTTTTCAAAGGT
CTAAACTTTGCGCTCATTCGTACATTAACTCCGCCGGAGATTCCCTCCGAGGTCAGGATACCG
AAGAAATCGTCGACGTTCGGTGGTAGAGCTAGTAAACCAGCGGCGTTCGATTACTTTTGA

FIG. 7C modified pennycress PID (pid-1)
SEQ ID NO:28

MLRESDGEMSLETTNSPISSGTESCSSFSRLSFDAPPSTTAIIPEEESLLSIKPHRSSDFAYS
EIRRRRKQGLTFRDFRLMRRIGAGDIGTVYLCRLAGDEEESRSSYFAMKVVDKEALAMKKKMH
RAEMEKTILKMLDHPFLPTLYAEFDASHFSYIVMEYCSGGDLHSLRHKQLNRRFSLSSARFYA
AEVLVALEYLHMLGIIYRDLKPENILVRSDGHIMLSDFDLSLCSDSIAAVESSTSSPENQPRS
SRRRLTRLSRIFHRVLRSKKVQTLEPNRLFVAEPVTARSGSFVGTHEYVAPEVASGGSHGNAV
DWWAFGVFLYEMIYGRTPFAAPTNDVILRNIVKRPLSFPTDSPSTMFELHARGLISGLLNKDP
NKRLGSRRGAAEVKVHPFFKGLNFALIRTLTPPEIPSEVRIPKKSSTFGGRASKPAAFDYF

FIG. 7D

WT pennycress ADPG1
SEQ ID NO:29

ATGGCTCGTCGTTTCGGACTTCTTGCTATCTTCTTATGTGTTCTTTTGATGCTCTCGTGGTGC
GAAGCTTTGAGTAGCAACGTTGATGATGGATATGGTCATGAAGATGGAAGCTTCGAATCCGAT
AGCTTACTCAAACTTAAGAACGACGACGACGACGTTCTTACCTTGAAAAGCTCCGATAAAACC
ACTTCCGAATCATCAACTGTTAGTGTTACCGATTTCGGTGCTAAAGGAGATGGGGAAAACGAT
GATACTCAGGCCTTCAAGAAAGCATGGAAGAAAGCATGTTCAACAAAGGGAGTTACTAGTTTC
TTAATTCCTAAAGGAAAGACTTATCTCCTTAAGTCTACTCGATTCAGAGGCCCATGCAAATCT
TTACGTAACTTTCAGATCCTAGGCACTTTATCAGCATCTACAAAACGATCTGATTATAAGAAT
GACAGAAACCATTGGCTTGTCTTGGAGGACGTTAACAATCTATCACTGGATGGCGGCTCGACG
GGAATTATTGATGGCAACGGAAAAATCTGGTGGCAAAATTCATGCAAAATCGACCAATCTAAG
CCATGCACAAAAGCCCCAACGGCTCTTACTTTCTACAACTTAAAGAATTTGAATGTGAAGAAT
CTGAGAGTGAGAAATGCGCAGCAGATTCAGATTTCGATTGAGAAATGCAACAATGTTAACGTC
AACAATGTCGAGATCACTGCTCCTGACGATAGTCCCAACACCGATGGTATTCACATCACTAAT
ACACAAAACATTCGAATCTCCAATTCAGACATTGGCACAGGTGATGATTGCATATCCATTGAG
GATGGATCCCAAAATGTTCAAATCAATGATTTAACTTGCGGCCCCGGTCACGGGATCAGCATT
GGGAGTTTGGGGGATGACAATTCGAAAGCTTATGTCTCGGGGATTAATGTAGATGGTGCTAAG
CTCTCTTCTACTGATAATGGAGTTAGAATTAAAACTTACCAGGGAGGATCAGGAACTGCCAAG
AACATTAAATTTCAAAATATTCGTATGGAAAATGTCAAGAATCCAATCATAATCGACCAGAAC
TACTGCGACAAGGACAAATGCGAAGAACAAGAATCCGCGGTGCAAGTAAACAATGTGGTGTAC
CGGAACATAACCGGTACGAGCGCAACGGATGTGGCGATAATGTTTAATTGCAGTGAGAAATAT
CCATGCCAAGGGATTGTGCTTGAGAACGTGAATATCGAAGGAGGAACAGCTTCTTGCAAAAAT
GCCAATGTTAAGGATCAAGGCACTGTATCTCCTCAGTGCTCTTCCACTTGA

FIG. 8A

WT pennycress ADPG1
SEQ ID NO:30

MARRFGLLAIFLCVLLMLSWCEALSSNVDDGYGHEDGSFESDSLLKLKNDDDDVLTLKSSDKT
TSESSTVSVTDFGAKGDGENDDTQAFKKAWKKACSTKGVTSFLIPKGKTYLLKSTRFRGPCKS
LRNFQILGTLSASTKRSDYKNDRNHWLVLEDVNNLSLDGGSTGIIDGNGKIWWQNSCKIDQSK
PCTKAPTALTFYNLKNLNVKNLRVRNAQQIQISIEKCNNVNVNNVEITAPDDSPNTDGIHITN
TQNIRISNSDIGTGDDCISIEDGSQNVQINDLTCGPGHGISIGSLGDDNSKAYVSGINVDGAK
LSSTDNGVRIKTYQGGSGTAKNIKFQNIRMENVKNPIIIDQNYCDKDKCEEQESAVQVNNVVY
RNITGTSATDVAIMFNCSEKYPCQGIVLENVNIEGGTASCKNANVKDQGTVSPQCSST

FIG. 8B modified pennycress ADPG1 (adpg1-1)
SEQ ID NO:31

ATGGCTCGTCGTTTCGGACTTCTTGCTATCTTCTTATGTGTTCTTTTGATGCTCTCGTGGTGC
GAAGCTTTGAGTAGCAACGTTGATGATGGATATGGTCATGAAGATGGAAGCTTCGAATCCGAT
AGCTTACTCAAACTTAAGAACGACGACGACGACGTTCTTACCTTGAAAAGCTCCGATAAAACC
ACTTCCGAATCATCAACTGTTAGTGTTACCGATTTCGGTGCTAAAGGAGATGGGGAAAACGAT
GATACTCAGGCCTTCAAGAAAGCATGGAAGAAAGCATGTTCAACAAAGGGAGTTACTAGTTTC
TTAATTCCTAAAGGAAAGACTTATCTCCTTAAGTCTACTCGATTCAGAGGCCCATGCAAATCT
TTACGTAACTTTCAGATCCTAGGCACTTTATCAGCATCTACAAAACGATCTGATTATAAGAAT
GACAGAAACCATTGGCTTGTCTTGGAGGACGTTAACAATCTATCACTGGATGGCGGCTCGACG
GGAATTATTGATGGCAACGGAAAAATCTGGTGGCAAAATTCATGCAAAATCGACCAATCTAAG
CCATGCACAAAAGCCCCAACGGCTCTTACTTTCTACAACTTAAAGAATTTGAATGTGAAGAAT
CTGAGAGTGAGAAATGCGCAGCAGATTCAGATTTCGATTGAGAAATGCAACAATGTTAACGTC
AACAATGTCGAGATCACTGCTCCTGACGATAGTCCCAACACCGATGGTATTCACATCACTAAT
ACACAAAACATTCGAATCTCCAATTCAGACATTGGCACAGGTGATGATTGCATATCCATTGAG
GATGGATCCCAAAATGTTCAAATCAATGATTTAACTTGCGGCCCCGGTCACGGGATCAGCATT
GGGAGTTTGGGGGATGACAATTCGAAAGCTTATGTCTCGGGGATTAATGTAGATGGTGCTAAG
CTCTCTTCTACTGATAATGGAGTTAGAATTAAAACTTACCAGGGAGGATCAGGAACTGCCAAG
AACATTAAATTTCAAATATTCGTATGGAAATGTCAAGAATCCAATCATAATCGACCAGAAC
TACTGCGACAAGGACAAATGCGAAGAACAAGAATCCGCGGTGCAAGTAAACAATGTGGTGTAC
CGGAACATAACCGGTACGAGCGCAACGGATGTGGCGATAATGTTTAATTGCAGTGAGAAATAT
CCATGCCAAGGGATTGTGCTTGAGAACGTGAATATCGAAGGAGGAACAGCTTCTTGCAAAAAT
GCCAATGTTAAGGATCAAGGCACTGTATCTCCTCAGTGCTCTTCCACTTGA

FIG. 8C modified pennycress ADPG1 (adpg1-1)
SEQ ID NO:32

MARRFGLLAIFLCVLLMLSWCEALSSNVDDGYGHEMEASNPIAYSNLRTTTTTFLP

FIG. 8D modified pennycress ADPG1 (adpg1-2)
SEQ ID NO:33

ATGGCTCGTCGTTTCGGACTTCTTGCTATCTTCTTATGTGTTCTTTTGATGCTCTCGTGGTGC
GAAGCTTTGAGTAGCAACGTTGATGATGGATATGGTC*ATGA*AGATGGAAGCTTCGAATCCGAT
AGCTTACTCAAACTTAAGAACGACGACGACGACGTTCTTACCTTGAAAAGCTCCGATAAAACC
ACTTCCGAATCATCAACTGTTAGTGTTACCGATTTCGGTGCTAAAGGAGATGGGGAAAACGAT
GATACTCAGGCCTTCAAGAAAGCATGGAAGAAAGCATGTTCAACAAAGGGAGTTACTAGTTTC
TTAATTCCTAAAGGAAAGACTTATCTCCTTAAGTCTACTCGATTCAGAGGCCCATGCAAATCT
TTACGTAACTTTCAGATCCTAGGCACTTTATCAGCATCTACAAAACGATCTGATTATAAGAAT
GACAGAAACCATTGGCTTGTCTTGGAGGACGTTAACAATCTATCACTGGATGGCGGCTCGACG
GGAATTATTGATGGCAACGGAAAAATCTGGTGGCAAAATTCATGCAAAATCGACCAATCTAAG
CCATGCACAAAAGCCCCAACGGCTCTTACTTTCTACAACTTAAAGAATTTGAATGTGAAGAAT
CTGAGAGTGAGAAATGCGCAGCAGATTCAGATTTCGATTGAGAAATGCAACAATGTTAACGTC
AACAATGTCGAGATCACTGCTCCTGACGATAGTCCCAACACCGATGGTATTCACATCACTAAT
ACACAAAACATTCGAATCTCCAATTCAGACATTGGCACAGGTGATGATTGCATATCCATTGAG
GATGGATCCCAAAATGTTCAAATCAATGATTTAACTTGCGGCCCCGGTCACGGGATCAGCATT
GGGAGTTTGGGGGATGACAATTCGAAAGCTTATGTCTCGGGGATTAATGTAGATGGTGCTAAG
CTCTCTTCTACTGATAATGGAGTTAGAATTAAAACTTACCAGGGAGGATCAGGAACTGCCAAG
AACATTAAATTTCAAAATATTCGTATGGAAATGTCAAGAATCCAATCATAATCGACCAGAAC
TACTGCGACAAGGACAAATGCGAAGAACAAGAATCCGCGGTGCAAGTAAACAATGTGGTGTAC
CGGAACATAACCGGTACGAGCGCAACGGATGTGGCGATAATGTTTAATTGCAGTGAGAAATAT
CCATGCCAAGGGATTGTGCTTGAGAACGTGAATATCGAAGGAGGAACAGCTTCTTGCAAAAAT
GCCAATGTTAAGGATCAAGGCACTGTATCTCCTCAGTGCTCTTCCACTTGA

FIG. 8E modified pennycress ADPG1 (adpg1-2)
SEQ ID NO:34

MARRFGLLAIFLCVLLMLSWCEALSSNVDDGYGQMEASNPIAYSNLRTTTTTFLP

FIG. 8F

```
At_SPT     MISQREEREEKKQRVMGDKKLISSS-SSSSVYDTRINHHLHHPPSSSDEISQFLRHIFDR
Ta_SPT     ---------------MGDKKLISSSSSIASVYDTRNNNNHHHPPSSSDEISQFLRHIFDR
Ta_spt-1   ---------------MGDKKLISSSSSIASVYDTRNNNNHHHPPSSSDEISQFLXHIFDR
Gm_SPT     -----------------------------MAGDIGRALPPPDSEEFSTLFNQLLHN
Os_SPT     ------------------------------------------------------------
Sl_SPT     ------------------------MADPY-----RTNPHASSSLESEDMSSFFLNFLQG At_SPT     SSPLPSYYSPATTTTTASLIGVHGSGDPHADNSRSLVSHHPPSDSVLMSKRVGDFSEVLI
Ta_SPT     SSPLPSYYSPATMTTA---AIGV----HGDPHADNPRSFVS-HPPSDSALPSKRPADYSEVLI
Ta_spt-1   SSPLPSYYSPATMTTA---AIGV----HGDPHADNPRSFVS-HPPSDSALPSKRPADYSEVLI
Gm_SPT     SPPLGMD----------------------------------------PNHSPSDFTPHNT
Os_SPT     ------------------------------------------------------------
Sl_SPT     TPASSSAT------------AAAGFY----------------------------------

At_SPT     ---GGGSGSA---------AACFGFSGGGNNNNVQGNSS-GTRVSSSSVG-----------
Ta_SPT     --GSAVGSASAVGSGSAPCFGFSGGN--NIAQGNSS-GTRVSSSSVG-------------
Ta_spt-1   --GSAVGSASAVGSGSAPCFGFSGGN--NIAQGNSS-GTRVSSSSVG-------------
Gm_SPT     TININSNNNNNTVPSSPSNFNFSDPHHYIP---ASD-ATTFKQHNIN-------------
Os_SPT     ------------------------------------------------------------
Sl_SPT     -----NRSGPAPVAESSSSLNFSDPGRFYAAEFKEGVENVFASAGLGECDGMNSANRREF At_SPT     ASGNETDEYDCESEEGGEAVVDEAPSSKSGPSSRSSSKRCRAAEVHNLSEKRRRSRINEK
Ta_SPT     ASGNDTDEYDCESEEGVEAVVDDDLPSKSGPS-RSSSKRCRAAEVHNLSEKRRRSRINEK
Ta_spt-1   ASGNDTDEYDCESEEGVEAVVDDDLPSKSGPS-RSSSKRCRAAEVHNLSEKRRRSRINEK
Gm_SPT     HNNNHTPDFTSS------HVEKSVEASKPVPPPRSSSKRSRAAEFHNLSEKRRRSRINEK
Os_SPT     ----------EAG------GSSEPEAAAGAPPRGGSGSKRSRAAEVHNLSEKRRRSKINEK
Sl_SPT     LEDDKVDNFGFSSE------ECDGLDMPSDPTHPRSSKRSRSAEVHNLSEKRRRSRINEK At_SPT     MKALQSLIPNSNKTDKASMLDEAIEYLKQLQLQVQMLTMRNGINLHPLCLPGTTLHPLQL
Ta_SPT     MKALQSLIPNSNKTDKASMLDEAIEYLKQLQLQVQMLTMRNGINLHPLCLPGTTLHPLQL
Ta_spt-1   MKALQSLIPNSNKTDKASMLDEAIEYLKQLQLQVQMLTMRNGINLHPLCLPGTTLHPLQL
Gm_SPT     MKALQNLIPNSNKTDKASMLDEAIEYLKQLQLQVQMLMMRNGLSLHPMSLPGGL-RPMIM
Os_SPT     MKALQSLIPNSNKTDKASMLDEAIEYLKQLQLQVQMLSMRNGVYLNPSYLSGAL-EPAQA
Sl_SPT     LKALQNLIPNSNKTDKASMLDEAIEYLKQLQLQVQILTLRNGLSLYPGYVPGSLQ-SVQL At_SPT     SQIR---PPEATNDPLLNHTNQFASTSNAPEMIN------------------TVASS
Ta_SPT     SQVRGMPQEATNDHLLNHTNQFGSTSNAPEMIN------------------TVPSS
Ta_spt-1   SQVRGMPQEATNDHLLNHTNQFGSTSNAPEMIN------------------TVPSS
Gm_SPT     PQTGLNL--DGSNGFQNSTCAIASSSNDESLVRHAFSF----PKQCSISNKSIGVPSVKNI
Os_SPT     SQMFAAL--GGNNVTVVHPGTVMPPVNQSSGAHHLFDPLNSPPQN----QPQSLILPSVPST
Sl_SPT     PSGNE------FDGRSFMLSANGGATLP-VNREMPQTAFEISNQNP---------SGKPTITSH At_SPT     ------YALEP-SIRSHFGPFPLLTSPVEMSREGGLTHPRLNIGHSNANITGEQALFDGQ
Ta_SPT     ------YSLEP-SVRSHFGPFPLLTSHAEMSREGGLTHHRLSIGHSNTNLTGAQAVFNGQ
Ta_spt-1   ------YSLEP-SVRSHFGPFPLLTSHAEMSREGGLTHHRLSIGHSNTNLTGAQAVFNGQ
Gm_SPT     ATSDTSSTFHPSIKDALYGNMPQPFMDT-----------TKIGKPS-------------
Os_SPT     AIPE--PPFHLESSQSHLRQFQLP--------------------GSS-------------
Sl_SPT     NT-ENAVALE-TTIQNHYGLLNHLASSKDMCRDNTLSRLHLDMSCSGNNSSSGVSS----

At_SPT     --PDLKDRIT-
Ta_SPT     EQPDIKDRLT*
Ta_spt-1   EQPDIKDRLT*
Gm_SPT     --PDVS-----
Os_SPT     ---EVI-----
Sl_SPT     -----------
```

FIG. 9

```
AT_IND      MEN----GMYKKKGVC----DSCVSSKSRSNHSPKRSMMEPQP-HHLLMDWNKANDLLTQEH
Ta_IND      ------------------------------------------------MNWNKPNDLITQEY
Ta_ind-1    ------------------------------------------------MNWNKPNDLITQEY
Ta_ind-2    ------------------------------------------------MNWNKPNDLITQEY
Ta_ind-3    ------------------------------------------------MNWNKPNDLITQEY
Gm_IND      MDTNTSTLFTNVNSTWNLEKMETNEQQQHDDHSIILQVQD-PMGSGIWPIN-------NY
Os_IND      ------MTHNSSSSSWDLDMSLGSHHHP------LLF-DQP-PPPPPPPPP----------
Sl_IND      MDIN--HINKLTTSTWDPTMSNMDNQQV--------FRDQQQQQQPCLSSIPNDHIYHEH AT_IND      A---AFLNDPHHLMLDPPPETLIHLDE---------------------------------
Ta_IND      ----PFLHDP-HLMIDPPPETLSHFQPPPTLF------------------SGHGG-----
Ta_ind-1    ----PFLHDP-HLMIDPPPETLSHFQPPPTLF------------------SGHGG-----
Ta_ind-2    ----PFLHDP-HLMIDPPPETLSHFQPPPTLF------------------SGHGG-----
Ta_ind-3    ----PFLHDP-HLMIDPPPETLSHFQPPPTLF------------------SGHGG-----
Gm_IND      Q--NLL----QMHQTPNTTTSSTVIVPPSSS-------------------SGFLG-----
Os_IND      P--PLPFHLRHHPLDPSPS--SSLFPPPPHHHHHAHHLHHPLDLDQRRGHHDYGGGDQGG
Sl_IND      HHHQQQFHFERNPIWPS-----FPLQNPQHH-----HLPSSSTQQQ----------QQQQ AT_IND      ------------------------------DEEYDEDMDAMKEMQYMIAVMPVDIDPAT
Ta_IND      ------------------------------EEEEEEDNEEEEMDAMKEMQYTIAAMPVDIDPAT
Ta_ind-1    ------------------------------EEEEEEDNEEEEMDAMKEMQYTIAAMPVDIDPAT
Ta_ind-2    ------------------------------EEEEEEDNEEEEMDAMKEMQYTIAAMPVDIDPAT
Ta_ind-3    ------------------------------EEEEEEDNEEEEMDAMKEMQYTIAAMPVDIDPAT
Gm_IND      ------------------------------DILGVHHNLEEDEEPEEELGAMKEMMYKIAAMPVDIDPAT
Os_IND      DEELRLQQEAA-----AGGGGGGGQDGGGGGGDQDADEELGAMKEMMYRIAAMPVDIDPAT
Sl_IND      EEVVVVPFDHVLNNHVQTLIEDQEHDDQDEDEEEEEELGAMKEMMFKIASMQPVDIDPST AT_IND      VPKPNRRNVRISDDPQTVVARRRRERISEKIRILKRIVPGGAKMDTASMLDEAIRYTKFL
Ta_IND      VPKPNRRNVRVSDDTQTVVARRRREKISEKIRILKRMVPGGAKMDTASMLDEAIRYTKFL
Ta_ind-1    VSKPNRRNVRVSDDTQTVVARRRREKISEKIRILKRMVPGGAKMDTASMLDEAIRYTKFL
Ta_ind-2    VPKPNRRNVRVSDDTQTVVARRRREKISEKIRILKRMVPGGAKMDTASMLDEAIRYTKFL
Ta_ind-3    VPKPNRRNVRVSDDTQTVVTRRRREKISEKIRILKRMVPGGAKMDTASMLDEAIRYTKFL
Gm_IND      IRKPKRRNVRISDDPQSVAARHRRERISEKIRILQRLVPGGTKMDTASMLDEAIRYVKFL
Os_IND      IKKPRRRNVRISDDPQSVAARHRRERISERIRILQRLVPGGTKMDTASMLDEAIRYIKFL
Sl_IND      IRKPKRRNVRISNDPQSVAARLRRERISEKIRILQRLVPGGTKMDTASMLDEAIRYVKFL AT_IND      KRQVRILQPHSQIGAPMANPSYLCYYHN---------SQP--------------------
Ta_IND      KRQVKLLQPHSQLGAPMSDPSCLCYYHN---------SQT*-------------------
Ta_ind-1    KRQVKLLQPHSQLGAPMSDPSCLCYYHN---------SQT*-------------------
Ta_ind-2    KRQVKLLQPHSQLGAPMSDPSCLCYYHN---------SQT*-------------------
Ta_ind-3    KRQVKLLQPHSQLGAPMSDPSCLCYYHN---------SQT*-------------------
Gm_IND      KRQIRLLQSIPQPSR--QPPQCIGVAST-------TPHASTLL----LAPS-----SDWP
Os_IND      KRQVQELQHQPGPPPPPYPAGAAPAAGPS--TSAVGPPGRPFLPLGGGGPM-----IDWV
Sl_IND      KRQIRQLQSSNHNLPPAQIPVSSCPNNENWANNIVTPSTK-GLILGSSSSTTTNNVTTFV AT_IND      ------------------------------------------------------------
Ta_IND      ------------------------------------------------------------
Ta_ind-1    ------------------------------------------------------------
Ta_ind-2    ------------------------------------------------------------
Ta_ind-3    ------------------------------------------------------------
Gm_IND      F---APNVL----PRSTAVSASMDMSAGLGFDGHAHACDGSSSFNHHEVIS
Os_IND      G---LTRPVDIHGPTSSSSSSSMGGALGFGF-----GCGGGGQSSHGMH--
Sl_IND      GNTTLDPPYEVIGN------------------------------------
```

FIG. 12

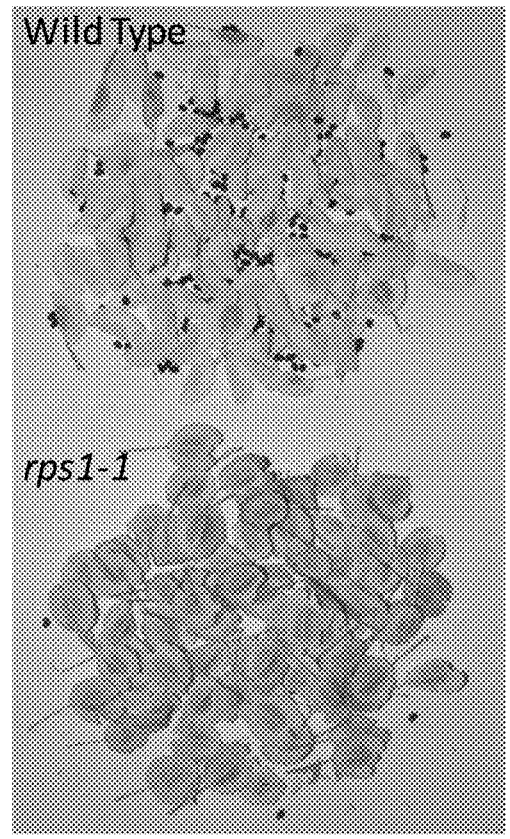
FIG. 13A　　　　　　　　　　FIG. 13B
Wild Type　　　　　　　　　E42 EMS mutant (rps1-1)
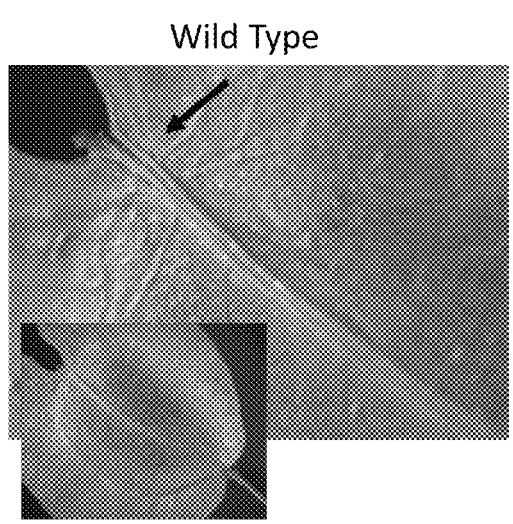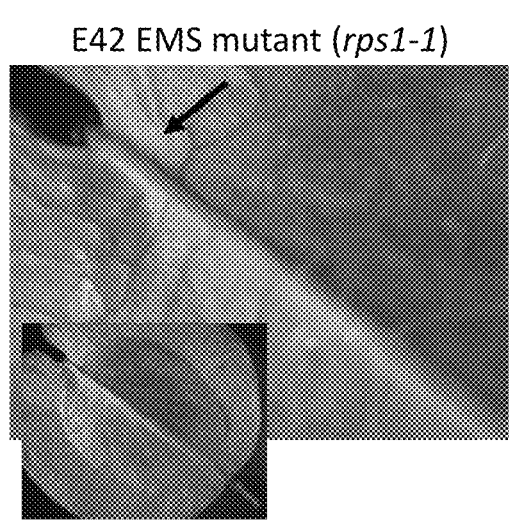
FIG. 13C　　　　　　　　　　FIG. 13D

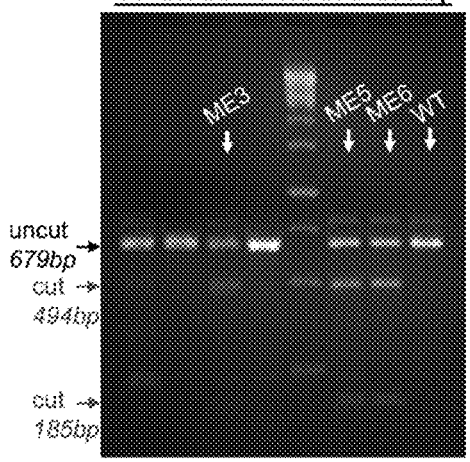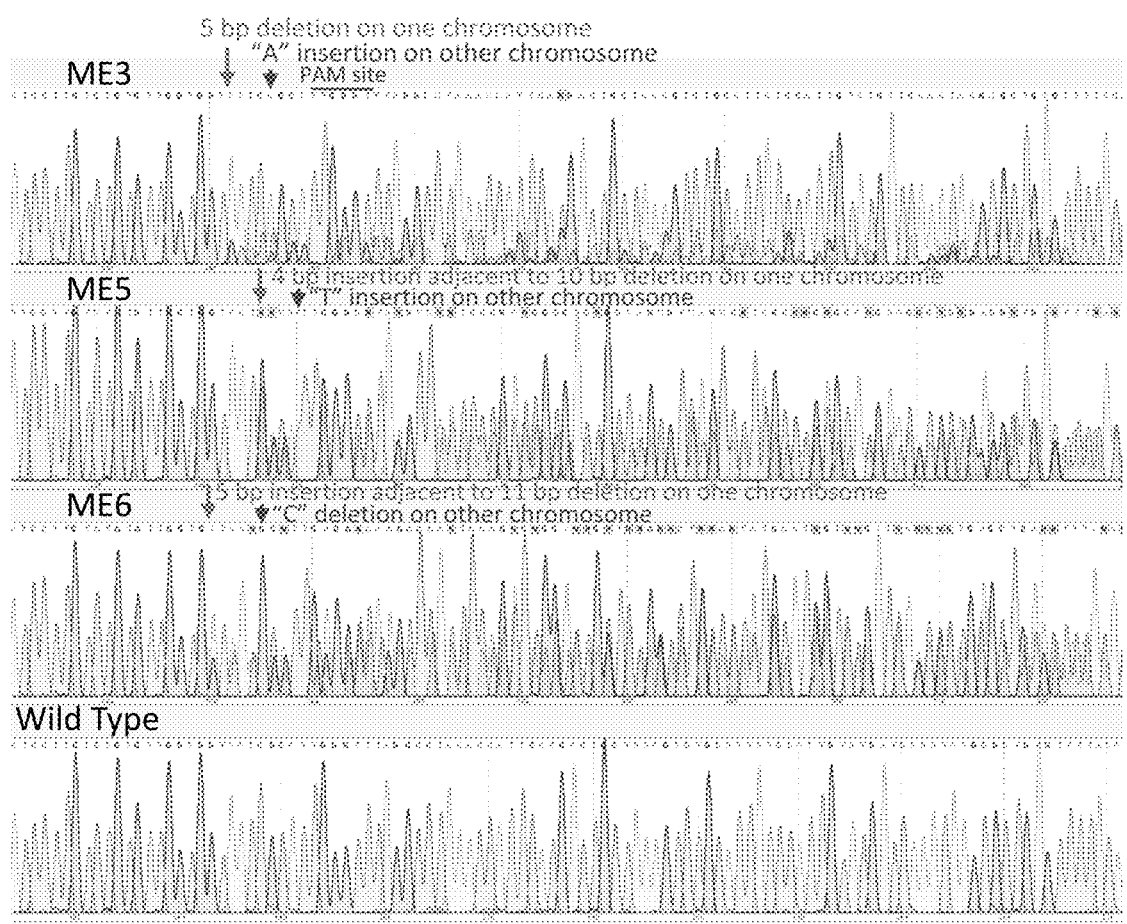
FIG. 15

```
Ta_PID    ------------------------------MLRESDGEMSLETTNSPISSGTESCSSFSR
Ta_pid-1  ------------------------------MLRESDGEMSLETTNSPISSGTESCSSFSR
At_PID    ------------------------------MLRESDGEMSLGTTNSPISSGTESCSSFSR
Gm_PID    ---------------------------METGGGRDSGMSSETINSSTQRTSMSNESVCS
Os_PID    MVAAVRAPVKPEMVELSPAAMERYSSDADTTAPNSSLSSAASSTGSLARCSSLSRLSFDC
Sl_PID    --------------------------MATTNRDESDKDSTASSSITMPESSRRSWMSSTNLS Ta_PID    LSFDAPPSTTAIIPEEESLLSIKPHRSSDFAYSEIRRRRKQGLT----FRDFRLMRRIGAG
Ta_pid-1  LSFDAPPSTTAIIPEEESLLSIKPHRSSDFAYSEIRRRRKQGLT----FRDFRLMRRIGAG
At_PID    LSFDAPP---STIPEEESFLSLKPHRSSDFAYAEIRRRKKQGLT----FRDFRLMRRIGAG
Gm_PID    TSFSRLSFDLPPPSSSPETLFVKPHRSSDFAYSAILRR-KSALT----FRDFHLLRRIGAG
Os_PID    SPSAAVAAAATSCSPFRASVLLRPHRSGDVAWAAIRAASTTSAAPLGPRDFKLVRRIGGG
Sl_PID    SFSSRRSSISLCNENPYFSNSHKPHKSNQISWELIRRIRVESGQ-IKLEHFRLLRRVGGG Ta_PID    DIGTVYLCRLAGD-----EEESRSSYFAMKVVDKEALAMKKKMHRAEMEKTILKMLDHPF
Ta_pid-1  DIGTVYLCRLAGD-----EEESRSSYFAMKVVDKEALAMKKKMHRAEMEKTILKMLDHPF
At_PID    DIGTVYLCRLAGD-----EEESRSSYFAMKVVDKEALALKKKMHRAEMEKTILKMLDHPF
Gm_PID    DIGTVYLCRLRHDAGDEDDDED-PCFYAMKVVDKEAVALKKKAQRAEMERKILKMVDHPF
Os_PID    DIGTVYLCRLRSS-----PERESPCMYAMKVVDRRAVARKQKLGRAAAEKRILRQLDHPF
Sl_PID    DIGSVYLCEIRNP-----VVGLPQCFYAMKVVDREAVEIRKKLQRGEMEKEILGIIDHPF Ta_PID    LPTLYAEFDAS-HFSCIVMEYCSGGDLHSLRHKQLNRRFSLSSARFYAAEVLVALEYLHM
Ta_pid-1  LPTLYAEFDAS-HFSXIVMEYCSGGDLHSLRHKQLNRRFSLSSARFYAAEVLVALEYLHM
At_PID    LPTLYAEFEAS-HFSCIVMEYCSGGDLHSLRHRQPHRRFSLSSARFYAAEVLVALEYLHM
Gm_PID    LPTLYAEFEAS-NFSCIVMEYCSGGDLHSLQHNHPNNRFSLSSARFYAAEVLVALEYLHM
Os_PID    LPTLFADFDATPHFSCAVMEFCPGGDLHSLRHRMPSRRFPLPSARFYAAEVLLAIEYLHM
Sl_PID    LPTLYAQFEAS-HYSCLVMEYCPGGDLHAVRQRQPGKRFSISSAKFYAAEILLALEYLHM Ta_PID    LGIIYRDLKPENILVRSDGHIMLSDFDLSLCSDSIAAVESSTSSPENQPR-------SSR
Ta_pid-1  LGIIYRDLKPENILVRSDGHIMLSDFDLSLCSDSIAAVESSTSSPENQPR-------SSR
At_PID    LGIIYRDLKPENILVRSDGHIMLSDFDLSLCSDSIAAVESSSSSPENQQL-------RSP
Gm_PID    LGIIYRDLKPENVLVRSDGHIMLSDFDLSLCSDAIPAVESPDCSLDPAFAPALR---YTR
Os_PID    MGIVYRDLKPENVLIRADGHIMLTDFDLSQSTTSPSLDGDTDTDDEASG-----------
Sl_PID    MGIVYRDLKPENVLVRSDGHIMLSDFDLSFKCDEVVPTLVKSKTTKSIAKTPRN--SYCA Ta_PID    RRLTRLSRIFHRVLRSKKVQTLEPNRLFVAEPVTARSGSFVGTHEYVAPEVASGGSHGNA
Ta_pid-1  RRLTRLSRIFHRVLRSKKVQTLEPNRLFVAEPVTARSGSFVGTHEYVAPEVASGGSHGNA
At_PID    RRFTRLARLFQRVLRSKKVQTLEPTRLFVAEPVTARSGSFVGTHEYVAPEVASGGSHGNA
Gm_PID    QYSTPFSCLSNRVFRSRKVQTLQPNRLFVAEPVGARSCSFVGTHEYVSPEVASGNSHGNA
Os_PID    --GASCFPDHLLRFKRRPNAVAAPRPRFVAEPVDARSCSFVGTHEYVAPEVASGGAHGAA
Sl_PID    MPIQPVLSCFLSQKTEQNHENQEEDQEIVAEPINARSKSFVGTHEYLAPEVISGQGHGSA Ta_PID    VDWWAFGVFLYEMIYGRTPFAAPTNDVILRNIVKRPLSFPTDSPST-----MFELHARGLI
Ta_pid-1  VDWWAFGVFLYEMIYGRTPFAAPTNDVILRNIVKRPLSFPTDSPST----MFELHARGLI
At_PID    VDWWAFGVFLYEMIYGKTPFVAPTNDVILRNIVKRQLSFPTDSPAT----MFELHARNLI
Gm_PID    VDWWSFGIFIYEMVYGRTPFAGSSNEATLRSIIKKPLAFPTSTPSS----TLEMHARDLI
Os_PID    VDWWAYGVFLYELIYGRTPFAGATNEATLRNIVRRPLAFPSGSGSCG---PADADARDLI
Sl_PID    VDWWTLGVFLYELIFGTTPFKGENNEKTLVNILKKPLTFPRIAISSSKEYEEMVKVQDLI Ta_PID    SGLLNKDPNKRLGSRRGAAEVKVHPFFKGLNFALIRTLTPPEIPSEVRIP--KKSSTFGG
Ta_pid-1  SGLLNKDPNKRLGSRRGAAEVKVHPFFKGLNFALIRTLTPPEIPSEVRIP---KKSSTFGG
At_PID    SGLLNKDPTKRLGSRRGAAEVKVHPFFKGLNFALIRTLTPPEIPSSVVKKPMKSATFSGR
Gm_PID    SGLLNKDPNRRLGSKRGSADVKKHPFFAGLNLALIRTVTPPEVPSLRRHKTTPFYYPANV
Os_PID    ARLLAKDPAARLGSRRGAADVKSHPFFKSLNLALLRSSRFPVVPGAGAGAAPLHRSQSCK
Sl_PID    SRLLVKNPKKRIGSLQGSVEIKKHEFFKGVNWALIRSIKPPQVPNDLVKMRGVVPKLSKK Ta_PID    RASKPAAFDYF--------------
Ta_pid-1  RASKPAAFDYF--------------
At_PID    SSNKPAAFDYF--------------
Gm_PID    NNSRQQLTAFDYF------------
Os_PID    AAPTTPPPPTTTKPANATARFDLF
Sl_PID    QREEPYQIPQYFDYF----------
```

FIG. 17

Wild type　　　Representative shatter mutant (pid-1)

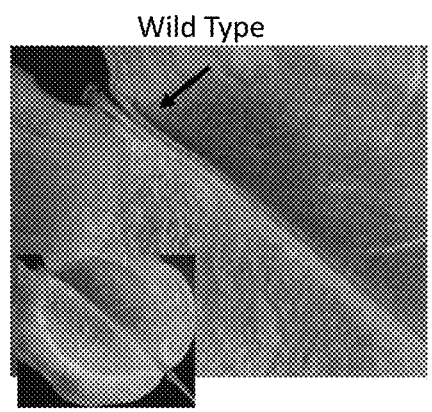
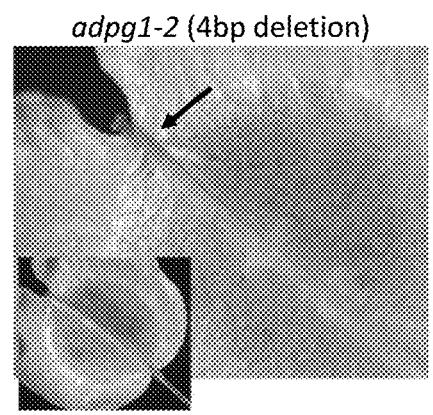
FIG. 19A          FIG. 19B
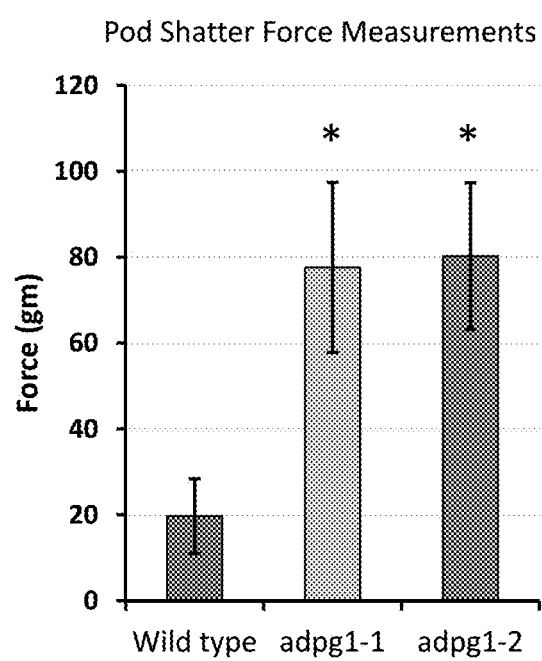
FIG. 19C

SEQUENCE LISTING

<160> NUMBER OF SEQ ID NOS: 70

<210> SEQ ID NO 1
<211> LENGTH: 1806
<212> TYPE: DNA
<213> ORGANISM: Thlaspi arvense

<400> SEQUENCE: 1

```
atgatatcac aaagagaaga gagagaagag aagagagtga tgggagataa gaaattgatt      60
tcatcgtctt cttctattgc ctcggtttac gatactcgta ataataacaa tcatcatcac     120
ccaccgtctt cctccgacga gatttctcag tttctccggc atattttcga ccgttcttct     180
cctctccctt cttactattc tccggcgacg atgacgacgg cggcaatcgg agtgcacggc     240
gacccacatg cagacaaccc ccggagcttc gtttctcatc cgccgtctga ctctgcgctc     300
ccgtcgaagc gccccgctga ttactctgag gttttaatag gctccgccgt tggatcagcc     360
tccgccgttg gatcaggctc agcccccgtgt tttggtttct ccggaggtaa taacattgcc     420
caaggaaaca gctcagggac tcgagtttcg tcttcttccg ttggagctag cgggaatgac     480
accgacgagt acgattgcga aagcgaggtc tctctctctc tatgtgcatg ttctaaaagt     540
tcccatcttt gtctgtttcc tgagaaaatg ttatactgtg acttctctctna acggatctgt     600 actttctttt ctcaccattc aagtgagcaa attaaatttg ccttttttt ctgtgtgtgt     660 gttttttag tgaagtttgt gaatgttaat aatgcacaca gagtgtttgt tgatttgctt     720
gaatgaaatc aggaaggagt agaagctgtg gttgatgatg atcttccctc aaagtctggt     780
ccttctcgta gctcatcaaa gcgatgcaga gctgctgaag ttcataattt gtctgaaaag     840 gtttttatt tgctccttgt ttttgtttc tctcccaaaa tcacattcct ttttactcag     900
agattgatgt gatcttgttc tgacagagga ggagaagtag gatcaacgaa aaaatgaaag     960
ctttacaaag tctcatccca aattcaaaca aggtaaaaat acatacaaat gctgaatcat    1020
tctctcattt gtctcttgtt attgtgtctg attatataat gtccattgca atgcgttgat    1080
gattggtggg aagacggata aggcttcaat gcttgatgaa gctatagagt atctgaaaca    1140
gcttcagctt caagtccagg tcacaaaata tccattctca aaaagatatg atacattcac    1200
ttttcccgaa tcaatcttat gaacagatta ctctgtgttt tgcagatgtt gacaatgagg    1260
aatggaataa acttgcatcc tctgtgctta cctggaacta cattcacccc attgcaactc    1320
tctcaggttc gagggatgcc tcaagaagca accaatgatc atctgcttaa tcacaccaac    1380
```

```
caattcggtt cgacctctaa cgcacctgag atgatcaaca ccgtgccttc ctcatactcg   1440
ttggaacctt ccgtccgcag tcactttgga cctttccctc tccttacttc acacgcggtg   1500
cgtggtttca taacacattt tcaatctata aaccctagat tcttgaaagc tagtgttctt   1560
actagaaatt tattgttttt tcgtaaagga gatgagtcga gaaggtggac taactcatca   1620
caggttgagc attggtcatt ccaacacaaa cttaaccggt aaagtcttcc tgatttctga   1680
attctcgtga agaagttttt aagacattga caatgttaaa aatgttgcga cgtttgggta   1740
tttgcagggg cacaagctgt gtttaatgga caagaacaac ctgacataaa agatcgactt   1800
acttga                                                              1806
```

<210> SEQ ID NO 2
<211> LENGTH: 375
<212> TYPE: PRT
<213> ORGANISM: Thlaspi arvense

<400> SEQUENCE: 2

```
Met Ile Ser Gln Arg Glu Glu Arg Glu Lys Arg Val Met Gly Asp
 1               5                  10                  15

Lys Lys Leu Ile Ser Ser Ser Ser Ile Ala Ser Val Tyr Asp Thr
            20                  25                  30

Arg Asn Asn Asn Asn His His His Pro Pro Ser Ser Ser Asp Glu Ile
        35                  40                  45

Ser Gln Phe Leu Arg His Ile Phe Asp Arg Ser Ser Pro Leu Pro Ser
    50                  55                  60

Tyr Tyr Ser Pro Ala Thr Met Thr Thr Ala Ala Ile Gly Val His Gly
65                  70                  75                  80

Asp Pro His Ala Asp Asn Pro Arg Ser Phe Val Ser His Pro Pro Ser
                85                  90                  95

Asp Ser Ala Leu Pro Ser Lys Arg Pro Ala Asp Tyr Ser Glu Val Leu
            100                 105                 110

Ile Gly Ser Ala Val Gly Ser Ala Ser Ala Val Gly Ser Gly Ser Ala
        115                 120                 125

Pro Cys Phe Gly Phe Ser Gly Gly Asn Asn Ile Ala Gln Gly Asn Ser
    130                 135                 140

Ser Gly Thr Arg Val Ser Ser Ser Ser Val Gly Ala Ser Gly Asn Asp
145                 150                 155                 160

Thr Asp Glu Tyr Asp Cys Glu Ser Glu Glu Gly Val Glu Ala Val Val
                165                 170                 175

Asp Asp Asp Leu Pro Ser Lys Ser Gly Pro Ser Arg Ser Ser Ser Lys
            180                 185                 190

Arg Cys Arg Ala Ala Glu Val His Asn Leu Ser Glu Lys Arg Arg Arg
        195                 200                 205

Ser Arg Ile Asn Glu Lys Met Lys Ala Leu Gln Ser Leu Ile Pro Asn
    210                 215                 220

Ser Asn Lys Thr Asp Lys Ala Ser Met Leu Asp Glu Ala Ile Glu Tyr
225                 230                 235                 240

Leu Lys Gln Leu Gln Leu Gln Val Gln Met Leu Thr Met Arg Asn Gly
                245                 250                 255

Ile Asn Leu His Pro Leu Cys Leu Pro Gly Thr Thr Leu His Pro Leu
            260                 265                 270

Gln Leu Ser Gln Val Arg Gly Met Pro Gln Glu Ala Thr Asn Asp His
        275                 280                 285

Leu Leu Asn His Thr Asn Gln Phe Gly Ser Thr Ser Asn Ala Pro Glu
```

```
                290                 295                 300
Met Ile Asn Thr Val Pro Ser Ser Tyr Ser Leu Glu Pro Ser Val Arg
305                 310                 315                 320

Ser His Phe Gly Pro Phe Pro Leu Leu Thr Ser His Ala Glu Met Ser
                325                 330                 335

Arg Glu Gly Gly Leu Thr His His Arg Leu Ser Ile Gly His Ser Asn
            340                 345                 350

Thr Asn Leu Thr Gly Ala Gln Ala Val Phe Asn Gly Gln Glu Gln Pro
        355                 360                 365

Asp Ile Lys Asp Arg Leu Thr
    370                 375

<210> SEQ ID NO 3
<211> LENGTH: 1806
<212> TYPE: DNA
<213> ORGANISM: Artificial Sequence
<220> FEATURE:
<223> OTHER INFORMATION: modified pennycress SPT nucleotide sequence

<400> SEQUENCE: 3
atgatatcac aaagagaaga gagagaagag aagagagtga tgggagataa gaaattgatt      60
tcatcgtctt cttctattgc ctcggtttac gatactcgta ataataacaa tcatcatcac     120
ccaccgtctt cctccgacga gatttctcag tttctctggc atattttcga ccgttcttct     180
cctctcccct tcttactatt ccggcgacg atgacgacgg cggcaatcgg agtgcacggc      240
gacccacatg cagacaaccc ccggagcttc gtttctcatc cgccgtctga ctctgcgctc     300
ccgtcgaagc gccccgctga ttactctgag gttttaatag gctccgccgt tggatcagcc     360
tccgccgttg gatcaggctc agcccgtgt tttggtttct ccggaggtaa taacattgcc      420
caaggaaaca gctcagggac tcgagtttcg tcttcttccg ttggagctag cgggaatgac     480
accgacgagt acgattgcga aagcgaggtc tctctctctc tatgtgcatg ttctaaaagt     540
tcccatcttt gtctgttttcc tgagaaaatg ttatactgtg actttctcta acggatctgt     600
actttctttt ctcaccattc aagtgagcaa attaaatttg ccttttttttt ctgtgtgtgt     660 gtttttttag tgaagtttgt gaatgttaat aatgcacaca gagtgtttgt tgatttgctt     720
gaatgaaatc aggaaggagt agaagctgtg gttgatgatg atcttccctc aaagtctggt     780
ccttctcgta gctcatcaaa gcgatgcaga gctgctgaag ttcataattt gtctgaaaag     840
gttttttatt tgctccttgt ttttgttttc tcccaaaaa tcacattcct ttttactcag      900
agattgatgt gatcttgttc tgacagagga ggagaagtag gatcaacgaa aaaatgaaag     960
ctttacaaag tctcatccca aattcaaaca aggtaaaaat acatacaaat gctgaatcat    1020
tctctcattt gtctcttgtt attgtgtctg attatataat gtccattgca atgcgttgat    1080
gattggtggg aagacggata aggcttcaat gcttgatgaa gctatagagt atctgaaaca    1140
gcttcagctt caagtccagg tcacaaaata tccattctca aaaagatatg atacattcac    1200
ttttcccgaa tcaatcttat gaacagatta ctctgtgttt tgcagatgtt gacaatgagg    1260
aatggaataa acttgcatcc tctgtgctta cctggaacta cattcaccc attgcaactc    1320 tctcaggttc gagggatgcc tcaagaagca accaatgatc atctgcttaa tcacaccaac    1380
caattcggtt cgacctctaa cgcacctgag atgatcaaca ccgtgccttc ctcatactcg    1440
ttggaacctt ccgtccgcag tcactttgga cctttccctc tccttacttc acacgcggtg    1500
cgtggtttca taacacattt tcaatctata accctagat tcttgaaagc tagtgttctt      1560
```

-continued

```
actagaaatt tattgttttt tcgtaaagga gatgagtcga gaaggtggac taactcatca    1620
caggttgagc attggtcatt ccaacacaaa cttaaccggt aaagtcttcc tgatttctga    1680
attctcgtga agaagttttt aagacattga caatgttaaa aatgttgcga cgtttgggta    1740
tttgcagggg cacaagctgt gtttaatgga caagaacaac ctgacataaa agatcgactt    1800
acttga                                                              1806
```

<210> SEQ ID NO 4
<211> LENGTH: 375
<212> TYPE: PRT
<213> ORGANISM: Artificial Sequence
<220> FEATURE:
<223> OTHER INFORMATION: modified pennycress SPT polypeptide sequence

<400> SEQUENCE: 4

```
Met Ile Ser Gln Arg Glu Glu Arg Glu Glu Lys Arg Val Met Gly Asp
1               5                   10                  15

Lys Lys Leu Ile Ser Ser Ser Ser Ile Ala Ser Val Tyr Asp Thr
            20                  25                  30

Arg Asn Asn Asn Asn His His His Pro Pro Ser Ser Ser Asp Glu Ile
        35                  40                  45

Ser Gln Phe Leu Trp His Ile Phe Asp Arg Ser Ser Pro Leu Pro Ser
    50                  55                  60

Tyr Tyr Ser Pro Ala Thr Met Thr Thr Ala Ala Ile Gly Val His Gly
65                  70                  75                  80

Asp Pro His Ala Asp Asn Pro Arg Ser Phe Val Ser His Pro Pro Ser
                85                  90                  95

Asp Ser Ala Leu Pro Ser Lys Arg Pro Ala Asp Tyr Ser Glu Val Leu
            100                 105                 110

Ile Gly Ser Ala Val Gly Ser Ala Ser Ala Val Gly Ser Gly Ser Ala
        115                 120                 125

Pro Cys Phe Gly Phe Ser Gly Gly Asn Asn Ile Ala Gln Gly Asn Ser
    130                 135                 140

Ser Gly Thr Arg Val Ser Ser Ser Val Gly Ala Ser Gly Asn Asp
145                 150                 155                 160

Thr Asp Glu Tyr Asp Cys Glu Ser Glu Glu Gly Val Glu Ala Val Val
                165                 170                 175

Asp Asp Asp Leu Pro Ser Lys Ser Gly Pro Ser Arg Ser Ser Ser Lys
            180                 185                 190

Arg Cys Arg Ala Ala Glu Val His Asn Leu Ser Glu Lys Arg Arg Arg
        195                 200                 205

Ser Arg Ile Asn Glu Lys Met Lys Ala Leu Gln Ser Leu Ile Pro Asn
    210                 215                 220

Ser Asn Lys Thr Asp Lys Ala Ser Met Leu Asp Glu Ala Ile Glu Tyr
225                 230                 235                 240

Leu Lys Gln Leu Gln Leu Gln Val Gln Met Leu Thr Met Arg Asn Gly
                245                 250                 255

Ile Asn Leu His Pro Leu Cys Leu Pro Gly Thr Thr Leu His Pro Leu
            260                 265                 270

Gln Leu Ser Gln Val Arg Gly Met Pro Gln Glu Ala Thr Asn Asp His
        275                 280                 285

Leu Leu Asn His Thr Asn Gln Phe Gly Ser Thr Ser Asn Ala Pro Glu
    290                 295                 300

Met Ile Asn Thr Val Pro Ser Ser Tyr Ser Leu Glu Pro Ser Val Arg
305                 310                 315                 320
```

```
Ser His Phe Gly Pro Phe Pro Leu Leu Thr Ser His Ala Glu Met Ser
                325                 330                 335

Arg Glu Gly Gly Leu Thr His His Arg Leu Ser Ile Gly His Ser Asn
            340                 345                 350

Thr Asn Leu Thr Gly Ala Gln Ala Val Phe Asn Gly Gln Glu Gln Pro
        355                 360                 365

Asp Ile Lys Asp Arg Leu Thr
    370                 375

<210> SEQ ID NO 5
<211> LENGTH: 973
<212> TYPE: DNA
<213> ORGANISM: Thlaspi arvense

<400> SEQUENCE: 5
atgggcaatc ccgacgacgg tgatcgtctt cctcctccat cttcttccga cgaactctcg      60
agcgttctcc ggcagattct gtcccgtgcc ccgataactc aaccttcgtc gtcaccaccg     120
aggagagtcg tttcctccgc tgaaatgttc gaccggacct ccctttcgt tcccggcgga     180 gcggtttctt ccgccgccta aaagtcgct ggcgaagaca atgtgcttt cgaaaacaag      240 gtaagctaac attttaagc tgtcgagaaa cttcactcgc ttcgtttatg aattaagcta      300
acatttcttt gtaatggtaa caacactaaa gagaaatgga ggagctaaac atcgaaattc      360
gttgaagaga acaatgatg cacaattcca caacttgtct gaaaaggttc tgtcttttaa      420
tcttctaaag attctcgatt tgagaaagaa aagcaattgt gattttaatt tatagaatct      480
gaaattattt gcagaggagg aggagcaaga tcaacgagaa aatgaaagct ttgcagaaac      540
tgatacccaa ttccaacaag gtaaatgaaa aaagttggaa tctttctact tctgaataca      600
atcgtgagaa acaccgttat gcttttgttt gtttgtttgt agactgataa agcctcaatg      660
ctcgatgaag ctatagagta tatgaagcag cttcaacttc aagtgcaggt ttttggcttt      720
actaagatca tatacaacca aattataatt ttttgtaaaa ctcagcgctt atttgatcat      780
acaatggata atgcagactt tagcagtcat gaatggttta ggcctaaacc caatgcgatt      840
accaccaaca cagacaagga tcaatgaggc cttacacatg cagactctgc ttggcggttc      900
tcactcgctt gttcaccgtg aaccacccga agcaagtcaa gaaatgtgct tttccgctgc      960
ggctcgtctt taa                                                        973

<210> SEQ ID NO 6
<211> LENGTH: 207
<212> TYPE: PRT
<213> ORGANISM: Thlaspi arvense

<400> SEQUENCE: 6

Met Gly Asn Pro Asp Asp Gly Asp Arg Leu Pro Pro Pro Ser Ser Ser
1               5                   10                  15

Asp Glu Leu Ser Ser Val Leu Arg Gln Ile Leu Ser Arg Ala Pro Ile
            20                  25                  30

Thr Gln Pro Ser Ser Pro Pro Arg Arg Val Val Ser Ser Ala Glu
        35                  40                  45

Met Phe Asp Arg Thr Phe Pro Phe Val Pro Gly Gly Ala Val Ser Ser
    50                  55                  60

Ala Ala Tyr Lys Val Ala Gly Glu Asp Lys Cys Ala Phe Glu Asn Lys
65                  70                  75                  80

Arg Asn Gly Gly Ala Lys His Arg Asn Ser Leu Lys Arg Asn Asn Asp
```

85                  90                  95
Ala Gln Phe His Asn Leu Ser Glu Lys Arg Arg Ser Lys Ile Asn
                100                 105                 110

Glu Lys Met Lys Ala Leu Gln Lys Leu Ile Pro Asn Ser Asn Lys Thr
            115                 120                 125

Asp Lys Ala Ser Met Leu Asp Glu Ala Ile Glu Tyr Met Lys Gln Leu
        130                 135                 140

Gln Leu Gln Val Gln Thr Leu Ala Val Met Asn Gly Leu Gly Leu Asn
145                 150                 155                 160

Pro Met Arg Leu Pro Pro Thr Gln Thr Arg Ile Asn Glu Ala Leu His
                165                 170                 175

Met Gln Thr Leu Leu Gly Gly Ser His Ser Leu Val His Arg Glu Pro
            180                 185                 190

Pro Glu Ala Ser Gln Glu Met Cys Phe Ser Ala Ala Ala Arg Leu
        195                 200                 205

<210> SEQ ID NO 7
<211> LENGTH: 977
<212> TYPE: DNA
<213> ORGANISM: Artificial Sequence
<220> FEATURE:
<223> OTHER INFORMATION: modified pennycress ALC nucleotide sequence

<400> SEQUENCE: 7
atgggcaatc ccgacgacgg tgatcgtctt cctcctccat cttcttccga cgaactctcg      60
agcgttctcc ggcagattct gtcccgtgcc ccgataactc aaccttcgtc gtcaccaccg     120
aggagagtcg tttcctccgc tgaaatgttc gaccggacct ccctttcgt tcccggcgga     180 gcggtttctt ccgccgccta taaagtcgct ggcgaagaca atgtgctttt cgaaaacaag     240
gtaagctaac attttaagc tgtcgagaaa cttcactcgc ttcgtttatg aattaagcta     300
acatttcttt gtaatggtaa caacactaaa gagaaatgga ggagctaaac atcgaaattc     360
gttgaagaga aacaatgatg cacaattcca caacttgtct gaaaaggttc tgtcttttaa     420
tcttctaaag attctcgatt tgagaaagaa aagcaattgt gatttaatt tatagaatct     480 gaaattattt gcagaggagg aggagcaaga tcaacgagaa aatgaaagct ttgcagaaac     540 tgataccaa ttccaacaag gtaaatgaaa aaagttggaa tctttctact tctgaataca     600
atcgtgagaa acaccgttat gcttttgttt gttgtttgt agactgataa agcctcaatg     660
ctcgatgaag ctatagagta tatgaagcag cttcaacttc aagtgcaggt ttttggcttt     720
actaagatca tatacaacca aattataatt ttttgtaaaa ctcagcgctt atttgatcat     780
acaatggata tgcagacttt tagcagtcat gaatggttta ggcctaaacc caatgcgtct     840
cattaccacc aacacagaca aggatcaatg aggcccttaca catgcagact ctgcttggcg     900
gttctcactc gcttgttcac cgtgaaccac ccgaagcaag tcaagaaatg tgcttttccg     960
ctgcggctcg tctttaa                                                   977

<210> SEQ ID NO 8
<211> LENGTH: 205
<212> TYPE: PRT
<213> ORGANISM: Artificial Sequence
<220> FEATURE:
<223> OTHER INFORMATION: modified pennycress ALC polypeptide sequence

<400> SEQUENCE: 8

Met Gly Asn Pro Asp Asp Gly Asp Arg Leu Pro Pro Pro Ser Ser Ser
1               5                   10                  15

```
Asp Glu Leu Ser Ser Val Leu Arg Gln Ile Leu Ser Arg Ala Pro Ile
             20                  25                  30

Thr Gln Pro Ser Ser Pro Pro Arg Arg Val Val Ser Ser Ala Glu
         35                  40                  45

Met Phe Asp Arg Thr Phe Pro Phe Val Pro Gly Gly Ala Val Ser Ser
 50                  55                  60

Ala Ala Tyr Lys Val Ala Gly Glu Asp Lys Cys Ala Phe Glu Asn Lys
 65                  70                  75                  80

Arg Asn Gly Gly Ala Lys His Arg Asn Ser Leu Lys Arg Asn Asn Asp
                 85                  90                  95

Ala Gln Phe His Asn Leu Ser Glu Lys Arg Arg Arg Ser Lys Ile Asn
            100                 105                 110

Glu Lys Met Lys Ala Leu Gln Lys Leu Ile Pro Asn Ser Asn Lys Thr
        115                 120                 125

Asp Lys Ala Ser Met Leu Asp Glu Ala Ile Glu Tyr Met Lys Gln Leu
130                 135                 140

Gln Leu Gln Val Gln Thr Leu Ala Val Met Asn Gly Leu Gly Leu Ile
145                 150                 155                 160

Ser Leu Pro Pro Thr Gln Thr Arg Ile Asn Glu Ala Leu His Met Gln
                165                 170                 175

Thr Leu Leu Gly Gly Ser His Ser Leu Val His Arg Glu Pro Pro Glu
            180                 185                 190

Ala Ser Gln Glu Met Cys Phe Ser Ala Ala Ala Arg Leu
        195                 200                 205
```

<210> SEQ ID NO 9
<211> LENGTH: 519
<212> TYPE: DNA
<213> ORGANISM: Thlaspi arvense

<400> SEQUENCE: 9

```
atgaattgga caaacctaa tgatctcatc acacaagaat ccccctttct ccacgatcct    60
catctcatga tagatccacc tcccgaaacc ctaagtcatt tccagccccc gccgacactt   120
ttctccggtc acgaggggga ggaagaagaa gaagaagata atgaagagga agatatggat   180
gcgatgaagg agatgcagta cacgatcgct gccatgcagc ccgtggacat cgatccagcc   240
accgttccta aaccgaaccg ccgtaacgta agggtaagcg acgacactca gacggtggtg   300
actcgtcggc gtcgagaaaa gataagcgag aagatccgaa tattgaagag gatggtgcca   360
ggcggtgcga gatggacac agcctccatg ctcgacgaag ccatccgtta taccaagttc   420
ttgaaacggc aggtgaagct tcttcagcct cactctcagc ttggagctcc tatgtctgac   480
ccctcttgcc tttgttatta ccacaactcc caaacctaa                         519
```

<210> SEQ ID NO 10
<211> LENGTH: 172
<212> TYPE: PRT
<213> ORGANISM: Thlaspi arvense

<400> SEQUENCE: 10

```
Met Asn Trp Asn Lys Pro Asn Asp Leu Ile Thr Gln Glu Tyr Pro Phe
 1               5                  10                  15

Leu His Asp Pro His Leu Met Ile Asp Pro Pro Glu Thr Leu Ser
            20                  25                  30

His Phe Gln Pro Pro Pro Thr Leu Phe Ser Gly His Gly Gly Glu Glu
         35                  40                  45
```

Glu Glu Glu Glu Asp Asn Glu Glu Glu Met Asp Ala Met Lys Glu
             50                  55                  60

Met Gln Tyr Thr Ile Ala Ala Met Gln Pro Val Asp Ile Asp Pro Ala
 65                  70                  75                  80

Thr Val Pro Lys Pro Asn Arg Arg Asn Val Arg Val Ser Asp Asp Thr
                 85                  90                  95

Gln Thr Val Val Ala Arg Arg Arg Glu Lys Ile Ser Glu Lys Ile
            100                 105                 110

Arg Ile Leu Lys Arg Met Val Pro Gly Gly Ala Lys Met Asp Thr Ala
            115                 120                 125

Ser Met Leu Asp Glu Ala Ile Arg Tyr Thr Lys Phe Leu Lys Arg Gln
    130                 135                 140

Val Lys Leu Leu Gln Pro His Ser Gln Leu Gly Ala Pro Met Ser Asp
145                 150                 155                 160

Pro Ser Cys Leu Cys Tyr Tyr His Asn Ser Gln Thr
                165                 170

<210> SEQ ID NO 11
<211> LENGTH: 519
<212> TYPE: DNA
<213> ORGANISM: Artificial Sequence
<220> FEATURE:
<223> OTHER INFORMATION: modified pennycress IND nucleotide sequence

<400> SEQUENCE: 11
atgaattgga acaaacctaa tgatctcatc acacaagaat accccttcct ccacgatcct     60
catctcatga tagatccacc tcccgaaacc ctaagtcatt tccagccccc gccgacactt    120
ttctccggtc acggagggga ggaagaagaa gaagaagata tgaagagga agagatggat     180 gcgatgaagg agatgcagta cacgatcgct gccatgcagc ccgtggacat cgatccagcc    240
accgtttcta aaccgaaccg ccgtaacgta agggtaagcg acgacactca gacggtggtg    300
gctcgtcggc gtcgagaaaa gataagcgag aagatccgaa tattgaagag gatggtgcca    360
ggcggtgcga agatggacac agcctccatg ctcgacgaag ccatccgtta ccaagttc     420 ttgaaacggc aggtgaagct tcttcagcct cactctcagc ttggagctcc tatgtctgac    480
ccctcttgcc tttgttatta ccacaactcc caaacctaa                          519

<210> SEQ ID NO 12
<211> LENGTH: 172
<212> TYPE: PRT
<213> ORGANISM: Artificial Sequence
<220> FEATURE:
<223> OTHER INFORMATION: modified pennycress IND polypeptide sequence

<400> SEQUENCE: 12

Met Asn Trp Asn Lys Pro Asn Asp Leu Ile Thr Gln Glu Tyr Pro Phe
 1               5                  10                  15

Leu His Asp Pro His Leu Met Ile Asp Pro Pro Glu Thr Leu Ser
            20                  25                  30

His Phe Gln Pro Pro Pro Thr Leu Phe Ser Gly His Gly Gly Glu Glu
        35                  40                  45

Glu Glu Glu Glu Asp Asn Glu Glu Glu Met Asp Ala Met Lys Glu
             50                  55                  60

Met Gln Tyr Thr Ile Ala Ala Met Gln Pro Val Asp Ile Asp Pro Ala
 65                  70                  75                  80

Thr Val Ser Lys Pro Asn Arg Arg Asn Val Arg Val Ser Asp Asp Thr

```
                    85                  90                  95

Gln Thr Val Val Ala Arg Arg Arg Glu Lys Ile Ser Glu Lys Ile
            100                 105                 110

Arg Ile Leu Lys Arg Met Val Pro Gly Gly Ala Lys Met Asp Thr Ala
        115                 120                 125

Ser Met Leu Asp Glu Ala Ile Arg Tyr Thr Lys Phe Leu Lys Arg Gln
    130                 135                 140

Val Lys Leu Leu Gln Pro His Ser Gln Leu Gly Ala Pro Met Ser Asp
145                 150                 155                 160

Pro Ser Cys Leu Cys Tyr Tyr His Asn Ser Gln Thr
                165                 170

<210> SEQ ID NO 13
<211> LENGTH: 519
<212> TYPE: DNA
<213> ORGANISM: Artificial Sequence
<220> FEATURE:
<223> OTHER INFORMATION: modified pennycress IND nucleotide sequence

<400> SEQUENCE: 13
atgaattgga acaaacctaa tgatctcatc acacaagaat accccttttct ccacgatcct    60 catctcatga tagatccacc tcccgaaacc ctaagtcatt tccagccccc gccgacactt   120
ttctccggtc acgagggga ggaagaagaa gaagaagata tgaagagga agagatggat    180 gcgatgaagg agatgcagta cacgatcgct gccatgcagc ccgtggacat cgatccagcc   240
accgttccta aaccgaacca ccgtaacgta agggtaagcg acgacactca gacggtggtg   300
gctcgtcggc gtcgagaaaa gataagcgag aagatccgaa tattgaagag gatggtgcca   360
ggcggtgcga agatggacac agcctccatg ctcgacgaag ccatccgtta taccaagttc   420
ttgaaacggc aggtgaagct tcttcagcct cactctcagc ttggagctcc tatgtctgac   480
ccctcttgcc tttgttatta ccacaactcc caaacctaa                         519

<210> SEQ ID NO 14
<211> LENGTH: 172
<212> TYPE: PRT
<213> ORGANISM: Artificial Sequence
<220> FEATURE:
<223> OTHER INFORMATION: modified pennycress IND polypeptide sequence

<400> SEQUENCE: 14

Met Asn Trp Asn Lys Pro Asn Asp Leu Ile Thr Gln Glu Tyr Pro Phe
1               5                   10                  15

Leu His Asp Pro His Leu Met Ile Asp Pro Pro Glu Thr Leu Ser
            20                  25                  30

His Phe Gln Pro Pro Thr Leu Phe Ser Gly His Gly Gly Glu Glu
        35                  40                  45

Glu Glu Glu Glu Asp Asn Glu Glu Glu Met Asp Ala Met Lys Glu
    50                  55                  60

Met Gln Tyr Thr Ile Ala Ala Met Gln Pro Val Asp Ile Asp Pro Ala
65                  70                  75                  80

Thr Val Pro Lys Pro Asn His Arg Asn Val Arg Val Ser Asp Asp Thr
                85                  90                  95

Gln Thr Val Val Ala Arg Arg Arg Glu Lys Ile Ser Glu Lys Ile
            100                 105                 110

Arg Ile Leu Lys Arg Met Val Pro Gly Gly Ala Lys Met Asp Thr Ala
        115                 120                 125
```

```
Ser Met Leu Asp Glu Ala Ile Arg Tyr Thr Lys Phe Leu Lys Arg Gln
        130                 135                 140

Val Lys Leu Leu Gln Pro His Ser Gln Leu Gly Ala Pro Met Ser Asp
145                 150                 155                 160

Pro Ser Cys Leu Cys Tyr Tyr His Asn Ser Gln Thr
                165                 170

<210> SEQ ID NO 15
<211> LENGTH: 519
<212> TYPE: DNA
<213> ORGANISM: Artificial Sequence
<220> FEATURE:
<223> OTHER INFORMATION: modified pennycress IND nucleotide sequence

<400> SEQUENCE: 15
atgaattgga acaaacctaa tgatctcatc acacaagaat acccctttct ccacgatcct      60
catctcatga tagatccacc tcccgaaacc ctaagtcatt tccagccccc gccgacactt     120
ttctccggtc acgaggggga ggaagaagaa gaagaagata tgaagagga agagatggat      180 gcgatgaagg agatgcagta cacgatcgct gccatgcagc ccgtggacat cgatccagcc     240
accgttccta aaccgaaccg ccgtaacgta agggtaagcg acgacactca gacggtggtg     300
actcgtcggc gtcgagaaaa gataagcgag aagatccgaa tattgaagag gatggtgcca     360
ggcggtgcga gatggacac agcctccatg ctcgacgaag ccatccgtta taccaagttc      420
ttgaaacggc aggtgaagct tcttcagcct cactctcagc ttggagctcc tatgtctgac     480
ccctcttgcc tttgttatta ccacaactcc caaacctaa                            519

<210> SEQ ID NO 16
<211> LENGTH: 172
<212> TYPE: PRT
<213> ORGANISM: Artificial Sequence
<220> FEATURE:
<223> OTHER INFORMATION: modified pennycress IND polypeptide sequence

<400> SEQUENCE: 16

Met Asn Trp Asn Lys Pro Asn Asp Leu Ile Thr Gln Glu Tyr Pro Phe
1               5                   10                  15

Leu His Asp Pro His Leu Met Ile Asp Pro Pro Glu Thr Leu Ser
            20                  25                  30

His Phe Gln Pro Pro Thr Leu Phe Ser Gly His Gly Gly Glu Glu
        35                  40                  45

Glu Glu Glu Glu Asp Asn Glu Glu Glu Glu Met Asp Ala Met Lys Glu
        50                  55                  60

Met Gln Tyr Thr Ile Ala Ala Met Gln Pro Val Asp Ile Asp Pro Ala
65                  70                  75                  80

Thr Val Pro Lys Pro Asn Arg Arg Asn Val Arg Val Ser Asp Asp Thr
                85                  90                  95

Gln Thr Val Val Thr Arg Arg Arg Glu Lys Ile Ser Glu Lys Ile
            100                 105                 110

Arg Ile Leu Lys Arg Met Val Pro Gly Gly Ala Lys Met Asp Thr Ala
        115                 120                 125

Ser Met Leu Asp Glu Ala Ile Arg Tyr Thr Lys Phe Leu Lys Arg Gln
        130                 135                 140

Val Lys Leu Leu Gln Pro His Ser Gln Leu Gly Ala Pro Met Ser Asp
145                 150                 155                 160

Pro Ser Cys Leu Cys Tyr Tyr His Asn Ser Gln Thr
                165                 170
```

<210> SEQ ID NO 17
<211> LENGTH: 747
<212> TYPE: DNA
<213> ORGANISM: Thlaspi arvense

<400> SEQUENCE: 17

```
atggaagagg gtgggagtag tcacgacgca gagagtagca agaagatagg gagagggaag      60
atagagataa agaggataga gaacacaacg aatcgtcaag taactttctg caaacgacgc     120
aatggtcttc tcaagaaagc ttatgagctc tctgtcttgt gtgatgccga agttgccctc     180
gttatcttct ccactcgtgg ccgtctctat gagtatgcca acaacagtgt gaagggtaca     240
attgaaaggt acaagaaagc ttgttcagat gccgtcaatc cccctccgt caccgaagct      300
aatactcagt actatcagca agaagcctct aagcttcgga ggcagattcg agacattcag     360
aactcaaaca ggcatattgt tggggaatca cttggttcct tgaacttcaa ggaactcaaa     420
aacctcgaag acgccttga aaaggaatt agccgcgtcc gatccaagaa gaatgagttg      480
ttagtggcag agattgagta tatgcagaag agggaaatgg atttgcaaca cgataacatg     540
tacctgcgag ctaagatatc cgaaggcgtg aggttgaatc cggaacagca cggatcgagt     600
gtgatacaag aacagcgat ttacgaatcc ggtgtgtctt ctcatgatca gtcgcagcat      660
tataatcgga actatattcc agtgaacctt cttgaaccaa atcagcaatt ctccggtcaa     720
gaccaacctc ctcttcaact tgtttaa                                         747
```

<210> SEQ ID NO 18
<211> LENGTH: 248
<212> TYPE: PRT
<213> ORGANISM: Thlaspi arvense

<400> SEQUENCE: 18

```
Met Glu Glu Gly Gly Ser Ser His Asp Ala Glu Ser Ser Lys Lys Ile
1               5                   10                  15

Gly Arg Gly Lys Ile Glu Ile Lys Arg Ile Glu Asn Thr Thr Asn Arg
            20                  25                  30

Gln Val Thr Phe Cys Lys Arg Arg Asn Gly Leu Leu Lys Lys Ala Tyr
        35                  40                  45

Glu Leu Ser Val Leu Cys Asp Ala Glu Val Ala Leu Val Ile Phe Ser
    50                  55                  60

Thr Arg Gly Arg Leu Tyr Glu Tyr Ala Asn Asn Ser Val Lys Gly Thr
65                  70                  75                  80

Ile Glu Arg Tyr Lys Lys Ala Cys Ser Asp Ala Val Asn Pro Pro Ser
                85                  90                  95

Val Thr Glu Ala Asn Thr Gln Tyr Tyr Gln Gln Glu Ala Ser Lys Leu
            100                 105                 110

Arg Arg Gln Ile Arg Asp Ile Gln Asn Ser Asn Arg His Ile Val Gly
        115                 120                 125

Glu Ser Leu Gly Ser Leu Asn Phe Lys Glu Leu Lys Asn Leu Glu Gly
    130                 135                 140

Arg Leu Glu Lys Gly Ile Ser Arg Val Arg Ser Lys Lys Asn Glu Leu
145                 150                 155                 160

Leu Val Ala Glu Ile Glu Tyr Met Gln Lys Arg Glu Met Asp Leu Gln
                165                 170                 175

His Asp Asn Met Tyr Leu Arg Ala Lys Ile Ser Glu Gly Val Arg Leu
            180                 185                 190
```

```
Asn Pro Glu Gln His Gly Ser Ser Val Ile Gln Gly Thr Ala Ile Tyr
            195                 200                 205

Glu Ser Gly Val Ser Ser His Asp Gln Ser Gln His Tyr Asn Arg Asn
        210                 215                 220

Tyr Ile Pro Val Asn Leu Leu Glu Pro Asn Gln Gln Phe Ser Gly Gln
225                 230                 235                 240

Asp Gln Pro Pro Leu Gln Leu Val
                245

<210> SEQ ID NO 19
<211> LENGTH: 747
<212> TYPE: DNA
<213> ORGANISM: Artificial Sequence
<220> FEATURE:
<223> OTHER INFORMATION: modified pennycress SHP1 nucleotide sequence

<400> SEQUENCE: 19
atggaagagg gtgggaatag tcacgacgca gagagtagca agaagatagg gagagggaag      60
atagagataa agaggataga gaacacaacg aatcgtcaag taactttctg caaacgacgc     120
aatggtcttc tcaagaaagc ttatgagctc tctgtcttgt gtgatgccga agttgccctc     180
gttatcttct ccactcgtgg ccgtctctat gagtatgcca acaacagtgt gaagggtaca     240
attgaaaggt acaagaaagc ttgttcagat gccgtcaatc cccctccgt caccgaagct      300 aatactcagt actatcagca agaagcctct aagcttcgga ggcagattcg agacattcag     360
aactcaaaca ggcatattgt tggggaatca cttggttcct tgaacttcaa ggaactcaaa     420
aacctcgaag gacgccttga aaaggaatt agccgcgtcc gatccaagaa gaatgagttg      480
ttagtggcag agattgagta tatgcagaag agggaaatgg atttgcaaca cgataacatg     540
tacctgcgag ctaagatatc cgaaggcgtg aggttgaatc cggaacagca cggatcgagt     600
gtgatacaag gaacagcgat ttacgaatcc ggtgtgtctt ctcatgatca gtcgcagcat     660
tataatcgga actatattcc agtgaacctt cttgaaccaa atcagcaatt ctccggtcaa     720
gaccaacctc ctcttcaact tgttaa                                           747

<210> SEQ ID NO 20
<211> LENGTH: 248
<212> TYPE: PRT
<213> ORGANISM: Artificial Sequence
<220> FEATURE:
<223> OTHER INFORMATION: modified pennycress SHP1 polypeptide sequence

<400> SEQUENCE: 20

Met Glu Glu Gly Gly Asn Ser His Asp Ala Glu Ser Ser Lys Lys Ile
1               5                   10                  15

Gly Arg Gly Lys Ile Glu Ile Lys Arg Ile Glu Asn Thr Thr Asn Arg
            20                  25                  30

Gln Val Thr Phe Cys Lys Arg Arg Asn Gly Leu Leu Lys Lys Ala Tyr
        35                  40                  45

Glu Leu Ser Val Leu Cys Asp Ala Glu Val Ala Leu Val Ile Phe Ser
    50                  55                  60

Thr Arg Gly Arg Leu Tyr Glu Tyr Ala Asn Asn Ser Val Lys Gly Thr
65                  70                  75                  80

Ile Glu Arg Tyr Lys Lys Ala Cys Ser Asp Ala Val Asn Pro Pro Ser
                85                  90                  95

Val Thr Glu Ala Asn Thr Gln Tyr Tyr Gln Gln Glu Ala Ser Lys Leu
            100                 105                 110
```

```
Arg Arg Gln Ile Arg Asp Ile Gln Asn Ser Asn Arg His Ile Val Gly
        115                 120                 125

Glu Ser Leu Gly Ser Leu Asn Phe Lys Glu Leu Lys Asn Leu Glu Gly
        130                 135                 140

Arg Leu Glu Lys Gly Ile Ser Arg Val Arg Ser Lys Lys Asn Glu Leu
145                 150                 155                 160

Leu Val Ala Glu Ile Glu Tyr Met Gln Lys Arg Glu Met Asp Leu Gln
                165                 170                 175

His Asp Asn Met Tyr Leu Arg Ala Lys Ile Ser Glu Gly Val Arg Leu
            180                 185                 190

Asn Pro Glu Gln His Gly Ser Ser Val Ile Gln Gly Thr Ala Ile Tyr
        195                 200                 205

Glu Ser Gly Val Ser Ser His Asp Gln Ser Gln His Tyr Asn Arg Asn
        210                 215                 220

Tyr Ile Pro Val Asn Leu Leu Glu Pro Asn Gln Gln Phe Ser Gly Gln
225                 230                 235                 240

Asp Gln Pro Pro Leu Gln Leu Val
                245
```

<210> SEQ ID NO 21
<211> LENGTH: 741
<212> TYPE: DNA
<213> ORGANISM: Thlaspi arvense

<400> SEQUENCE: 21

```
atggagggtg gtgcgagtaa tgaagtagca gagagcagca agaagatagg gagagggaag     60
atagagataa agaggataga gaatactacg aatcgtcaag taactttctg caaacgacgc    120
aatggtttgc tcaagaaagc ttacgagctc tccgtcttgt gtgatgcgga ggttgctctc    180
gtcatattct ccactcgagg tcgtctctac gagtacgcca acaacagtgt aagaggaacg    240
atcgaaaggt acaagaaagc ttgctccgac gccgtgaatc ctccttccgt caccgaagct    300
aatactcagt attatcagca agagtcgtcg aagctacgga gacagattcg agacattcag    360
aatctgaaca gacacattct tggtgagtct cttggttcct tgaatctcaa ggaactaaag    420
aacctcgaag gtaggcttga aaaggcatc agtcgcgtcc gctccaagaa gcacgagatg    480
ttagttgcag atagagta catgcaaaaa agggaaatcg agctgcaaaa cgataacatg    540
tatctccgat ccaagattac ggaaagggca ggagtacagc agcaggaatc gagtgtgata    600
catcaaggaa cggtttacga gtcgggtgta tcgtcttctc atcagactga gcagtataac    660
cggagttata ttccggttaa tctgctcgaa ccaaatccga attcctccga ccaagaccaa    720
ccacctctcc aacttgtcta a                                               741
```

<210> SEQ ID NO 22
<211> LENGTH: 246
<212> TYPE: PRT
<213> ORGANISM: Thlaspi arvense

<400> SEQUENCE: 22

```
Met Glu Gly Gly Ala Ser Asn Glu Val Ala Glu Ser Ser Lys Lys Ile
1               5                   10                  15

Gly Arg Gly Lys Ile Glu Ile Lys Arg Ile Glu Asn Thr Thr Asn Arg
                20                  25                  30

Gln Val Thr Phe Cys Lys Arg Arg Asn Gly Leu Leu Lys Lys Ala Tyr
            35                  40                  45

Glu Leu Ser Val Leu Cys Asp Ala Glu Val Ala Leu Val Ile Phe Ser
```

```
                    50                  55                  60
Thr Arg Gly Arg Leu Tyr Glu Tyr Ala Asn Asn Ser Val Arg Gly Thr
 65                  70                  75                  80

Ile Glu Arg Tyr Lys Lys Ala Cys Ser Asp Ala Val Asn Pro Pro Ser
                 85                  90                  95

Val Thr Glu Ala Asn Thr Gln Tyr Tyr Gln Gln Glu Ser Ser Lys Leu
                100                 105                 110

Arg Arg Gln Ile Arg Asp Ile Gln Asn Leu Asn Arg His Ile Leu Gly
            115                 120                 125

Glu Ser Leu Gly Ser Leu Asn Leu Lys Glu Leu Lys Asn Leu Glu Gly
        130                 135                 140

Arg Leu Glu Lys Gly Ile Ser Arg Val Arg Ser Lys Lys His Glu Met
145                 150                 155                 160

Leu Val Ala Glu Ile Glu Tyr Met Gln Lys Arg Glu Ile Glu Leu Gln
                165                 170                 175

Asn Asp Asn Met Tyr Leu Arg Ser Lys Ile Thr Glu Arg Ala Gly Val
            180                 185                 190

Gln Gln Gln Glu Ser Ser Val Ile His Gln Gly Thr Val Tyr Glu Ser
        195                 200                 205

Gly Val Ser Ser Ser His Gln Thr Glu Gln Tyr Asn Arg Ser Tyr Ile
    210                 215                 220

Pro Val Asn Leu Leu Glu Pro Asn Pro Asn Ser Ser Asp Gln Asp Gln
225                 230                 235                 240

Pro Pro Leu Gln Leu Val
                245

<210> SEQ ID NO 23
<211> LENGTH: 741
<212> TYPE: DNA
<213> ORGANISM: Artificial Sequence
<220> FEATURE:
<223> OTHER INFORMATION: modified pennycress SHP2 nucleotide sequence

<400> SEQUENCE: 23
atggagggtg gtgcgagtaa tgaagtagca gagagcagca agaagatagg gagagggaag      60
atagagataa agaggataga gaatactacg aatcgtcaag taactttctg caaacgacgc     120
aatggtttgc tcaagaaagc ttacgagctc tccgtcttgt gtgatgcgga ggttactctc     180
gtcatattct ccactcgagg tcgtctctac gagtacgcca acaacagtgt aagaggaacg     240
atcgaaaggt acaagaaagc ttgctccgac gccgtgaatc ctccttccgt caccgaagct     300
aatactcagt attatcagca agagtcgtcg aagctacgga gacagattcg agacattcag     360
aatctgaaca gacacattct tggtgagtct cttggttcct tgaatctcaa ggaactaaag     420
aacctcgaag gtaggcttga gaaaggcatc agtcgcgtcc gctccaagaa gcacgagatg     480
ttagttgcag agatagagta catgcaaaaa agggaaatcg agctgcaaaa cgataacatg     540
tatctccgat ccaagattac ggaaagggca ggagtacagc agcaggaatc gagtgtgata     600
catcaaggaa cggtttacga gtcgggtgta tcgtcttctc atcagactga gcagtataac     660
cggagttata ttccggttaa tctgctcgaa ccaaatccga attcctccga ccaagaccaa     720
ccacctctcc aacttgtcta a                                                741

<210> SEQ ID NO 24
<211> LENGTH: 246
<212> TYPE: PRT
<213> ORGANISM: Artificial Sequence
```

<220> FEATURE:
<223> OTHER INFORMATION: modified pennycress SHP2 polypeptide sequence

<400> SEQUENCE: 24

| | | | | | | | | | | | | | | | |
|---|---|---|---|---|---|---|---|---|---|---|---|---|---|---|---|
| Met | Glu | Gly | Gly | Ala | Ser | Asn | Glu | Val | Ala | Glu | Ser | Lys | Lys | Ile | |
| 1 | | | | 5 | | | | | 10 | | | | | 15 | |
| Gly | Arg | Gly | Lys | Ile | Glu | Ile | Lys | Arg | Ile | Glu | Asn | Thr | Thr | Asn | Arg |
| | | | 20 | | | | | 25 | | | | | 30 | | |
| Gln | Val | Thr | Phe | Cys | Lys | Arg | Arg | Asn | Gly | Leu | Leu | Lys | Lys | Ala | Tyr |
| | | | 35 | | | | | 40 | | | | | 45 | | |
| Glu | Leu | Ser | Val | Leu | Cys | Asp | Ala | Glu | Val | Thr | Leu | Val | Ile | Phe | Ser |
| | | | 50 | | | | | 55 | | | | | 60 | | |
| Thr | Arg | Gly | Arg | Leu | Tyr | Glu | Tyr | Ala | Asn | Asn | Ser | Val | Arg | Gly | Thr |
| 65 | | | | | 70 | | | | | 75 | | | | | 80 |
| Ile | Glu | Arg | Tyr | Lys | Lys | Ala | Cys | Ser | Asp | Ala | Val | Asn | Pro | Pro | Ser |
| | | | | 85 | | | | | 90 | | | | | 95 | |
| Val | Thr | Glu | Ala | Asn | Thr | Gln | Tyr | Tyr | Gln | Gln | Glu | Ser | Ser | Lys | Leu |
| | | | 100 | | | | | 105 | | | | | 110 | | |
| Arg | Arg | Gln | Ile | Arg | Asp | Ile | Gln | Asn | Leu | Asn | Arg | His | Ile | Leu | Gly |
| | | 115 | | | | | 120 | | | | | 125 | | | |
| Glu | Ser | Leu | Gly | Ser | Leu | Asn | Leu | Lys | Glu | Leu | Lys | Asn | Leu | Glu | Gly |
| | 130 | | | | | 135 | | | | | 140 | | | | |
| Arg | Leu | Glu | Lys | Gly | Ile | Ser | Arg | Val | Arg | Ser | Lys | Lys | His | Glu | Met |
| 145 | | | | | 150 | | | | | 155 | | | | | 160 |
| Leu | Val | Ala | Glu | Ile | Glu | Tyr | Met | Gln | Lys | Arg | Glu | Ile | Glu | Leu | Gln |
| | | | | 165 | | | | | 170 | | | | | 175 | |
| Asn | Asp | Asn | Met | Tyr | Leu | Arg | Ser | Lys | Ile | Thr | Glu | Arg | Ala | Gly | Val |
| | | | 180 | | | | | 185 | | | | | 190 | | |
| Gln | Gln | Gln | Glu | Ser | Ser | Val | Ile | His | Gln | Gly | Thr | Val | Tyr | Glu | Ser |
| | | | 195 | | | | | 200 | | | | | 205 | | |
| Gly | Val | Ser | Ser | Ser | His | Gln | Thr | Glu | Gln | Tyr | Asn | Arg | Ser | Tyr | Ile |
| | | 210 | | | | | 215 | | | | | 220 | | | |
| Pro | Val | Asn | Leu | Leu | Glu | Pro | Asn | Pro | Asn | Ser | Ser | Asp | Gln | Asp | Gln |
| 225 | | | | | 230 | | | | | 235 | | | | | 240 |
| Pro | Pro | Leu | Gln | Leu | Val | | | | | | | | | | |
| | | | | 245 | | | | | | | | | | | |

<210> SEQ ID NO 25
<211> LENGTH: 1320
<212> TYPE: DNA
<213> ORGANISM: Thlaspi arvense

<400> SEQUENCE: 25

```
atgttacggg aatcagacgg tgagatgagc ttagagacga cgaactcgcc gattagcagc      60
ggaacagaga gctgcagcag tttcagccgg ttatctttcg acgcgccgcc gtcaaccacc     120
gcgattatcc ccgaggaaga gagccttctc tctattaaac cgcaccgatc ctccgatttc     180
gcatactcgg agatccgacg gcggcggaaa caaggcctca ccttccgaga ttttcgactc     240
atgcgtcgaa tcggcgccgg agacatcggg accgtgtact tgtgccgtct cgccggagac     300
gaagaagaga gccggagctc gtatttcgcg atgaaagtgg tggacaaaga agcgcttgcg     360
atgaagaaga gatgcacagc agcagagatg gagaagacga ttctgaagat gcttgaccat     420
ccgttttttgc cgactcttta cgccgagttt gacgcatcgc atttctcttg catcgtcatg     480
gagtattgct ccggcggaga tttgcactcc ctccgtcaca aacagctcaa ccgcagattc     540
```

```
tcccttttcct ccgccagatt ttacgcggct gaagttcttg tggcgctgga atatctacac    600
atgctgggta tcatctacag agatctgaag cctgaaaata tcttagttag atcggacggt    660
cacattatgc tctctgactt tgatctctcc ttatgctccg actcaatcgc agccgttgaa    720
tcctccacat cttcaccgga gaatcaaccc cgttcttccc ggcgccgact cactcgactc    780
tctaggatct tccaccgagt cttgcggtcc aaaaaggttc agacgctcga accgaaccgt    840
ctctttgttg ccgaaccggt caccgctcgg tccggttcgt tgttggtac gcatgaatac     900 gtggcaccag aagtcgcctc aggtgggtct catggaaatg ccgttgactg gtgggccttc    960
ggagtattcc tctacgagat gatctacggc cggactccat cgccgcgcc gacgaatgac    1020 gtcatccttc gtaacatcgt gaagagaccg ttgagtttcc cgaccgattc gccgtcgacg    1080
atgttcgagc ttcacgcgcg gggattgatc tccgggttgc tcaacaagga tccgaacaaa    1140
cgactcgggt cacggcgagg cgcggcggag gttaaagtgc atccgttttt caaaggtcta    1200
aactttgcgc tcattcgtac attaactccg ccggagattc cctccgaggt caggataccg    1260
aagaaatcgt cgacgttcgg tggtagagct agtaaaccag cggcgttcga ttacttttga    1320
```

<210> SEQ ID NO 26
<211> LENGTH: 439
<212> TYPE: PRT
<213> ORGANISM: Thlaspi arvense

<400> SEQUENCE: 26

Met Leu Arg Glu Ser Asp Gly Glu Met Ser Leu Glu Thr Thr Asn Ser
1               5                   10                  15

Pro Ile Ser Ser Gly Thr Glu Ser Cys Ser Ser Phe Ser Arg Leu Ser
            20                  25                  30

Phe Asp Ala Pro Pro Ser Thr Thr Ala Ile Ile Pro Glu Glu Glu Ser
        35                  40                  45

Leu Leu Ser Ile Lys Pro His Arg Ser Asp Phe Ala Tyr Ser Glu
    50                  55                  60

Ile Arg Arg Arg Arg Lys Gln Gly Leu Thr Phe Arg Asp Phe Arg Leu
65                  70                  75                  80

Met Arg Arg Ile Gly Ala Gly Asp Ile Gly Thr Val Tyr Leu Cys Arg
                85                  90                  95

Leu Ala Gly Asp Glu Glu Glu Ser Arg Ser Ser Tyr Phe Ala Met Lys
            100                 105                 110

Val Val Asp Lys Glu Ala Leu Ala Met Lys Lys Met His Arg Ala
        115                 120                 125

Glu Met Glu Lys Thr Ile Leu Lys Met Leu Asp His Pro Phe Leu Pro
130                 135                 140

Thr Leu Tyr Ala Glu Phe Asp Ala Ser His Phe Ser Cys Ile Val Met
145                 150                 155                 160

Glu Tyr Cys Ser Gly Gly Asp Leu His Ser Leu Arg His Lys Gln Leu
                165                 170                 175

Asn Arg Arg Phe Ser Leu Ser Ser Ala Arg Phe Tyr Ala Ala Glu Val
            180                 185                 190

Leu Val Ala Leu Glu Tyr Leu His Met Leu Gly Ile Ile Tyr Arg Asp
        195                 200                 205

Leu Lys Pro Glu Asn Ile Leu Val Arg Ser Asp Gly His Ile Met Leu
    210                 215                 220

Ser Asp Phe Asp Leu Ser Leu Cys Ser Asp Ser Ile Ala Ala Val Glu
225                 230                 235                 240

```
Ser Ser Thr Ser Ser Pro Glu Asn Gln Pro Arg Ser Ser Arg Arg Arg
            245                 250                 255

Leu Thr Arg Leu Ser Arg Ile Phe His Arg Val Leu Arg Ser Lys Lys
        260                 265                 270

Val Gln Thr Leu Glu Pro Asn Arg Leu Phe Val Ala Glu Pro Val Thr
            275                 280                 285

Ala Arg Ser Gly Ser Phe Val Gly Thr His Glu Tyr Val Ala Pro Glu
        290                 295                 300

Val Ala Ser Gly Gly Ser His Gly Asn Ala Val Asp Trp Trp Ala Phe
305                 310                 315                 320

Gly Val Phe Leu Tyr Glu Met Ile Tyr Gly Arg Thr Pro Phe Ala Ala
                325                 330                 335

Pro Thr Asn Asp Val Ile Leu Arg Asn Ile Val Lys Arg Pro Leu Ser
            340                 345                 350

Phe Pro Thr Asp Ser Pro Ser Thr Met Phe Glu Leu His Ala Arg Gly
        355                 360                 365

Leu Ile Ser Gly Leu Leu Asn Lys Asp Pro Asn Lys Arg Leu Gly Ser
370                 375                 380

Arg Arg Gly Ala Ala Glu Val Lys Val His Pro Phe Phe Lys Gly Leu
385                 390                 395                 400

Asn Phe Ala Leu Ile Arg Thr Leu Thr Pro Pro Glu Ile Pro Ser Glu
                405                 410                 415

Val Arg Ile Pro Lys Lys Ser Ser Thr Phe Gly Gly Arg Ala Ser Lys
            420                 425                 430

Pro Ala Ala Phe Asp Tyr Phe
        435
```

<210> SEQ ID NO 27
<211> LENGTH: 1320
<212> TYPE: DNA
<213> ORGANISM: Artificial Sequence
<220> FEATURE:
<223> OTHER INFORMATION: modified pennycress PID nucleotide sequence

<400> SEQUENCE: 27

```
atgttacggg aatcagacgg tgagatgagc ttagagacga cgaactcgcc gattagcagc    60
ggaacagaga gctgcagcag tttcagccgg ttatctttcg acgcgccgcc gtcaaccacc   120
gcgattatcc ccgaggaaga gagccttctc tctattaaac cgcaccgatc ctccgatttc   180
gcatactcgg agatccgacg gcggcggaaa caaggcctca ccttccgaga ttttcgactc   240
atgcgtcgaa tcggcgccgg agacatcggg accgtgtact gtgccgtctc gccggagac   300 gaagaagaga gccggagctc gtatttcgcg atgaaagtgg tggacaaaga gcgcttgcg   360 atgaagaaga agatgcacag agcagagatg gagaagacga ttctgaagat gcttgaccat   420 ccgttttgc cgactcttta cgccgagttt gacgcatcgc atttctctta catcgtcatg   480
gagtattgct ccggcggaga tttgcactcc ctccgtcaca aacagctcaa ccgcagattc   540
tccctttcct ccgccagatt ttacgcggct gaagttcttg tggcgctgga atatctacac   600
atgctgggta tcatctacag agatctgaag cctgaaaata tcttagttag atcggacggt   660
cacattatgc tctctgactt tgatctctcc ttatgctccg actcaatcgc agccgttgaa   720
tcctccacat cttcaccgga gaatcaaccc cgttcttccc ggcgccgact cactcgactc   780
tctaggatct tccaccgagt cttgcggtcc aaaaaggttc agacgctcga accgaaccgt   840
ctctttgttg ccgaaccggt caccgctcgg tccggttcgt tgttggtac gcatgaatac   900
```

-continued

```
gtggcaccag aagtcgcctc aggtgggtct catggaaatg ccgttgactg gtgggccttc    960
ggagtattcc tctacgagat gatctacggc cggactccat cgccgcgcc gacgaatgac    1020 gtcatccttc gtaacatcgt gaagagaccg ttgagtttcc cgaccgattc gccgtcgacg    1080
atgttcgagc ttcacgcgcg gggattgatc tccggggttgc tcaacaagga tccgaacaaa   1140
cgactcgggt cacggcgagg cgcggcggag gttaaagtgc atccgttttt caaaggtcta    1200
aactttgcgc tcattcgtac attaactccg ccggagattc cctccgaggt caggataccg    1260
aagaaatcgt cgacgttcgg tggtagagct agtaaaccag cggcgttcga ttactttga    1320
```

```
<210> SEQ ID NO 28
<211> LENGTH: 439
<212> TYPE: PRT
<213> ORGANISM: Artificial Sequence
<220> FEATURE:
<223> OTHER INFORMATION: modified pennycress PID polypeptide sequence

<400> SEQUENCE: 28

Met Leu Arg Glu Ser Asp Gly Glu Met Ser Leu Glu Thr Thr Asn Ser
1               5                   10                  15

Pro Ile Ser Ser Gly Thr Glu Ser Cys Ser Ser Phe Ser Arg Leu Ser
            20                  25                  30

Phe Asp Ala Pro Pro Ser Thr Thr Ala Ile Ile Pro Glu Glu Glu Ser
        35                  40                  45

Leu Leu Ser Ile Lys Pro His Arg Ser Ser Asp Phe Ala Tyr Ser Glu
    50                  55                  60

Ile Arg Arg Arg Lys Gln Gly Leu Thr Phe Arg Asp Phe Arg Leu
65                  70                  75                  80

Met Arg Arg Ile Gly Ala Gly Asp Ile Gly Thr Val Tyr Leu Cys Arg
                85                  90                  95

Leu Ala Gly Asp Glu Glu Ser Arg Ser Ser Tyr Phe Ala Met Lys
            100                 105                 110

Val Val Asp Lys Glu Ala Leu Ala Met Lys Lys Met His Arg Ala
        115                 120                 125

Glu Met Glu Lys Thr Ile Leu Lys Met Leu Asp His Pro Phe Leu Pro
    130                 135                 140

Thr Leu Tyr Ala Glu Phe Asp Ala Ser His Phe Ser Tyr Ile Val Met
145                 150                 155                 160

Glu Tyr Cys Ser Gly Gly Asp Leu His Ser Leu Arg His Lys Gln Leu
                165                 170                 175

Asn Arg Arg Phe Ser Leu Ser Ser Ala Arg Phe Tyr Ala Ala Glu Val
            180                 185                 190

Leu Val Ala Leu Glu Tyr Leu His Met Leu Gly Ile Ile Tyr Arg Asp
        195                 200                 205

Leu Lys Pro Glu Asn Ile Leu Val Arg Ser Asp Gly His Ile Met Leu
    210                 215                 220

Ser Asp Phe Asp Leu Ser Leu Cys Ser Asp Ser Ile Ala Ala Val Glu
225                 230                 235                 240

Ser Ser Thr Ser Ser Pro Glu Asn Gln Pro Arg Ser Ser Arg Arg Arg
                245                 250                 255

Leu Thr Arg Leu Ser Arg Ile Phe His Arg Val Leu Arg Ser Lys Lys
            260                 265                 270

Val Gln Thr Leu Glu Pro Asn Arg Leu Phe Val Ala Glu Pro Val Thr
        275                 280                 285

Ala Arg Ser Gly Ser Phe Val Gly Thr His Glu Tyr Val Ala Pro Glu
```

```
            290                 295                 300
Val Ala Ser Gly Gly Ser His Gly Asn Ala Val Asp Trp Trp Ala Phe
305                 310                 315                 320

Gly Val Phe Leu Tyr Glu Met Ile Tyr Gly Arg Thr Pro Phe Ala Ala
                325                 330                 335

Pro Thr Asn Asp Val Ile Leu Arg Asn Ile Val Lys Arg Pro Leu Ser
                340                 345                 350

Phe Pro Thr Asp Ser Pro Ser Thr Met Phe Glu Leu His Ala Arg Gly
            355                 360                 365

Leu Ile Ser Gly Leu Leu Asn Lys Asp Pro Asn Lys Arg Leu Gly Ser
        370                 375                 380

Arg Arg Gly Ala Ala Glu Val Lys Val His Pro Phe Phe Lys Gly Leu
385                 390                 395                 400

Asn Phe Ala Leu Ile Arg Thr Leu Thr Pro Pro Glu Ile Pro Ser Glu
                405                 410                 415

Val Arg Ile Pro Lys Lys Ser Ser Thr Phe Gly Gly Arg Ala Ser Lys
                420                 425                 430

Pro Ala Ala Phe Asp Tyr Phe
        435

<210> SEQ ID NO 29
<211> LENGTH: 1311
<212> TYPE: DNA
<213> ORGANISM: Thlaspi arvense

<400> SEQUENCE: 29
atggctcgtc gtttcggact tcttgctatc ttcttatgtg ttcttttgat gctctcgtgg     60
tgcgaagctt tgagtagcaa cgttgatgat ggatatggtc atgaagatgg aagcttcgaa    120
tccgatagct tactcaaact taagaacgac gacgacgacg ttcttacctt gaaaagctcc    180
gataaaacca cttccgaatc atcaactgtt agtgttaccg atttcggtgc taaaggagat    240
ggggaaaacg atgatactca ggccttcaag aaagcatgga gaaagcatg ttcaacaaag     300 ggagttacta gtttcttaat tcctaaagga aagacttatc tccttaagtc tactcgattc    360
agaggcccat gcaaatcttt acgtaacttt cagatcctag gcactttatc agcatctaca    420
aaacgatctg attataagaa tgacagaaac cattggcttg tcttggagga cgttaacaat    480
ctatcactgg atggcggctc gacgggaatt attgatggca acggaaaaat ctggtggcaa    540
aattcatgca aaatcgacca atctaagcca tgcacaaaag ccccaacggc tcttactttc    600
tacaacttaa agaatttgaa tgtgaagaat ctgagagtga aaatgcgca gcagattcag     660 atttcgattg agaaatgcaa caatgttaac gtcaacaatg tcgagatcac tgctcctgac    720
gatagtccca caccgatgg tattcacatc actaatacac aaaacattcg aatctccaat    780
tcagacattg gcacaggtga tgattgcata tccattgagg atggatccca aaatgttcaa    840
atcaatgatt taacttgcgg ccccggtcac gggatcagca ttgggagttt ggggatgac     900 aattcgaaag cttatgtctc ggggattaat gtagatggtg ctaagctctc ttctactgat    960
aatggagtta gaattaaaac ttaccaggga ggatcaggaa ctgccaagaa cattaaattt   1020 caaatattc gtatggaaaa tgtcaagaat ccaatcataa tcgaccagaa ctactgcgac   1080
aaggacaaat gcgaagaaca agaatccgcg gtgcaagtaa acaatgtggt gtaccggaac   1140
ataaccggta cgagcgcaac ggatgtggcg ataatgttta attgcagtga gaaatatcca   1200
tgccaaggga ttgtgcttga gaacgtgaat atcgaaggag gaacagcttc ttgcaaaaat   1260
```

-continued

```
gccaatgtta aggatcaagg cactgtatct cctcagtgct cttccacttg a         1311
```

<210> SEQ ID NO 30
<211> LENGTH: 436
<212> TYPE: PRT
<213> ORGANISM: Thlaspi arvense

<400> SEQUENCE: 30

| Met | Ala | Arg | Arg | Phe | Gly | Leu | Leu | Ala | Ile | Phe | Leu | Cys | Val | Leu | Leu |
|---|---|---|---|---|---|---|---|---|---|---|---|---|---|---|---|
| 1 | | | | 5 | | | | | 10 | | | | | 15 | |

Met Leu Ser Trp Cys Glu Ala Leu Ser Ser Asn Val Asp Asp Gly Tyr
                20                  25                  30

Gly His Glu Asp Gly Ser Phe Ser Asp Ser Leu Leu Lys Leu Lys
            35                  40                  45

Asn Asp Asp Asp Val Leu Thr Leu Lys Ser Asp Lys Thr Thr
 50                  55                  60

Ser Glu Ser Ser Thr Val Ser Val Thr Asp Phe Gly Ala Lys Gly Asp
 65                  70                  75                  80

Gly Glu Asn Asp Asp Thr Gln Ala Phe Lys Lys Ala Trp Lys Lys Ala
                85                  90                  95

Cys Ser Thr Lys Gly Val Thr Ser Phe Leu Ile Pro Lys Gly Lys Thr
            100                 105                 110

Tyr Leu Leu Lys Ser Thr Arg Phe Arg Gly Pro Cys Lys Ser Leu Arg
        115                 120                 125

Asn Phe Gln Ile Leu Gly Thr Leu Ser Ala Ser Thr Lys Arg Ser Asp
130                 135                 140

Tyr Lys Asn Asp Arg Asn His Trp Leu Val Leu Glu Asp Val Asn Asn
145                 150                 155                 160

Leu Ser Leu Asp Gly Gly Ser Thr Gly Ile Ile Asp Gly Asn Gly Lys
                165                 170                 175

Ile Trp Trp Gln Asn Ser Cys Lys Ile Asp Gln Ser Lys Pro Cys Thr
            180                 185                 190

Lys Ala Pro Thr Ala Leu Thr Phe Tyr Asn Leu Lys Asn Leu Asn Val
        195                 200                 205

Lys Asn Leu Arg Val Arg Asn Ala Gln Gln Ile Gln Ile Ser Ile Glu
210                 215                 220

Lys Cys Asn Asn Val Asn Val Asn Asn Val Glu Ile Thr Ala Pro Asp
225                 230                 235                 240

Asp Ser Pro Asn Thr Asp Gly Ile His Ile Thr Asn Thr Gln Asn Ile
                245                 250                 255

Arg Ile Ser Asn Ser Asp Ile Gly Thr Gly Asp Cys Ile Ser Ile
            260                 265                 270

Glu Asp Gly Ser Gln Asn Val Gln Ile Asn Asp Leu Thr Cys Gly Pro
        275                 280                 285

Gly His Gly Ile Ser Ile Gly Ser Leu Gly Asp Asp Asn Ser Lys Ala
 290                 295                 300

Tyr Val Ser Gly Ile Asn Val Asp Gly Ala Lys Leu Ser Ser Thr Asp
305                 310                 315                 320

Asn Gly Val Arg Ile Lys Thr Tyr Gln Gly Gly Ser Gly Thr Ala Lys
                325                 330                 335

Asn Ile Lys Phe Gln Asn Ile Arg Met Glu Asn Val Lys Asn Pro Ile
            340                 345                 350

Ile Ile Asp Gln Asn Tyr Cys Asp Lys Asp Lys Cys Glu Glu Gln Glu
        355                 360                 365

Ser Ala Val Gln Val Asn Asn Val Val Tyr Arg Asn Ile Thr Gly Thr
370                 375                 380

Ser Ala Thr Asp Val Ala Ile Met Phe Asn Cys Ser Glu Lys Tyr Pro
385                 390                 395                 400

Cys Gln Gly Ile Val Leu Glu Asn Val Asn Ile Glu Gly Gly Thr Ala
                405                 410                 415

Ser Cys Lys Asn Ala Asn Val Lys Asp Gln Gly Thr Val Ser Pro Gln
            420                 425                 430

Cys Ser Ser Thr
        435

<210> SEQ ID NO 31
<211> LENGTH: 1311
<212> TYPE: DNA
<213> ORGANISM: Artificial Sequence
<220> FEATURE:
<223> OTHER INFORMATION: modified pennycress ADPG1 nucleotide sequence

<400> SEQUENCE: 31
atggctcgtc gtttcggact tcttgctatc ttcttatgtg ttcttttgat gctctcgtgg      60
tgcgaagctt tgagtagcaa cgttgatgat ggatatggtc atgaagatgg aagcttcgaa     120
tccgatagct tactcaaact taagaacgac gacgacgacg ttcttacctt gaaaagctcc     180
gataaaacca cttccgaatc atcaactgtt agtgttaccg atttcggtgc taaaggagat     240
ggggaaaacg atgatactca ggccttcaag aaagcatgga gaaagcatg ttcaacaaag      300 ggagttacta gtttcttaat tcctaaagga aagacttatc tccttaagtc tactcgattc     360
agaggcccat gcaaatcttt acgtaacttt cagatcctag gcactttatc agcatctaca     420
aaacgatctg attataagaa tgacagaaac cattggcttg tcttggagga cgttaacaat     480
ctatcactgg atggcggctc gacgggaatt attgatggca acggaaaaat ctggtggcaa     540
aattcatgca aaatcgacca atctaagcca tgcacaaaag ccccaacggc tcttactttc     600
tacaacttaa agaatttgaa tgtgaagaat ctgagagtga gaaatgcgca gcagattcag     660
atttcgattg agaaatgcaa caatgttaac gtcaacaatg tcgagatcac tgctcctgac     720
gatagtccca caccgatgg tattcacatc actaatacac aaaacattcg aatctccaat     780
tcagacattg gcacaggtga tgattgcata tccattgagg atggatccca aaatgttcaa     840
atcaatgatt taacttgcgg ccccggtcac gggatcagca ttgggagttt ggggatgac      900 aattcgaaag cttatgtctc ggggattaat gtagatggtg ctaagctctc ttctactgat     960
aatggagtta gaattaaaac ttaccaggga ggatcaggaa ctgccaagaa cattaaattt    1020 caaatattc gtatggaaaa tgtcaagaat ccaatcataa tcgaccagaa ctactgcgac    1080
aaggacaaat gcgaagaaca agaatccgcg gtgcaagtaa acaatgtggt gtaccggaac    1140
ataaccggta cgagcgcaac ggatgtggcg ataatgttta attgcagtga gaaatatcca    1200
tgccaaggga ttgtgcttga aacgtgaat atcgaaggag gaacagcttc ttgcaaaaat    1260
gccaatgtta aggatcaagg cactgtatct cctcagtgct cttccacttg a            1311

<210> SEQ ID NO 32
<211> LENGTH: 56
<212> TYPE: PRT
<213> ORGANISM: Artificial Sequence
<220> FEATURE:
<223> OTHER INFORMATION: modified pennycress ADPG1 polypeptide sequence

<400> SEQUENCE: 32

Met Ala Arg Arg Phe Gly Leu Leu Ala Ile Phe Leu Cys Val Leu Leu
1               5                   10                  15

Met Leu Ser Trp Cys Glu Ala Leu Ser Ser Asn Val Asp Asp Gly Tyr
            20                  25                  30

Gly His Glu Met Glu Ala Ser Asn Pro Ile Ala Tyr Ser Asn Leu Arg
        35                  40                  45

Thr Thr Thr Thr Thr Phe Leu Pro
    50                  55

<210> SEQ ID NO 33
<211> LENGTH: 1311
<212> TYPE: DNA
<213> ORGANISM: Artificial Sequence
<220> FEATURE:
<223> OTHER INFORMATION: modified pennycress ADPG1 nucleotide sequence

<400> SEQUENCE: 33
atggctcgtc gtttcggact tcttgctatc ttcttatgtg ttcttttgat gctctcgtgg     60
tgcgaagctt tgagtagcaa cgttgatgat ggatatggtc atgaagatgg aagcttcgaa    120
tccgatagct tactcaaact taagaacgac gacgacgacg ttcttacctt gaaaagctcc    180
gataaaacca cttccgaatc atcaactgtt agtgttaccg atttcggtgc taaggagat    240 ggggaaaacg atgatactca ggccttcaag aaagcatgga gaaagcatg ttcaacaaag    300 ggagttacta gtttcttaat tcctaaagga aagacttatc tccttaagtc tactcgattc    360
agaggcccat gcaaatcttt acgtaacttt cagatcctag cactttatc agcatctaca    420 aaacgatctg attataagaa tgacagaaac cattggcttg tcttggagga cgttaacaat    480
ctatcactgg atggcggctc gacgggaatt attgatggca acggaaaaat ctggtggcaa    540
aattcatgca aaatcgacca atctaagcca tgcacaaaag ccccaacggc tcttactttc    600
tacaacttaa agaatttgaa tgtgaagaat ctgagagtga aaatgcgca gcagattcag    660 atttcgattg agaaatgcaa caatgttaac gtcaacaatg tcgagatcac tgctcctgac    720
gatagtccca caccgatggt tattcacatc actaatacac aaaacattcg aatctccaat    780
tcagacattg gcacaggtga tgattgcata tccattgagg atggatccca aaatgttcaa    840
atcaatgatt taacttgcgg ccccggtcac gggatcagca ttgggagttt ggggggatgac    900 aattcgaaag cttatgtctc ggggattaat gtagatggtg ctaagctctc ttctactgat    960
aatggagtta gaattaaaac ttaccaggga ggatcaggaa ctgccaagaa cattaaattt   1020
caaaatattc gtatggaaaa tgtcaagaat ccaatcataa tcgaccagaa ctactgcgac   1080
aaggacaaat gcgaagaaca agaatccgcg gtgcaagtaa acaatgtggt gtaccggaac   1140
ataaccggta cgagcgcaac ggatgtggcg ataatgttta attgcagtga gaaatatcca   1200
tgccaaggga ttgtgcttga gaacgtgaat atcgaaggag gaacagcttc ttgcaaaaat   1260
gccaatgtta aggatcaagg cactgtatct cctcagtgct cttccacttg a            1311

<210> SEQ ID NO 34
<211> LENGTH: 55
<212> TYPE: PRT
<213> ORGANISM: Artificial Sequence
<220> FEATURE:
<223> OTHER INFORMATION: modified pennycress ADPG1 polypeptide sequence

<400> SEQUENCE: 34

Met Ala Arg Arg Phe Gly Leu Leu Ala Ile Phe Leu Cys Val Leu Leu
1               5                   10                  15

Met Leu Ser Trp Cys Glu Ala Leu Ser Ser Asn Val Asp Gly Tyr
            20                  25                  30

Gly Gln Met Glu Ala Ser Asn Pro Ile Ala Tyr Ser Asn Leu Arg Thr
        35                  40                  45

Thr Thr Thr Thr Phe Leu Pro
    50                  55

<210> SEQ ID NO 35
<211> LENGTH: 373
<212> TYPE: PRT
<213> ORGANISM: Arabidopsis thaliana

<400> SEQUENCE: 35

Met Ile Ser Gln Arg Glu Glu Arg Glu Glu Lys Lys Gln Arg Val Met
1               5                   10                  15

Gly Asp Lys Lys Leu Ile Ser Ser Ser Ser Ser Ser Val Tyr Asp
            20                  25                  30

Thr Arg Ile Asn His His Leu His His Pro Pro Ser Ser Ser Asp Glu
        35                  40                  45

Ile Ser Gln Phe Leu Arg His Ile Phe Asp Arg Ser Ser Pro Leu Pro
    50                  55                  60

Ser Tyr Tyr Ser Pro Ala Thr Thr Thr Thr Ala Ser Leu Ile Gly
65                  70                  75                  80

Val His Gly Ser Gly Asp Pro His Ala Asp Asn Ser Arg Ser Leu Val
                85                  90                  95

Ser His His Pro Pro Ser Asp Ser Val Leu Met Ser Lys Arg Val Gly
            100                 105                 110

Asp Phe Ser Glu Val Leu Ile Gly Gly Gly Ser Gly Ser Ala Ala Ala
        115                 120                 125

Cys Phe Gly Phe Ser Gly Gly Asn Asn Asn Val Gln Gly Asn
    130                 135                 140

Ser Ser Gly Thr Arg Val Ser Ser Ser Val Gly Ala Ser Gly Asn
145                 150                 155                 160

Glu Thr Asp Glu Tyr Asp Cys Glu Ser Glu Glu Gly Gly Glu Ala Val
                165                 170                 175

Val Asp Glu Ala Pro Ser Ser Lys Ser Gly Pro Ser Ser Arg Ser Ser
            180                 185                 190

Ser Lys Arg Cys Arg Ala Ala Glu Val His Asn Leu Ser Glu Lys Arg
        195                 200                 205

Arg Arg Ser Arg Ile Asn Glu Lys Met Lys Ala Leu Gln Ser Leu Ile
    210                 215                 220

Pro Asn Ser Asn Lys Thr Asp Lys Ala Ser Met Leu Asp Glu Ala Ile
225                 230                 235                 240

Glu Tyr Leu Lys Gln Leu Gln Leu Gln Val Gln Met Leu Thr Met Arg
                245                 250                 255

Asn Gly Ile Asn Leu His Pro Leu Cys Leu Pro Gly Thr Thr Leu His
            260                 265                 270

Pro Leu Gln Leu Ser Gln Ile Arg Pro Pro Glu Ala Thr Asn Asp Pro
        275                 280                 285

Leu Leu Asn His Thr Asn Gln Phe Ala Ser Thr Ser Asn Ala Pro Glu
    290                 295                 300

Met Ile Asn Thr Val Ala Ser Ser Tyr Ala Leu Glu Pro Ser Ile Arg
305                 310                 315                 320

Ser His Phe Gly Pro Phe Pro Leu Leu Thr Ser Pro Val Glu Met Ser
                325                 330                 335

```
Arg Glu Gly Gly Leu Thr His Pro Arg Leu Asn Ile Gly His Ser Asn
                340                 345                 350

Ala Asn Ile Thr Gly Glu Gln Ala Leu Phe Asp Gly Gln Pro Asp Leu
            355                 360                 365

Lys Asp Arg Ile Thr
        370

<210> SEQ ID NO 36
<211> LENGTH: 297
<212> TYPE: PRT
<213> ORGANISM: Glycine max

<400> SEQUENCE: 36

Met Ala Gly Asp Ile Gly Arg Ala Leu Pro Pro Pro Asp Ser Glu Glu
1               5                   10                  15

Phe Ser Thr Leu Phe Asn Gln Leu Leu His Asn Ser Pro Pro Leu Gly
                20                  25                  30

Met Asp Pro Asn His Ser Pro Ser Asp Phe Thr Pro His Asn Thr Thr
            35                  40                  45

Ile Asn Ile Asn Ser Asn Asn Asn Asn Asn Thr Val Pro Ser Ser Pro
50                  55                  60

Ser Asn Phe Asn Phe Ser Asp Pro His His Tyr Ile Pro Ala Ser Asp
65                  70                  75                  80

Ala Thr Thr Phe Lys Gln His Asn Ile Asn His Asn Asn Asn His Thr
                85                  90                  95

Pro Asp Phe Thr Ser Ser His Val Glu Lys Ser Val Glu Ala Ser Lys
            100                 105                 110

Pro Val Pro Pro Pro Arg Ser Ser Lys Arg Ser Arg Ala Ala Glu
        115                 120                 125

Phe His Asn Leu Ser Glu Lys Arg Arg Arg Ser Arg Ile Asn Glu Lys
    130                 135                 140

Met Lys Ala Leu Gln Asn Leu Ile Pro Asn Ser Asn Lys Thr Asp Lys
145                 150                 155                 160

Ala Ser Met Leu Asp Glu Ala Ile Glu Tyr Leu Lys Gln Leu Gln Leu
                165                 170                 175

Gln Val Gln Met Leu Met Met Arg Asn Gly Leu Ser Leu His Pro Met
            180                 185                 190

Ser Leu Pro Gly Gly Leu Arg Pro Met Ile Met Pro Gln Thr Gly Leu
        195                 200                 205

Asn Leu Asp Gly Ser Asn Gly Phe Gln Asn Ser Thr Cys Ala Ile Ala
    210                 215                 220

Ser Ser Ser Asn Asp Glu Ser Leu Val Arg His Ala Phe Ser Phe Pro
225                 230                 235                 240

Lys Gln Cys Ser Ile Ser Asn Lys Ser Ile Gly Val Pro Ser Val Lys
                245                 250                 255

Asn Ile Ala Thr Ser Asp Thr Ser Thr Phe His Pro Ser Ile Lys
            260                 265                 270

Asp Ala Leu Tyr Gly Asn Met Pro Gln Pro Phe Met Asp Thr Thr Lys
        275                 280                 285

Ile Gly Lys Pro Ser Pro Asp Val Ser
    290                 295

<210> SEQ ID NO 37
<211> LENGTH: 188
<212> TYPE: PRT
```

<213> ORGANISM: Oryza sativa

<400> SEQUENCE: 37

Glu Ala Gly Gly Ser Glu Pro Glu Ala Ala Gly Ala Arg Pro
1               5                   10                  15

Arg Gly Gly Ser Gly Ser Lys Arg Ser Arg Ala Ala Glu Val His Asn
            20                  25                  30

Leu Ser Glu Lys Arg Arg Arg Ser Lys Ile Asn Glu Lys Met Lys Ala
        35                  40                  45

Leu Gln Ser Leu Ile Pro Asn Ser Asn Lys Thr Asp Lys Ala Ser Met
    50                  55                  60

Leu Asp Glu Ala Ile Glu Tyr Leu Lys Gln Leu Gln Leu Gln Val Gln
65                  70                  75                  80

Met Leu Ser Met Arg Asn Gly Val Tyr Leu Asn Pro Ser Tyr Leu Ser
                85                  90                  95

Gly Ala Leu Glu Pro Ala Gln Ala Ser Gln Met Phe Ala Ala Leu Gly
            100                 105                 110

Gly Asn Asn Val Thr Val Val His Pro Gly Thr Val Met Pro Pro Val
        115                 120                 125

Asn Gln Ser Ser Gly Ala His His Leu Phe Asp Pro Leu Asn Ser Pro
    130                 135                 140

Pro Gln Asn Gln Pro Gln Ser Leu Ile Leu Pro Ser Val Pro Ser Thr
145                 150                 155                 160

Ala Ile Pro Glu Pro Pro Phe His Leu Glu Ser Ser Gln Ser His Leu
                165                 170                 175

Arg Gln Phe Gln Leu Pro Gly Ser Ser Glu Val Ile
            180                 185

<210> SEQ ID NO 38
<211> LENGTH: 314
<212> TYPE: PRT
<213> ORGANISM: Solanum lycopersicum

<400> SEQUENCE: 38

Met Ala Asp Pro Tyr Arg Thr Asn Pro His Ala Ser Ser Ser Leu Glu
1               5                   10                  15

Ser Glu Asp Met Ser Ser Phe Phe Leu Asn Phe Leu Gln Gly Thr Pro
            20                  25                  30

Ala Ser Ser Ser Ala Thr Ala Ala Gly Phe Tyr Asn Arg Ser Gly
        35                  40                  45

Pro Ala Pro Val Ala Glu Ser Ser Ser Leu Asn Phe Ser Asp Pro
    50                  55                  60

Gly Arg Phe Tyr Ala Ala Glu Phe Lys Glu Gly Val Glu Asn Val Phe
65                  70                  75                  80

Ala Ser Ala Gly Leu Gly Glu Cys Asp Gly Met Asn Ser Ala Asn Arg
                85                  90                  95

Arg Glu Phe Leu Glu Asp Asp Lys Val Asp Asn Phe Gly Phe Ser Ser
            100                 105                 110

Glu Glu Cys Asp Gly Leu Asp Met Pro Ser Asp Pro Thr His Pro Arg
        115                 120                 125

Ser Ser Lys Arg Ser Arg Ser Ala Glu Val His Asn Leu Ser Glu Lys
    130                 135                 140

Arg Arg Arg Ser Arg Ile Asn Glu Lys Leu Lys Ala Leu Gln Asn Leu
145                 150                 155                 160

Ile Pro Asn Ser Asn Lys Thr Asp Lys Ala Ser Met Leu Asp Glu Ala

-continued

```
                165                 170                 175
Ile Glu Tyr Leu Lys Gln Leu Gln Leu Gln Val Gln Ile Leu Thr Leu
            180                 185                 190

Arg Asn Gly Leu Ser Leu Tyr Pro Gly Tyr Val Pro Gly Ser Leu Gln
        195                 200                 205

Ser Val Gln Leu Pro Ser Gly Asn Glu Phe Asp Gly Arg Ser Phe Met
    210                 215                 220

Leu Ser Ala Asn Gly Gly Ala Thr Leu Pro Val Asn Arg Glu Met Pro
225                 230                 235                 240

Gln Thr Ala Phe Glu Ile Ser Asn Gln Asn Pro Ser Gly Lys Pro Thr
                245                 250                 255

Ile Thr Ser His Asn Thr Glu Asn Ala Val Ala Leu Glu Thr Thr Ile
            260                 265                 270

Gln Asn His Tyr Gly Leu Leu Asn His Leu Ala Ser Ser Lys Asp Met
        275                 280                 285

Cys Arg Asp Asn Thr Leu Ser Arg Leu His Leu Asp Met Ser Cys Ser
    290                 295                 300

Gly Asn Asn Ser Ser Ser Gly Val Ser Ser
305                 310
```

<210> SEQ ID NO 39
<211> LENGTH: 198
<212> TYPE: PRT
<213> ORGANISM: Arabidopsis thaliana

<400> SEQUENCE: 39

```
Met Glu Asn Gly Met Tyr Lys Lys Lys Gly Val Cys Asp Ser Cys Val
1               5                   10                  15

Ser Ser Lys Ser Arg Ser Asn His Ser Pro Lys Arg Ser Met Met Glu
            20                  25                  30

Pro Gln Pro His His Leu Leu Met Asp Trp Asn Lys Ala Asn Asp Leu
        35                  40                  45

Leu Thr Gln Glu His Ala Ala Phe Leu Asn Asp Pro His His Leu Met
    50                  55                  60

Leu Asp Pro Pro Pro Glu Thr Leu Ile His Leu Asp Glu Asp Glu Glu
65                  70                  75                  80

Tyr Asp Glu Asp Met Asp Ala Met Lys Glu Met Gln Tyr Met Ile Ala
                85                  90                  95

Val Met Gln Pro Val Asp Ile Asp Pro Ala Thr Val Pro Lys Pro Asn
            100                 105                 110

Arg Arg Asn Val Arg Ile Ser Asp Pro Gln Thr Val Val Ala Arg
        115                 120                 125

Arg Arg Arg Glu Arg Ile Ser Glu Lys Ile Arg Ile Leu Lys Arg Ile
    130                 135                 140

Val Pro Gly Gly Ala Lys Met Asp Thr Ala Ser Met Leu Asp Glu Ala
145                 150                 155                 160

Ile Arg Tyr Thr Lys Phe Leu Lys Arg Gln Val Arg Ile Leu Gln Pro
                165                 170                 175

His Ser Gln Ile Gly Ala Pro Met Ala Asn Pro Ser Tyr Leu Cys Tyr
            180                 185                 190

Tyr His Asn Ser Gln Pro
        195
```

<210> SEQ ID NO 40
<211> LENGTH: 270

```
<212> TYPE: PRT
<213> ORGANISM: Glycine max

<400> SEQUENCE: 40
```

| | | | | | | | | | | | | | | |
|---|---|---|---|---|---|---|---|---|---|---|---|---|---|---|

Met Asp Thr Asn Thr Ser Thr Leu Phe Thr Asn Val Asn Ser Thr Trp
1               5                   10                  15

Asn Leu Glu Lys Met Glu Thr Asn Glu Gln Gln Gln Gln His Asp Asp
            20                  25                  30

His Ser Ile Ile Leu Gln Val Gln Asp Pro Met Gly Ser Gly Ile Trp
        35                  40                  45

Pro Ile Asn Asn Tyr Gln Asn Leu Leu Gln Met His Gln Thr Pro Asn
    50                  55                  60

Thr Thr Thr Ser Ser Thr Val Ile Val Pro Pro Ser Ser Ser Ser Gly
65                  70                  75                  80

Phe Leu Gly Asp Ile Leu Gly Val His His Asn Leu Glu Glu Asp Glu
                85                  90                  95

Glu Pro Glu Glu Glu Leu Gly Ala Met Lys Glu Met Met Tyr Lys Ile
            100                 105                 110

Ala Ala Met Gln Pro Val Asp Ile Asp Pro Ala Thr Ile Arg Lys Pro
        115                 120                 125

Lys Arg Arg Asn Val Arg Ile Ser Asp Asp Pro Gln Ser Val Ala Ala
    130                 135                 140

Arg His Arg Arg Glu Arg Ile Ser Glu Lys Ile Arg Ile Leu Gln Arg
145                 150                 155                 160

Leu Val Pro Gly Gly Thr Lys Met Asp Thr Ala Ser Met Leu Asp Glu
                165                 170                 175

Ala Ile Arg Tyr Val Lys Phe Leu Lys Arg Gln Ile Arg Leu Leu Gln
            180                 185                 190

Ser Ile Pro Gln Pro Ser Arg Gln Pro Pro Gln Cys Ile Gly Val Ala
        195                 200                 205

Ser Thr Thr Pro His Ala Ser Thr Leu Leu Ala Pro Ser Ser Asp
    210                 215                 220

Trp Pro Phe Ala Pro Asn Val Leu Pro Arg Ser Thr Ala Val Ser Ala
225                 230                 235                 240

Ser Met Asp Met Ser Ala Gly Leu Gly Phe Asp Gly His Ala His Ala
                245                 250                 255

Cys Asp Gly Ser Ser Ser Phe Asn His His Glu Val Ile Ser
            260                 265                 270

```
<210> SEQ ID NO 41
<211> LENGTH: 270
<212> TYPE: PRT
<213> ORGANISM: Oryza sativa

<400> SEQUENCE: 41
```

Met Asp Thr Asn Thr Ser Thr Leu Phe Thr Asn Val Asn Ser Thr Trp
1               5                   10                  15

Asn Leu Glu Lys Met Glu Thr Asn Glu Gln Gln Gln Gln His Asp Asp
            20                  25                  30

His Ser Ile Ile Leu Gln Val Gln Asp Pro Met Gly Ser Gly Ile Trp
        35                  40                  45

Pro Ile Asn Asn Tyr Gln Asn Leu Leu Gln Met His Gln Thr Pro Asn
    50                  55                  60

Thr Thr Thr Ser Ser Thr Val Ile Val Pro Pro Ser Ser Ser Ser Gly
65                  70                  75                  80

-continued

```
Phe Leu Gly Asp Ile Leu Gly Val His His Asn Leu Glu Glu Asp Glu
                85                  90                  95

Glu Pro Glu Glu Glu Leu Gly Ala Met Lys Glu Met Tyr Lys Ile
            100                 105                 110

Ala Ala Met Gln Pro Val Asp Ile Asp Pro Ala Thr Ile Arg Lys Pro
            115                 120                 125

Lys Arg Arg Asn Val Arg Ile Ser Asp Asp Pro Gln Ser Val Ala Ala
            130                 135                 140

Arg His Arg Arg Glu Arg Ile Ser Glu Lys Ile Arg Ile Leu Gln Arg
145                 150                 155                 160

Leu Val Pro Gly Gly Thr Lys Met Asp Thr Ala Ser Met Leu Asp Glu
                165                 170                 175

Ala Ile Arg Tyr Val Lys Phe Leu Lys Arg Gln Ile Arg Leu Leu Gln
            180                 185                 190

Ser Ile Pro Gln Pro Ser Arg Gln Pro Pro Gln Cys Ile Gly Val Ala
            195                 200                 205

Ser Thr Thr Pro His Ala Ser Thr Leu Leu Ala Pro Ser Ser Asp
            210                 215                 220

Trp Pro Phe Ala Pro Asn Val Leu Pro Arg Ser Thr Ala Val Ser Ala
225                 230                 235                 240

Ser Met Asp Met Ser Ala Gly Leu Gly Phe Asp Gly His Ala His Ala
                245                 250                 255

Cys Asp Gly Ser Ser Phe Asn His His Glu Val Ile Ser
            260                 265                 270

<210> SEQ ID NO 42
<211> LENGTH: 283
<212> TYPE: PRT
<213> ORGANISM: Solanum lycopersicum

<400> SEQUENCE: 42

Met Asp Ile Asn His Ile Asn Lys Leu Thr Thr Ser Thr Trp Asp Pro
1               5                   10                  15

Thr Met Ser Asn Met Asp Asn Gln Gln Val Phe Arg Asp Gln Gln Gln
            20                  25                  30

Gln Gln Gln Pro Cys Leu Ser Ser Ile Pro Asn Asp His Ile Tyr His
            35                  40                  45

Glu His His His Gln Gln Gln Phe His Phe Glu His Asn Pro Ile
        50                  55                  60

Trp Pro Ser Phe Pro Leu Gln Asn Pro Gln His His Leu Pro Ser
65                  70                  75                  80

Ser Ser Thr Gln Gln Gln Gln Gln Gln Glu Glu Val Val Val
                85                  90                  95

Pro Phe Asp His Val Leu Asn Asn His Val Gln Thr Leu Ile Glu Asp
            100                 105                 110

Gln Glu His Asp Asp Gln Asp Glu Asp Glu Glu Glu Glu Leu
            115                 120                 125

Gly Ala Met Lys Glu Met Met Phe Lys Ile Ala Ser Met Gln Pro Val
            130                 135                 140

Asp Ile Asp Pro Ser Thr Ile Arg Lys Pro Lys Arg Arg Asn Val Arg
145                 150                 155                 160

Ile Ser Asn Asp Pro Gln Ser Val Ala Ala Arg Leu Arg Arg Glu Arg
            165                 170                 175

Ile Ser Glu Lys Ile Arg Ile Leu Gln Arg Leu Val Pro Gly Gly Thr
            180                 185                 190
```

```
Lys Met Asp Thr Ala Ser Met Leu Asp Glu Ala Ile Arg Tyr Val Lys
        195                 200                 205

Phe Leu Lys Arg Gln Ile Arg Gln Leu Gln Ser Ser Asn His Asn Leu
    210                 215                 220

Pro Pro Ala Gln Ile Pro Val Ser Ser Cys Pro Asn Asn Glu Asn Trp
225                 230                 235                 240

Ala Asn Asn Ile Val Thr Pro Ser Thr Lys Gly Leu Ile Leu Gly Ser
                245                 250                 255

Ser Ser Ser Thr Thr Thr Asn Asn Val Thr Thr Phe Val Gly Asn Thr
                260                 265                 270

Thr Leu Asp Pro Pro Tyr Glu Val Ile Gly Asn
        275                 280

<210> SEQ ID NO 43
<211> LENGTH: 108
<212> TYPE: DNA
<213> ORGANISM: Artificial Sequence
<220> FEATURE:
<223> OTHER INFORMATION: PCR sequencing fragment of ALC mutant line ME3
<220> FEATURE:
<221> NAME/KEY: misc_feature
<222> LOCATION: (54)..(54)
<223> OTHER INFORMATION: n is a, c, g, or t

<400> SEQUENCE: 43
atccttgtct gtgttggtgg taatcagcat tgggtttagg cctaaaccat tcangactgc    60
taaagtctgc attatccatt gtatgatcaa ataagcgctg agttttac                108

<210> SEQ ID NO 44
<211> LENGTH: 108
<212> TYPE: DNA
<213> ORGANISM: Artificial Sequence
<220> FEATURE:
<223> OTHER INFORMATION: PCR sequencing fragment of ALC mutant line ME5
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(80)
```

<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t

<400> SEQUENCE: 44
atccttgtct gtgttggtgg taatnncatt tgggcntang ccnntcccga ncgcgacngc    60
cagcgtcagc cntagcnngn gcangaacnc ncngacgntg antttnan               108

<210> SEQ ID NO 45
<211> LENGTH: 107
<212> TYPE: DNA
<213> ORGANISM: Artificial Sequence
<220> FEATURE:
<223> OTHER INFORMATION: PCR sequencing fragment of ALC mutant line ME6
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

```
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(82)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (88)..(91)
<223> OTHER INFORMATION: n is a, c, g, or t
<220> FEATURE:
<221> NAME/KEY: misc_feature
<222> LOCATION: (100)..(101)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t

<400> SEQUENCE: 45
atccttgtct gtgttggtga taangcnttg aggncaagcc cantccagnc nggannngntn      60 ngnnctnncn tatgcatngt nngatnannn ntgagctgan ntttana                   107

<210> SEQ ID NO 46
<211> LENGTH: 108
<212> TYPE: DNA
<213> ORGANISM: Thlaspi arvense

<400> SEQUENCE: 46
atccttgtct gtgttggtgg taatcgcatt gggtttaggc ctaaaccatt catgactgct      60
aaagtctgca ttatccattg tatgatcaaa taagcgctga gttttaca                  108

<210> SEQ ID NO 47
<211> LENGTH: 438
<212> TYPE: PRT
<213> ORGANISM: Arabidopsis thaliana

<400> SEQUENCE: 47
```

Met Leu Arg Glu Ser Asp Gly Glu Met Ser Leu Gly Thr Thr Asn Ser
1               5                   10                  15

Pro Ile Ser Ser Gly Thr Glu Ser Cys Ser Ser Phe Ser Arg Leu Ser
            20                  25                  30

Phe Asp Ala Pro Pro Ser Thr Ile Pro Glu Glu Glu Ser Phe Leu Ser
        35                  40                  45

Leu Lys Pro His Arg Ser Ser Asp Phe Ala Tyr Ala Glu Ile Arg Arg
    50                  55                  60

```
Arg Lys Lys Gln Gly Leu Thr Phe Arg Asp Phe Arg Leu Met Arg Arg
 65                  70                  75                  80

Ile Gly Ala Gly Asp Ile Gly Thr Val Tyr Leu Cys Arg Leu Ala Gly
                 85                  90                  95

Asp Glu Glu Glu Ser Arg Ser Ser Tyr Phe Ala Met Lys Val Val Asp
            100                 105                 110

Lys Glu Ala Leu Ala Leu Lys Lys Met His Arg Ala Glu Met Glu
        115                 120                 125

Lys Thr Ile Leu Lys Met Leu Asp His Pro Phe Leu Pro Thr Leu Tyr
        130                 135                 140

Ala Glu Phe Glu Ala Ser His Phe Ser Cys Ile Val Met Glu Tyr Cys
145                 150                 155                 160

Ser Gly Gly Asp Leu His Ser Leu Arg His Arg Gln Pro His Arg Arg
                165                 170                 175

Phe Ser Leu Ser Ser Ala Arg Phe Tyr Ala Ala Glu Val Leu Val Ala
                180                 185                 190

Leu Glu Tyr Leu His Met Leu Gly Ile Ile Tyr Arg Asp Leu Lys Pro
            195                 200                 205

Glu Asn Ile Leu Val Arg Ser Asp Gly His Ile Met Leu Ser Asp Phe
210                 215                 220

Asp Leu Ser Leu Cys Ser Asp Ser Ile Ala Ala Val Glu Ser Ser
225                 230                 235                 240

Ser Ser Pro Glu Asn Gln Gln Leu Arg Ser Pro Arg Arg Phe Thr Arg
                245                 250                 255

Leu Ala Arg Leu Phe Gln Arg Val Leu Arg Ser Lys Lys Val Gln Thr
            260                 265                 270

Leu Glu Pro Thr Arg Leu Phe Val Ala Glu Pro Val Thr Ala Arg Ser
        275                 280                 285

Gly Ser Phe Val Gly Thr His Glu Tyr Val Ala Pro Glu Val Ala Ser
        290                 295                 300

Gly Gly Ser His Gly Asn Ala Val Asp Trp Trp Ala Phe Gly Val Phe
305                 310                 315                 320

Leu Tyr Glu Met Ile Tyr Gly Lys Thr Pro Phe Val Ala Pro Thr Asn
                325                 330                 335

Asp Val Ile Leu Arg Asn Ile Val Lys Arg Gln Leu Ser Phe Pro Thr
                340                 345                 350

Asp Ser Pro Ala Thr Met Phe Glu Leu His Ala Arg Asn Leu Ile Ser
            355                 360                 365

Gly Leu Leu Asn Lys Asp Pro Thr Lys Arg Leu Gly Ser Arg Arg Gly
        370                 375                 380

Ala Ala Glu Val Lys Val His Pro Phe Phe Lys Gly Leu Asn Phe Ala
385                 390                 395                 400

Leu Ile Arg Thr Leu Thr Pro Pro Glu Ile Pro Ser Ser Val Val Lys
                405                 410                 415

Lys Pro Met Lys Ser Ala Thr Phe Ser Gly Arg Ser Ser Asn Lys Pro
            420                 425                 430

Ala Ala Phe Asp Tyr Phe
            435

<210> SEQ ID NO 48
<211> LENGTH: 452
<212> TYPE: PRT
<213> ORGANISM: Glycine max

<400> SEQUENCE: 48
```

```
Met Glu Thr Gly Gly Gly Arg Asp Ser Gly Met Ser Ser Glu Thr Ile
1               5                   10                  15

Asn Ser Ser Thr Gln Arg Thr Ser Met Ser Asn Glu Ser Val Cys Ser
            20                  25                  30

Thr Ser Phe Ser Arg Leu Ser Phe Asp Leu Pro Pro Pro Ser Ser Ser
        35                  40                  45

Pro Glu Thr Leu Phe Val Lys Pro His Arg Ser Ser Asp Phe Ala Tyr
    50                  55                  60

Ser Ala Ile Leu Arg Arg Lys Ser Ala Leu Thr Phe Arg Asp Phe His
65              70                  75                  80

Leu Leu Arg Arg Ile Gly Ala Gly Asp Ile Gly Thr Val Tyr Leu Cys
                85                  90                  95

Arg Leu Arg His Asp Ala Gly Asp Glu Asp Asp Asp Glu Asp Pro Cys
                100                 105                 110

Phe Tyr Ala Met Lys Val Val Asp Lys Glu Ala Val Ala Leu Lys Lys
            115                 120                 125

Lys Ala Gln Arg Ala Glu Met Glu Arg Lys Ile Leu Lys Met Val Asp
    130                 135                 140

His Pro Phe Leu Pro Thr Leu Tyr Ala Glu Phe Glu Ala Ser Asn Phe
145                 150                 155                 160

Ser Cys Ile Val Met Glu Tyr Cys Ser Gly Gly Asp Leu His Ser Leu
                165                 170                 175

Gln His Asn His Pro Asn Asn Arg Phe Ser Leu Ser Ser Ala Arg Phe
                180                 185                 190

Tyr Ala Ala Glu Val Leu Val Ala Leu Glu Tyr Leu His Met Leu Gly
                195                 200                 205

Ile Ile Tyr Arg Asp Leu Lys Pro Glu Asn Val Leu Val Arg Ser Asp
                210                 215                 220

Gly His Ile Met Leu Ser Asp Phe Asp Leu Ser Leu Cys Ser Asp Ala
225                 230                 235                 240

Ile Pro Ala Val Glu Ser Pro Asp Cys Ser Leu Asp Pro Ala Phe Ala
                245                 250                 255

Pro Ala Leu Arg Tyr Thr Arg Gln Tyr Ser Thr Pro Phe Ser Cys Leu
                260                 265                 270

Ser Asn Arg Val Phe Arg Ser Arg Lys Val Gln Thr Leu Gln Pro Asn
                275                 280                 285

Arg Leu Phe Val Ala Glu Pro Val Gly Ala Arg Ser Cys Ser Phe Val
                290                 295                 300

Gly Thr His Glu Tyr Val Ser Pro Glu Val Ala Ser Gly Asn Ser His
305                 310                 315                 320

Gly Asn Ala Val Asp Trp Trp Ser Phe Gly Ile Phe Ile Tyr Glu Met
                325                 330                 335

Val Tyr Gly Arg Thr Pro Phe Ala Gly Ser Ser Asn Glu Ala Thr Leu
                340                 345                 350

Arg Ser Ile Ile Lys Lys Pro Leu Ala Phe Pro Thr Ser Thr Pro Ser
                355                 360                 365

Ser Thr Leu Glu Met His Ala Arg Asp Leu Ile Ser Gly Leu Leu Asn
                370                 375                 380

Lys Asp Pro Asn Arg Arg Leu Gly Ser Lys Arg Gly Ser Ala Asp Val
385                 390                 395                 400

Lys Lys His Pro Phe Phe Ala Gly Leu Asn Leu Ala Leu Ile Arg Thr
                405                 410                 415
```

```
Val Thr Pro Pro Glu Val Pro Ser Leu Arg Arg His Lys Thr Thr Pro
            420                 425                 430

Phe Tyr Tyr Pro Ala Asn Val Asn Asn Ser Arg Gln Gln Leu Thr Ala
            435                 440                 445

Phe Asp Tyr Phe
            450

<210> SEQ ID NO 49
<211> LENGTH: 484
<212> TYPE: PRT
<213> ORGANISM: Oryza sativa

<400> SEQUENCE: 49

Met Val Ala Ala Val Arg Ala Pro Val Lys Pro Glu Met Val Glu Leu
1               5                  10                  15

Ser Pro Ala Ala Met Glu Arg Tyr Ser Ser Asp Ala Asp Thr Thr Ala
            20                  25                  30

Pro Asn Ser Ser Leu Ser Ser Ala Ala Ser Ser Thr Gly Ser Leu Ala
            35                  40                  45

Arg Cys Ser Ser Leu Ser Arg Leu Ser Phe Asp Cys Ser Pro Ser Ala
50                  55                  60

Ala Val Ala Ala Ala Thr Ser Cys Ser Pro Pro Arg Ala Ser Val
65                  70                  75                  80

Leu Leu Arg Pro His Arg Ser Gly Asp Val Ala Trp Ala Ala Ile Arg
                85                  90                  95

Ala Ala Ser Thr Thr Ser Ala Ala Pro Leu Gly Pro Arg Asp Phe Lys
            100                 105                 110

Leu Val Arg Arg Ile Gly Gly Gly Asp Ile Gly Thr Val Tyr Leu Cys
        115                 120                 125

Arg Leu Arg Ser Ser Pro Glu Arg Glu Ser Pro Cys Met Tyr Ala Met
130                 135                 140

Lys Val Val Asp Arg Arg Ala Val Ala Arg Lys Gln Lys Leu Gly Arg
145                 150                 155                 160

Ala Ala Ala Glu Lys Arg Ile Leu Arg Gln Leu Asp His Pro Phe Leu
                165                 170                 175

Pro Thr Leu Phe Ala Asp Phe Asp Ala Thr Pro His Phe Ser Cys Ala
            180                 185                 190

Val Met Glu Phe Cys Pro Gly Gly Asp Leu His Ser Leu Arg His Arg
        195                 200                 205

Met Pro Ser Arg Arg Phe Pro Leu Pro Ser Ala Arg Phe Tyr Ala Ala
210                 215                 220

Glu Val Leu Leu Ala Ile Glu Tyr Leu His Met Met Gly Ile Val Tyr
225                 230                 235                 240

Arg Asp Leu Lys Pro Glu Asn Val Leu Ile Arg Ala Asp Gly His Ile
                245                 250                 255

Met Leu Thr Asp Phe Asp Leu Ser Leu Gln Ser Thr Thr Ser Pro Ser
            260                 265                 270

Leu Asp Gly Asp Thr Asp Thr Asp Asp Glu Ala Ser Gly Gly Ala Ser
        275                 280                 285

Cys Phe Pro Asp His Leu Leu Arg Phe Lys Arg Arg Asn Ala Val
290                 295                 300

Ala Ala Pro Arg Pro Arg Phe Val Ala Glu Pro Val Asp Ala Arg Ser
305                 310                 315                 320

Cys Ser Phe Val Gly Thr His Glu Tyr Val Ala Pro Glu Val Ala Ser
                325                 330                 335
```

```
Gly Gly Ala His Gly Ala Ala Val Asp Trp Trp Ala Tyr Gly Val Phe
            340                 345                 350

Leu Tyr Glu Leu Ile Tyr Gly Arg Thr Pro Phe Ala Gly Ala Thr Asn
        355                 360                 365

Glu Ala Thr Leu Arg Asn Ile Val Arg Arg Pro Leu Ala Phe Pro Ser
    370                 375                 380

Gly Ser Gly Ser Cys Gly Pro Ala Asp Ala Asp Ala Arg Asp Leu Ile
385                 390                 395                 400

Ala Arg Leu Leu Ala Lys Asp Pro Ala Ala Arg Leu Gly Ser Arg Arg
                405                 410                 415

Gly Ala Ala Asp Val Lys Ser His Pro Phe Phe Lys Ser Leu Asn Leu
            420                 425                 430

Ala Leu Leu Arg Ser Ser Arg Pro Pro Val Val Pro Gly Ala Gly Ala
        435                 440                 445

Gly Ala Ala Pro Leu His Arg Ser Gln Ser Cys Lys Ala Ala Pro Thr
    450                 455                 460

Thr Pro Pro Pro Pro Thr Thr Thr Lys Pro Ala Asn Ala Thr Ala Arg
465                 470                 475                 480

Phe Asp Leu Phe

<210> SEQ ID NO 50
<211> LENGTH: 462
<212> TYPE: PRT
<213> ORGANISM: Solanum lycopersicum

<400> SEQUENCE: 50

Met Ala Thr Thr Asn Arg Asp Glu Ser Asp Lys Asp Ser Thr Ala Ser
1               5                   10                  15

Ser Ser Ile Thr Met Pro Glu Ser Ser Arg Arg Ser Trp Met Ser Ser
            20                  25                  30

Thr Asn Leu Ser Ser Phe Ser Ser Arg Arg Ser Ser Ile Ser Leu Cys
        35                  40                  45

Asn Glu Asn Pro Tyr Phe Ser Asn Ser His Lys Pro His Lys Ser Asn
    50                  55                  60

Gln Ile Ser Trp Glu Leu Ile Arg Arg Ile Arg Val Glu Ser Gly Gln
65                  70                  75                  80

Ile Lys Leu Glu His Phe Arg Leu Leu Arg Arg Val Gly Gly Gly Asp
                85                  90                  95

Ile Gly Ser Val Tyr Leu Cys Glu Ile Arg Asn Pro Val Val Gly Leu
            100                 105                 110

Pro Gln Cys Phe Tyr Ala Met Lys Val Val Asp Arg Glu Ala Val Glu
        115                 120                 125

Ile Arg Lys Lys Leu Gln Arg Gly Glu Met Glu Lys Glu Ile Leu Gly
    130                 135                 140

Ile Ile Asp His Pro Phe Leu Pro Thr Leu Tyr Ala Gln Phe Glu Ala
145                 150                 155                 160

Ser His Tyr Ser Cys Leu Val Met Glu Tyr Cys Pro Gly Gly Asp Leu
                165                 170                 175

His Ala Val Arg Gln Arg Gln Pro Gly Lys Arg Phe Ser Ile Ser Ser
            180                 185                 190

Ala Lys Phe Tyr Ala Ala Glu Ile Leu Leu Ala Leu Glu Tyr Leu His
        195                 200                 205

Met Met Gly Ile Val Tyr Arg Asp Leu Lys Pro Glu Asn Val Leu Val
    210                 215                 220
```

Arg Ser Asp Gly His Ile Met Leu Ser Asp Phe Asp Leu Ser Phe Lys
225                 230                 235                 240

Cys Asp Glu Val Val Pro Thr Leu Val Lys Ser Lys Thr Thr Lys Ser
            245                 250                 255

Ile Ala Lys Thr Pro Arg Asn Ser Tyr Cys Ala Met Pro Ile Gln Pro
        260                 265                 270

Val Leu Ser Cys Phe Leu Ser Gln Lys Thr Glu Gln Asn His Glu Asn
    275                 280                 285

Gln Glu Glu Asp Gln Glu Ile Val Ala Glu Pro Ile Asn Ala Arg Ser
290                 295                 300

Lys Ser Phe Val Gly Thr His Glu Tyr Leu Ala Pro Glu Val Ile Ser
305                 310                 315                 320

Gly Gln Gly His Gly Ser Ala Val Asp Trp Trp Thr Leu Gly Val Phe
                325                 330                 335

Leu Tyr Glu Leu Ile Phe Gly Thr Thr Pro Phe Lys Gly Glu Asn Asn
            340                 345                 350

Glu Lys Thr Leu Val Asn Ile Leu Lys Pro Leu Thr Phe Pro Arg
        355                 360                 365

Ile Ala Ile Ser Ser Ser Lys Glu Tyr Glu Met Val Lys Val Gln
370                 375                 380

Asp Leu Ile Ser Arg Leu Leu Val Lys Asn Pro Lys Lys Arg Ile Gly
385                 390                 395                 400

Ser Leu Gln Gly Ser Val Glu Ile Lys Lys His Glu Phe Phe Lys Gly
                405                 410                 415

Val Asn Trp Ala Leu Ile Arg Ser Ile Lys Pro Pro Gln Val Pro Asn
            420                 425                 430

Asp Leu Val Lys Met Arg Gly Val Val Pro Lys Leu Ser Lys Lys Gln
            435                 440                 445

Arg Glu Glu Pro Tyr Gln Ile Pro Gln Tyr Phe Asp Tyr Phe
450                 455                 460

<210> SEQ ID NO 51
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 51
gggcaatgtt attacctccg                                              20

<210> SEQ ID NO 52
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 52
ggctctatga cagaccaatc                                              20

<210> SEQ ID NO 53
<211> LENGTH: 24
<212> TYPE: DNA
<213> ORGANISM: Artificial Sequence
<220> FEATURE:
<223> OTHER INFORMATION: synthetic oligonucleotide protospacer

<400> SEQUENCE: 53

```
attgtgcgat taccaccaac acag                                          24

<210> SEQ ID NO 54
<211> LENGTH: 24
<212> TYPE: DNA
<213> ORGANISM: Artificial Sequence
<220> FEATURE:
<223> OTHER INFORMATION: synthetic oligonucleotide protospacer

<400> SEQUENCE: 54
aaacctgtgt tggtggtaat cgca                                          24

<210> SEQ ID NO 55
<211> LENGTH: 30
<212> TYPE: DNA
<213> ORGANISM: Artificial Sequence
<220> FEATURE:
<223> OTHER INFORMATION: synthetic oligonucleotide primer

<400> SEQUENCE: 55
aggagctaaa catcgaaatt cgttgaagag                                    30

<210> SEQ ID NO 56
<211> LENGTH: 30
<212> TYPE: DNA
<213> ORGANISM: Artificial Sequence
<220> FEATURE:
<223> OTHER INFORMATION: synthetic oligonucleotide primer

<400> SEQUENCE: 56
tgtcgcagat actagaggaa catcacatca                                    30

<210> SEQ ID NO 57
<211> LENGTH: 20
<212> TYPE: DNA
<213> ORGANISM: Artificial Sequence
<220> FEATURE:
<223> OTHER INFORMATION: synthetic oligonucleotide protospacer

<400> SEQUENCE: 57
gatggatatg gtcatgaaga                                               20

<210> SEQ ID NO 58
<211> LENGTH: 20
<212> TYPE: DNA
<213> ORGANISM: Artificial Sequence
<220> FEATURE:
<223> OTHER INFORMATION: synthetic oligonucleotide protospacer

<400> SEQUENCE: 58
tcttcatgac catatccatc                                               20

<210> SEQ ID NO 59
<211> LENGTH: 50
<212> TYPE: DNA
<213> ORGANISM: Thlaspi arvense

<400> SEQUENCE: 59
cttgtctgtg ttggtggtaa tcgcattggg tttaggccta aaccattcat              50

<210> SEQ ID NO 60
<211> LENGTH: 50
<212> TYPE: DNA
<213> ORGANISM: Artificial Sequence
<220> FEATURE:
```

-continued

<223> OTHER INFORMATION: modified pennycress ALC nucleotide sequence

<400> SEQUENCE: 60
cttgtctgtg ttggtggtaa tcacattggg tttaggccta aaccattcat          50

<210> SEQ ID NO 61
<211> LENGTH: 44
<212> TYPE: DNA
<213> ORGANISM: Artificial Sequence
<220> FEATURE:
<223> OTHER INFORMATION: modified pennycress ALC nucleotide sequence

<400> SEQUENCE: 61
cttgtctgtg ttggtggtaa tgggtttagg cctaaaccat tcat                44

<210> SEQ ID NO 62
<211> LENGTH: 41
<212> TYPE: DNA
<213> ORGANISM: Artificial Sequence
<220> FEATURE:
<223> OTHER INFORMATION: modified pennycress ALC nucleotide sequence

<400> SEQUENCE: 62
cttgtctgtg ttggtggtgg gtttaggcct aaaccattca t                   41

<210> SEQ ID NO 63
<211> LENGTH: 45
<212> TYPE: DNA
<213> ORGANISM: Artificial Sequence
<220> FEATURE:
<223> OTHER INFORMATION: modified pennycress ALC nucleotide sequence

<400> SEQUENCE: 63
cttgtctgtg ttggtggtaa tgggtttag gcctaaacca ttcat                45

<210> SEQ ID NO 64
<211> LENGTH: 45
<212> TYPE: DNA
<213> ORGANISM: Artificial Sequence
<220> FEATURE:
<223> OTHER INFORMATION: modified pennycress ALC nucleotide sequence

<400> SEQUENCE: 64
cttgtctgtg ttggtggtgc atgggtttag gcctaaacca ttcat               45

<210> SEQ ID NO 65
<211> LENGTH: 47
<212> TYPE: DNA
<213> ORGANISM: Artificial Sequence
<220> FEATURE:
<223> OTHER INFORMATION: modified pennycress ALC nucleotide sequence

<400> SEQUENCE: 65
cttgtctgtg ttggtggtaa tcatgggttt aggcctaaac cattcat             47

<210> SEQ ID NO 66
<211> LENGTH: 49
<212> TYPE: DNA
<213> ORGANISM: Artificial Sequence
<220> FEATURE:
<223> OTHER INFORMATION: modified pennycress ALC nucleotide sequence

<400> SEQUENCE: 66
cttgtctgtg ttggtgatta agcattgggt ttaggcctaa accattcat           49

<210> SEQ ID NO 67
<211> LENGTH: 50
<212> TYPE: DNA
<213> ORGANISM: Artificial Sequence
<220> FEATURE:
<223> OTHER INFORMATION: modified pennycress ALC nucleotide sequence

<400> SEQUENCE: 67
cttgtctgtg ttggtggtaa tcagcattgg gtttaggcct aaaccattca                50

<210> SEQ ID NO 68
<211> LENGTH: 50
<212> TYPE: DNA
<213> ORGANISM: Artificial Sequence
<220> FEATURE:
<223> OTHER INFORMATION: modified pennycress ALC nucleotide sequence

<400> SEQUENCE: 68
cttgtctgtg ttggtggtaa tctgcattgg gtttaggcct aaaccattca                50

<210> SEQ ID NO 69
<211> LENGTH: 591
<212> TYPE: DNA
<213> ORGANISM: Thlaspi arvense

<400> SEQUENCE: 69
atgtttggct caaaagcaga tccacccata accccaatag tcatgatgga gcctcaacct     60
catcatctcc tcatgaattg aacaaacct aatgatctca tcacacaaga ataccccttt    120
ctccacgatc ctcatctcat gatagatcca cctcccgaaa ccctaagtca tttccagccc   180
ccgccgacac ttttctccgg tcacggaggg gaggaagaag aagaagaaga taatgaagag   240
gaagagatgg atgcgatgaa ggagatgcag tacacgatcg ctgccatgca gcccgtggac   300
atcgatccag ccaccgttcc taaaccgaac cgccgtaacg taagggtaag cgacgacact   360
cagacggtgg tggctcgtcg gcgtcgagaa aagataagcg agaagatccg aatattgaag   420
aggatggtgc aggcggtgc gaagatggac acagcctcca tgctcgacga agccatccgt   480
tataccaagt tcttgaaacg gcaggtgaag cttcttcagc ctcactctca gcttggagct   540
cctatgtctg acccctcttg cctttgttat taccacaact cccaaaccta a             591

<210> SEQ ID NO 70
<211> LENGTH: 196
<212> TYPE: PRT
<213> ORGANISM: Thlaspi arvense

<400> SEQUENCE: 70

Met Phe Gly Ser Lys Ala Asp Pro Pro Ile Thr Pro Ile Val Met Met
1               5                   10                  15

Glu Pro Gln Pro His His Leu Leu Met Asn Trp Asn Lys Pro Asn Asp
            20                  25                  30

Leu Ile Thr Gln Glu Tyr Pro Phe Leu His Asp Pro His Leu Met Ile
        35                  40                  45

Asp Pro Pro Glu Thr Leu Ser His Phe Gln Pro Pro Thr Leu
    50                  55                  60

Phe Ser Gly His Gly Gly Glu Glu Glu Glu Glu Asp Asn Glu Glu
65                  70                  75                  80

Glu Glu Met Asp Ala Met Lys Glu Met Gln Tyr Thr Ile Ala Ala Met
                85                  90                  95

Gln Pro Val Asp Ile Asp Pro Ala Thr Val Pro Lys Pro Asn Arg Arg
            100                 105                 110

-continued

```
Asn Val Arg Val Ser Asp Asp Thr Gln Thr Val Val Ala Arg Arg Arg
        115             120             125

Arg Glu Lys Ile Ser Glu Lys Ile Arg Ile Leu Lys Arg Met Val Pro
    130             135             140

Gly Gly Ala Lys Met Asp Thr Ala Ser Met Leu Asp Glu Ala Ile Arg
145             150             155             160

Tyr Thr Lys Phe Leu Lys Arg Gln Val Lys Leu Leu Gln Pro His Ser
            165             170             175

Gln Leu Gly Ala Pro Met Ser Asp Pro Ser Cys Leu Cys Tyr Tyr His
        180             185             190

Asn Ser Gln Thr
        195
```

OILSEED PLANTS HAVING REDUCED POD SHATTER

CROSS-REFERENCE TO RELATED APPLICATIONS

This application claims the benefit of U.S. Patent Application Ser. No. 62/547,684, filed on Aug. 18, 2017. The disclosure of the prior application is considered part of (and is incorporated by reference in) the disclosure of this application.

STATEMENT REGARDING FEDERAL FUNDING

This invention was made with government support under 2014-67009-22305 awarded by the United States Department of Agriculture. The government has certain rights in the invention.

BACKGROUND

1. Technical Field

This document relates to materials and methods for domesticating oilseed (e.g., pennycress) plants. For example, this document provides oilseed plants having reduced seedpod shatter, as well as materials and methods for making and using oilseed plants having reduced seedpod shatter.

2. Background Information

Across the Upper Midwestern USA tens of millions of acres of farmland are rotated between *Zea mays* L. and *Glycine max* (L.) Merr. Only 2% of this region is typically protected by a cover crop in the fallow period between autumn harvest and the following spring planting. This leaves farmlands across the Midwest vulnerable to nutrient leaching and soil erosion, threatening the sustainability of current farming practices and the health of rural populations. Cover crops such as winter rye (*Secale cereale* L.) that can be grown during the fallow period can greatly reduce nutrient leaching; however, rye provides no economic return.

SUMMARY

This document provides materials and methods for domesticating oilseed (e.g., pennycress) plants. For example, this document provides domesticated oilseed plants having reduced seedpod shatter, as compared to corresponding wild type oilseed plants. This document also provides materials and methods for making and/or using the domesticated oilseed plants described herein (e.g., having reduced seedpod shatter).

As demonstrated herein, loss-of-function modifications in the pennycress SPATULA (SPT), ALCATRAZ (ALC), INDEHISCENT (IND), SHATTERPROOF (SHP; e.g., SHP1 and SHP2), PINOID (PID), and DZ POLYGALACTURONASE (ADPG; e.g., ADPG1 and ADPG2) genes resulted in reduced seedpod shatter as compared to corresponding wild type pennycress plants. Domesticated oilseed plants having reduced seedpod shatter can have increased yield (e.g., increased harvestable plant yield and/or longer harvest-time windows) as compared to corresponding wild type pennycress plants.

Having the ability to design oilseed (e.g., pennycress) plants having reduced seedpod shatter provides a unique and unrealized opportunity to improve the sustainability of current farming practices. For example, oilseed plants provided herein can be grown in the interval between corn harvest and soybean establishment the following spring in the Midwestern United States as well as in other regions and cropping systems, thereby maximizing potential production from land already in use. Oil from the seeds of oilseed plants provided herein can be used as edible oil or used for the production of biodiesel, jet fuel, and other bioproducts. In addition, oilseed plants provided herein can provide ecosystem services such as reducing nutrient leaching and soil erosion and providing food for pollinators. Thus, pennycress plants described here have the potential to reduce nutrient leaching while providing farmers with an oilseed cash crop.

In general, one aspect of this document features an oilseed plant having reduced seedpod shatter (e.g., as compared to a corresponding wild type oilseed plant), where the oilseed plant includes a modification in one or more genes encoding a polypeptide and/or a microRNA involved in seedpod shatter. The oilseed plant can be a pennycress plant. The oilseed plant can include seedpods that require about 20 grams to about 120 grams pulling force to shatter. The oilseed plant can include seedpods that are resistant to shatter under less than about 30 grams force. The modification can be a loss-of-function modification. In some cases, the gene can be a SPT gene. The modified SPT gene can include a single base-pair substitution. The single base-pair substitution can be a C to T substitution at nucleotide residue 157. The modified SPT gene can include the sequence set forth in SEQ ID NO:3. The modified SPT gene can encode a modified SPT polypeptide. The modified SPT polypeptide can include the sequence set forth in SEQ ID NO:4. In some cases, the gene can be a ALC gene. The modified ALC gene can include a 10 base pair deletion and a 4 base pair insertion, wherein said 10 base pair deletion includes deletion of residues 827 to 836. The 4 base pair insertion can be a TCTC insertion following nucleotide residue 827. The modified ALC gene can include the sequence set forth in SEQ ID NO:7. The modified ALC gene can encode a modified ALC polypeptide. The modified ALC polypeptide can be as set forth in SEQ ID NO:8.

In another aspect, this document features an oilseed plant having reduced seedpod shatter (e.g., as compared to a corresponding wild type oilseed plant). The oilseed plant can have a modification in one or more genes encoding a polypeptide and/or a microRNA involved in seedpod shatter. The gene encoding a polypeptide and/or a microRNA involved in seedpod shatter can be selected from the group consisting of SPT, ALC, IND, RPL, SHP1, SHP2, FUL, NST1, NST3, PID, ADPG1, and/or ADPG2. The modified gene can encode a modified polypeptide and/or a modified microRNA. The oilseed plant can be a pennycress plant. The oilseed plant can have seedpods that require about 20 grams to about 120 grams pulling force to shatter. The oilseed plant can have seedpods that are resistant to shatter under less than about 30 grams force. When the gene encoding a polypeptide involved in seedpod shatter is a SPT gene, the modified SPT gene can encode a modified SPT polypeptide. The modified SPT gene can include a C to T substitution at nucleotide residue 157 as set forth in SEQ ID NO:3, and the modified SPT polypeptide can include the amino acid sequence set forth in SEQ ID NO:4. When the gene encoding a polypeptide involved in seedpod shatter is a ALC gene, the modified ALC gene can encode a modified ALC polypeptide. The modified ALC gene can include a 10 base pair deletion of residues 827 to 836 and a TCTC insertion following nucleotide residue 827 as set forth in SEQ ID NO:7, and wherein said modified ALC polypeptide can include the amino acid sequence set forth in SEQ ID NO:8. When the gene encoding a polypeptide involved in seedpod shatter is a IND gene, the modified IND gene can encode a modified IND polypeptide. The modified IND gene can include a C to T substitution at nucleotide residue 247 as set forth in SEQ ID NO:11, and the modified IND polypeptide can include the amino acid sequence set forth in SEQ ID NO:12. The modified IND gene can include a G to A substitution at nucleotide residue 260 as set forth in SEQ ID NO:13, and the modified IND polypeptide can include the amino acid sequence set forth in SEQ ID NO:14. The modified IND gene can include a G to A substitution at nucleotide residue 301 as set forth in SEQ ID NO:15, and the modified IND polypeptide can include the amino acid sequence set forth in SEQ ID NO:16. When the gene encoding a polypeptide involved in seedpod shatter is a SHP1 gene, the modified SHP1 gene can encode a modified SHP1 polypeptide. The modified SHP1 gene can include a G to A substitution at nucleotide residue 17 as set forth in SEQ ID NO:19, and the modified SHP1 polypeptide can include the amino acid sequence set forth in SEQ ID NO:20. When the gene encoding a polypeptide involved in seedpod shatter is a SHP2 gene, the modified SHP2 gene can encode a modified SHP2 polypeptide. The modified SHP2 gene can include a G to A substitution at nucleotide residue 175 as set forth in SEQ ID NO:23, and the modified SHP2 polypeptide can include the amino acid sequence set forth in SEQ ID NO:24. When the gene encoding a polypeptide involved in seedpod shatter is a PID gene, the modified PID gene encodes a modified PID polypeptide. The modified PID gene can include a G to A substitution at nucleotide residue 470 as set forth in SEQ ID NO:27, and the modified PID polypeptide can include the amino acid sequence set forth in SEQ ID NO:28. When the gene encoding a polypeptide involved in seedpod shatter is a ADPG1 gene, the modified ADPG1 gene can encode a modified ADPG1 polypeptide. The modified ADPG1 gene can include single base pair deletion of residue 104 as set forth in SEQ ID NO:31, and the modified ADPG1 polypeptide can include the amino acid sequence set forth in SEQ ID NO:32. The modified ADPG1 gene can include a 4 base pair deletion of residues 101 to 104 as set forth in SEQ ID NO:33, and the modified ADPG1 polypeptide can include the amino acid sequence set forth in SEQ ID NO:34.

In another aspect, this document features a seed produced by an oilseed plant having reduced seedpod shatter (e.g., as compared to a corresponding wild type oilseed plant), where the oilseed plant includes a modification in one or more genes encoding a polypeptide and/or a microRNA involved in seedpod shatter.

In another aspect, this document features a method for generating an oilseed plant having reduced seedpod shatter (e.g., as compared to a corresponding wild type oilseed plant). The method includes, or consists essentially of, modifying a gene in the oilseed plant genome, where the gene encodes a polypeptide and/or a microRNA involved in seedpod shatter, and where the modification is effective to reduce pod shatter in the plant. The modifying can include site-specific editing. The oilseed plant can be a pennycress plant. The oilseed plant can include seedpods that require about 20 grams to about 120 grams pulling force to shatter. The modification can be a loss-of-function modification. In some cases, the gene can be a SPT gene. The modified SPT gene can include a single base-pair substitution (e.g., a C to T substitution) at nucleotide residue 157. The modified SPT gene can include the sequence set forth in SEQ ID NO:3. The modified SPT gene can encode a modified SPT polypeptide. The modified SPT polypeptide can include the sequence set forth in SEQ ID NO:4. In some cases, the gene can be a ALC gene. The modified ALC gene can include a 10 base pair deletion of residues 827 to 836, and a 4 base pair TCTC insertion following nucleotide residue 827. The modified ALC gene can include the sequence set forth in SEQ ID NO:7. The modified ALC gene can encode a modified ALC polypeptide. The modified ALC polypeptide can include the sequence set forth in SEQ ID NO:8.

In another aspect, this document features a method for generating an oilseed plant having reduced seedpod shatter (e.g., as compared to a corresponding wild type oilseed plant). The method includes, or consists essentially of, introducing into an oilseed plant cell a nuclease and a guide sequence, where the guide sequence includes a nucleic acid sequence specific to the ALC gene; selecting an oilseed plant cell having reduced seedpod shatter as compared to a wild oilseed plant; and regenerating an oilseed plant having reduced seedpod shatter from the selected oilseed plant cell. The oilseed plant can be a pennycress plant. The nuclease can be a clustered regularly interspaced short palindromic repeats (CRISPR) associated system (Cas) nuclease. The Cas nuclease can be a Cas9 nuclease. The Cas9 nuclease can be a *Staphylococcus aureus* Cas9. The guide sequence can include SEQ ID NO:53.

In another aspect, this document features a method for generating an oilseed plant having reduced seedpod shatter (e.g., as compared to a corresponding wild type oilseed plant). The method includes, or consists essentially of, modifying one or more genes in the oilseed plant genome, where the gene encodes a polypeptide and/or a microRNA involved in seedpod shatter. The gene that encodes a polypeptide involved in seedpod shatter can be SPT, ALC, IND, RPL, SHP1, SHP2, FUL, NST1, NST3, PID, ADPG1, and/or ADPG2. The modified gene can encode a modified polypeptide. The oilseed plant can be a pennycress plant. The modifying can include site-specific editing. The site-specific editing can include introducing a guide sequence and a nuclease into an oilseed plant cell, where the guide sequence includes a nucleic acid sequence specific to a gene encoding a polypeptide involved in seedpod shatter, and where the nuclease is a Cas nuclease. The modifying can include mutagenesis. The mutagenesis can include introducing a mutagen into an oilseed plant cell. The mutagen can include ethyl methane sulphonate (EMS). The method also can include selecting an oilseed plant cell having reduced seedpod shatter as compared to a wild oilseed plant; and regenerating an oilseed plant having reduced seedpod shatter from the selected oilseed plant cell.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 2A-2D show exemplary SPT sequences. A) A wild type (WT) pennycress SPT nucleotide sequence (SEQ ID NO:1) with lowercase letters indicating introns. B) A WT pennycress SPT polypeptide sequence (SEQ ID NO:2). C) A modified pennycress SPT nucleotide sequence having a C to T substitution at nucleotide residue 157 (SEQ ID NO:3) with the bold, italic T indicating the substitution and the lower case letters indicating introns. D) A modified pennycress SPT polypeptide sequence having a R to W substitution at amino acid residue 53 (SEQ ID NO:4) with the bold, italic W indicating the substitution.

FIGS. 3A-3E show exemplary ALC sequences. A) A WT pennycress ALC nucleotide sequence (SEQ ID NO:5) with lower case letters indicating introns. A protospacer location and PAM site that can be targeted by, for example, CRISPR-SaCas9 gRNA are underlined and in bold (protospacer) or italicized (PAM site). B) A WT pennycress ALC polypeptide sequence (SEQ ID NO:6). C) A modified pennycress ALC nucleotide sequence having a 10 base pair deletion of residues 827 to 836, and a 4 base pair TCTC insertion following nucleotide residue 827 (SEQ ID NO:7) with the bold, italic TCTC indicating the insertion and the bold, strikethrough, lowercase letters indicating the deletion. D) A modified pennycress ALC polypeptide sequence having a deletion of asparagine-proline-methionine-arginine (NPMR) at residues 160-163, and an insertion of isoleucine-serine (IS) at residues 160-161 (SEQ ID NO:8) with the bold, italic IS indicating the substituted amino acids. E) Additional exemplary modified pennycress ALC nucleotide sequences having deletions, insertions, and/or base substitutions induced in the pennycress ALC gene at the CRISPR-SaCas9 gRNA site (mutations highlighted in red) using CRISPR-Cas9 methodology. Sequences shown include, from top to bottom, a fragment of a wild type ALC nucleotide sequence (SEQ ID NO:59), a G to A transition (SEQ ID NO:60), a 6 base pair deletion found in the alc-1 mutant (SEQ ID NO:61), a 9 base pair deletion (SEQ ID NO:62), a 4 base pair deletion in the alc-2 mutant (SEQ ID NO:63), a 4 base pair deletion (SEQ ID NO:64), a 2 base pair deletion in the alc-3 mutant (SEQ ID NO:65), a 6 base pair deletion plus a 5 base pair insertion (SEQ ID NO:66), a 1 base pair insertion in the alc-4 mutant (SEQ ID NO:67), and a 1 base pair insertion (SEQ ID NO:68).

FIGS. 4A-4H show exemplary IND sequences. A) WT pennycress IND nucleotide sequences (SEQ ID NO:9 and SEQ ID NO:69). B) WT pennycress IND polypeptides sequence (SEQ ID NO:10 and SEQ ID NO:70). C) A modified pennycress IND nucleotide sequence having a C to T substitution at nucleotide residue 247 (SEQ ID NO:11) with the bold, italic T indicating the substitution. D) A modified pennycress IND polypeptide sequence having a P to S substitution at amino acid residue 83 (SEQ ID NO:12) with the bold, italic S indicating the substitution. E) A modified pennycress IND nucleotide sequence having a G to A substitution at nucleotide residue 260 (SEQ ID NO:13) with the bold, italic A indicating the substitution. F) A modified pennycress IND polypeptide sequence having a R to H substitution at amino acid residue 87 (SEQ ID NO:14) with the bold, italic H indicating the substitution. G) A modified pennycress IND nucleotide sequence having a G to A substitution at nucleotide residue 301 (SEQ ID NO:15) with the bold, italic G indicating the substitution. H) A modified pennycress IND polypeptide sequence having a A to T substitution at amino acid residue 101 (SEQ ID NO:16) with the bold, italic T indicating the substitution. Residue numbers in FIGS. 4C-4H are with reference to SEQ ID NO:9 or SEQ ID NO:10.

FIGS. 5A-5D show exemplary SHP1 sequences. A) A WT pennycress SHP1 nucleotide sequence (SEQ ID NO:17). B) A WT pennycress SHP1 polypeptide sequence (SEQ ID NO:18). C) A modified pennycress SHP1 nucleotide sequence having a G to A substitution at nucleotide residue 17 (SEQ ID NO:19) with the bold, italic A indicating the substitution. D) A modified pennycress SHP1 polypeptide sequence having a S to N substitution at amino acid residue 6 (SEQ ID NO:20) with the bold, italic N indicating the substitution.

FIGS. 6A-6D show exemplary SHP2 sequences. A) A WT pennycress SHP2 nucleotide sequence (SEQ ID NO:21). B) A WT pennycress SHP2 polypeptide sequence (SEQ ID NO:22). C) A modified pennycress SHP2 nucleotide sequence having a G to A substitution at nucleotide residue 175 (SEQ ID NO:23) with the bold, italic A indicating the substitution. D) A modified pennycress SHP2 polypeptide sequence having an A to T substitution at amino acid residue 59 (SEQ ID NO:24) with the bold, italic T indicating the substitution.

FIGS. 7A-7D show exemplary PID sequences. A) A WT pennycress PID nucleotide sequence (SEQ ID NO:25). B) A WT pennycress PID polypeptide sequence (SEQ ID NO:26). C) A modified pennycress PID nucleotide sequence having a G to A substitution at nucleotide residue 470 (SEQ ID NO:27) with the bold, italic A indicating the substitution. D) A modified pennycress PID polypeptide sequence having a C to Y substitution at amino acid residue 157 (SEQ ID NO:28) with the bold, italic Y indicating the substitution.

FIGS. 8A-8F show exemplary ADPG1 sequences. A) A WT pennycress ADPG1 nucleotide sequence (SEQ ID NO:29). A protospacer location and PAM site that can be targeted by, for example, CRISPR-SaCas9 gRNA are underlined and in bold (protospacer) or italicized (PAM site). B) A WT pennycress ADPG1 polypeptide sequence (SEQ ID NO:30). C) A modified pennycress ADPG1 nucleotide sequence having a single base pair deletion of residue 104 (SEQ ID NO:31) with the bold, strikethrough, lowercase letter indicating the deletion. The aberrant amino acid sequence leading up to the stop codon is highlighted in yellow. D) A modified pennycress ADPG1 polypeptide sequence having a truncation (SEQ ID NO:32) with the aberrant amino acid residues (highlighted in bold; resulting from a frameshift) leading up to the stop codon (highlighted in bold in SEQ ID NO:31). E) A modified pennycress ADPG1 nucleotide sequence having a 4 base pair deletion of residues 101 to 104 (SEQ ID NO:33) with the bold, strikethrough, lowercase letters indicating the deletion. F) A modified pennycress ADPG1 polypeptide sequence having a truncation (SEQ ID NO:34) with the aberrant amino acid residues (highlighted in bold; resulting from a frameshift) leading up to the stop codon (highlighted in bold in SEQ ID NO:33).

FIG. 9 contains a sequence alignment of SPT polypeptides from *Arabidopsis thaliana* (At_SPT; SEQ ID NO:35), *Thlaspi arvense* (Ta_SPT; SEQ ID NO:2), a modified *Thlaspi arvense* (Ta_spt-1; mutant strain A7-129; SEQ ID NO:4), *Glycine max* (Gm_SPT; SEQ ID NO:36), *Oryza sativa* (Os_SPT; SEQ ID NO:37), and *Solanum lycopersicum* (Sl_SPT; SEQ ID NO:38).

FIG. 12 contains a sequence alignment of IND polypeptides from *Arabidopsis thaliana* (At_SPT; SEQ ID NO:39), *Thlaspi arvense* (Ta_SPT; SEQ ID NO:10), a modified *Thlaspi arvense* (Ta_ind-1; mutant strain E5-552; SEQ ID NO:12), a modified *Thlaspi arvense* (Ta_ind-2; mutant strain E5-550; SEQ ID NO:14), a modified *Thlaspi arvense* (Ta_ind-3; mutant strain Spring32_NS; SEQ ID NO:16), *Glycine max* (Gm_IND; SEQ ID NO:40), *Oryza sativa* (Os_IND; SEQ ID NO:41), and *Solanum lycopersicum* (Sl_IND; SEQ ID NO:42).

FIGS. 13A-13F show an analysis of seedpod shatter in pennycress plants. A) Images showing growth chamber-grown mature pods for wild type and rps1-1 mutant (line E42; also referred to as ind-3) pennycress plants. rps1-1 plants grew like wild type. B) Images showing seedpods from wild type and rps1-1 mutant (line E42; also referred to as ind-3) pennycress plants. rps1-1 plants had reduced seedpod shatter compared to wild-type pods. C) Microscopic images of pennycress seedpods from a wild type pennycress plant D) Microscopic images of seedpods from a ind-3 (rps1-1) mutant (line E42) and wild type. rps1-1 pods show no dehiscence zone separation. E) A graph with averages of the amounts of pulling force necessary to break the pods open. Seedpods from a mutant pennycress plant having a modified IND gene (ind-3; also referred to as rps1-1) often tore open within a valve instead of at the dehiscence zone. Asterisks represent significant differences compared to wild type as determined by Student's t-test. Bars represent standard deviations; n=12. F) Greater force is required to break open the seedpods from a mutant pennycress plant having a modified IND gene (lines ind-1 and ind-2). Bars represent standard deviations. Letters that are different represent significant differences based on ANOVA.

FIG. 15 shows an image of an agarose gel containing electrophoresed ALCATRAZ-gene PCR products, amplified from six CRISPR-Cas9 ALCATRAZ $T_2$-generation plants and from wild type; those products were digested with the T7 endonuclease enzyme. T7 endonuclease cuts DNA at sites where base-pair mismatches are present. Therefore, the agarose gel data indicate plant lines ME3, ME5, and ME6 likely have CRISPR-Cas9-induced edits that caused DNA base-pair mismatches. Also shown are DNA sequence chromatograms obtained from sequencing the PCR products derived from plant lines ME3 (SEQ ID NO:43), ME5 (SEQ ID NO:44), ME6 (SEQ ID NO:45), and wild type (SEQ ID NO:46); arrows indicate locations where genome edits had occurred near the PAM site (different mutations were observed on each chromosome pair) resulting in likely loss-of-function mutations including frameshift mutations and the observed reduced seedpod shatter phenotypes.

FIG. 17 contains a sequence alignment of PID polypeptides from *Thlaspi arvense* (Ta_PID; SEQ ID NO:26), a modified *Thlaspi arvense* (Ta_pid-1; mutant strain A7-236; SEQ ID NO:28), *Arabidopsis thaliana* (At_PID; SEQ ID NO:47), *Glycine max* (Gm_IND; SEQ ID NO:48), *Oryza sativa* (Os_IND; SEQ ID NO:49), and *Solanum lycopersicum* (Sl_IND; SEQ ID NO:50).

FIGS. 19A-19C show an analysis of seedpod shatter in pennycress plants. A) A microscopic images of seedpods from a wild type pennycress plant. B) A microscopic images of seedpods from a mutant pennycress plant having a modified ADPG1 gene (line adgp1-2). C) Greater force is required to break open the seedpods from a mutant pennycress plant having a modified ADPG1 gene (lines adpg1-1 and adpg1-2). Asterisks represent significant differences compared to wild type as determined by Student's t-test. Bars represent standard deviations; n=30.

DETAILED DESCRIPTION

Figure 1:
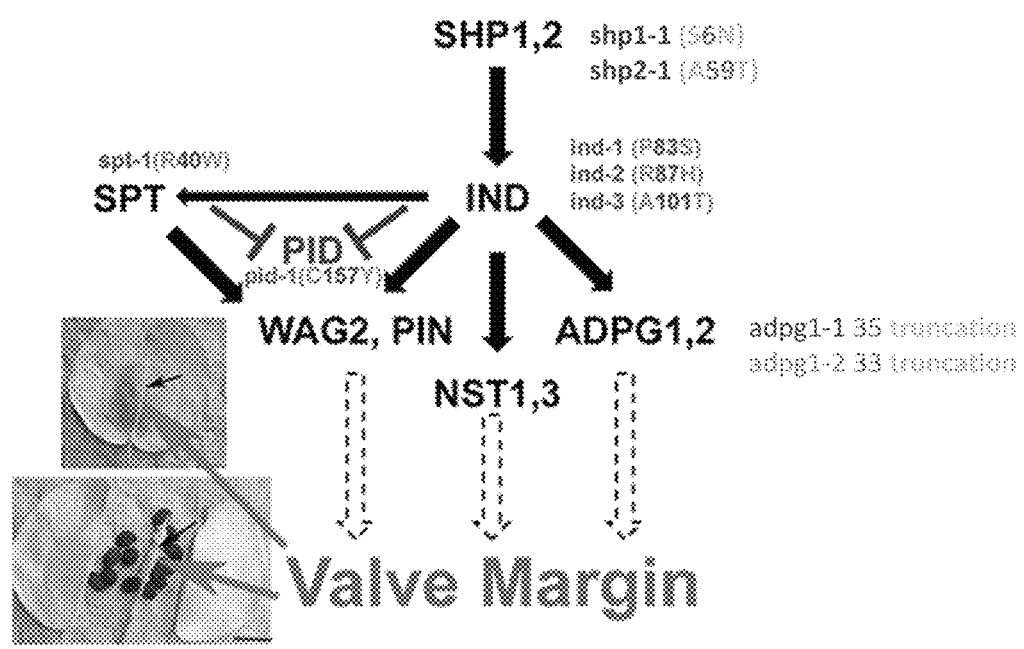
FIG. 1 contains a schematic of the polypeptides controlling the cascade of events leading to formation and a weakening of the layer of cells in the *Arabidopsis* seedpod referred to as the valve margin. This region is highlighted in the corresponding regions of pennycress pods. The weakening allows the pods to readily split as shown. Also shown are the nature of various mutant alleles for most of the genes in the pathway (mutant alleles (purple), (amino acid changes (blue), position of changes in the peptides (red)).

This document provides oilseed (e.g., pennycress) plants having reduced seedpod shatter. In some cases, this document provides oilseed plants having reduced expression levels of one or more polypeptides involved in seedpod shatter (e.g., as compared to corresponding wild type plants). For example, an oilseed plant having reduced seedpod shatter can have a one or more modifications in one or more genes encoding a polypeptide involved in seedpod shatter where the modification(s) are effective to reduce polypeptide expression. In some cases, this document provides oilseed plants having reduced function of one or more polypeptides involved in seedpod shatter (e.g., as compared to corresponding wild type plants). For example, an oilseed plant having reduced seedpod shatter can have one or more modifications in a polypeptide involved in seedpod shatter where the modification(s) are effective to reduce polypeptide function.

This document also provides materials and methods for making and/or using the oilseed plants described herein (e.g., oilseed plants having reduced seedpod shatter). In some cases, mutagenesis (e.g., chemical mutagenesis) can be used to modify one or more genes encoding a polypeptide involved in seedpod shatter. As described herein, mutagenesis can be used to produce an oilseed plant having a loss-of-function modification in a SPT gene, a loss-of-function modification in a IND gene, a loss-of-function modification in one or more SHP genes, and/or a loss-of-function modification in a PID gene. In some cases, site-specific gene editing can be used to modify one or more genes encoding a polypeptide involved in seedpod shatter. As described herein, gene editing techniques (e.g., CRISPR-Cas systems) can be used to produce an oilseed plant having a loss-of-function modification in a ALC gene and/or a loss-of-function modification in an ADPG1 gene. One or more modifications to a gene encoding a polypeptide involved in seedpod shatter in a plantcan be effective to cause a reduced polypeptide expression and/or polypeptide function, thereby reducing seedpod shatter in the plant.

The oilseed plants described herein (e.g., oilseed plants having reduced seedpod shatter) can be used as a cover crop that can reduce nutrient leaching, can reduce soil erosion, and/or can provide nectar and pollen provisions for pollinating insects such as bees.

The oilseed plants described herein (e.g., oilseed plants having reduced seedpod shatter) also can produce an economically viable product (e.g., edible oil, edible meal, and/or oil that can be used for the production of biodiesel, jet fuel, and/or other bioproducts).

The oilseed plants described herein (e.g., oilseed plants having reduced seedpod shatter) can be derived from any appropriate species of oilseed plant. An oilseed plant can be a monocotyledonous oilseed plant. An oilseed plant can be a dicotyledonous oilseed plant. An oilseed plant can be a member of the family Brassicaceae (e.g., the mustard family). For example, an oilseed plant can be a member of the genus *Brassica*. Examples of oilseed plants include, without limitation, pennycress, rapeseed, soybean, sunflower, canola, flax, camelina, *carinata*, *lepidium*, and *crambe* plants. In some cases, a domesticated oilseed plant having reduced seedpod shatter as described herein can be a pennycress plant.

In some cases, oilseed plants provided herein can have reduced seedpod (e.g., seedpod) shatter. The term "reduced seedpod shatter" as used herein with respect to seedpods of an oilseed plant refers to the seedpod requiring a greater amount of force to break open than an amount of force needed to break open a wild type seedpod. It will be appreciated that comparable oilseed plants are used when determining whether or not a particular oilseed plant has reduced seedpod shatter. Reduced seedpod shatter can also be referred to as, for example, increased pod shatter resistance. For example, a seedpod of a wild type pennycress plant typically shatters under about 3 grams to about 20 grams of force (e.g., pulling force). In some cases, a pennycress plant having reduced seedpod shatter as described herein can have seedpods that require greater than about 10 (e.g., greater than about 20, greater than about 30, greater than about 40, greater than about 50, greater than about 60, greater than about 70, greater than about 80, greater than about 90, greater than about 100, greater than about 110, or greater than about 120) grams force (e.g., pulling force) to shatter. In some cases, an oilseed plant having reduced seedpod shatter as described herein can have seedpods that require about 20 grams to about 120 grams (e.g., about 20 grams to about 100 grams, about 20 grams to about 90 grams, about 20 grams to about 80 grams, about 20 grams to about 60 grams, about 20 grams to about 45 grams, about 25 grams to about 120 grams, about 30 grams to about 120 grams, about 40 grams to about 120 grams, about 50 grams to about 120 grams, about 70 grams to about 120 grams, about 100 grams to about 120 grams, about 25 grams to about 100 grams, about 30 grams to about 90 grams, about 40 grams to about 80 grams, or about 50 grams to about 70 grams) force (e.g., pulling force) to shatter. For example, a pennycress plant having reduced seedpod shatter as described herein can have seedpods that require about 20 grams to about 45 grams pulling force to shatter. For example, a pennycress plant having reduced seedpod shatter as described herein can have seedpods that require about 40 grams to about 120 grams pulling force to shatter. In some cases, an oilseed plant having reduced seedpod shatter as described herein can have seedpods that are resistant to shatter under about 10 grams to about 30 grams pulling force. For example, a pennycress plant having reduced seedpod shatter as described herein can have seedpods that are resistant to shatter under less than about 30 (e.g., less than about 25, less than about 20, less than about 18, less than about 15, less than about 12, less than about 10, or less than about 7) grams force (e.g., pulling force). The oilseed plants having reduced seedpod shatter as described herein can be identified by, for example, measuring shatter resistance (e.g., as described in the Examples).

The oilseed plants having reduced seedpod shatter as described herein can be from the A7-129, A7-236, E42, ME3, M5, or ME6 line as described, for example, in the Examples, or can be progeny derived from those lines.

The oilseed plants having reduced seedpod shatter as described herein can include any appropriate type of modification(s) in one or more genes that encode polypeptides involved in seedpod shatter. For example, a modification can be a loss-of-function modification. As used herein, a loss-of-function modification can be any modification that is effective to reduce polypeptide expression or polypeptide function. In some cases, reduced polypeptide expression or reduced polypeptide function can be eliminated polypeptide expression or eliminated polypeptide function. Examples of genetic modifications include, without limitation, deletions, insertions, substitutions, translocations, inversions, and duplications.

The oilseed plants having reduced seedpod shatter as described herein can include one or more modification(s) in any appropriate gene that encodes any appropriate polypeptide involved in seedpod shatter. Gens that encode polypeptides involved in seedpod shatter include, without limitation, SPT, alcatraz (ALC), indehiscent (IND), replumless (RPL), shatterproof (SHP; e.g., SHP1 and SHP2), fruitfull (FUL), nac secondary wall thickening promoting factor1 and 3 (NST1 and NST3), pinoid (PID), and dz polygalacturonase 1 and 2 (ADPG1 and ADPG2). Polypeptides involved in seedpod shatter include, without limitation, SPT, ALC, IND, RPL, SHP (e.g., SHP1 and SHP2), FUL, NST1, NST3, PID, ADPG1, and ADPG2.

In some cases, oilseed plants having reduced seedpod shatter as described herein can include one or more modifications (e.g., one or more loss-of-function modifications) in a SPT gene (e.g., in a SPT coding sequence) such that the one or more modifications are effective to reduce SPT polypeptide expression and/or SPT polypeptide function. A representative wild type pennycress SPT gene (e.g., coding sequence) is as set forth in SEQ ID NO:1.

In some cases, a wild type pennycress SPT gene (e.g., coding sequence) can have a sequence that deviates from the sequence set in SEQ ID NO:1, sometimes referred to as a variant sequence, provided the variant sequence encodes a wild type pennycress SPT polypeptide. A representative wild type pennycress SPT polypeptide is as set forth in SEQ ID NO:2.

In some cases, a wild type pennycress SPT polypeptide can have a sequence that deviates from the polypeptide sequence set forth in SEQ ID NO:2, sometimes referred to as a variant sequence, provided the polypeptide maintains its wild type function. For example, a variant SPT polypeptide can have at least 80 (e.g., at least 85, at least 90, at least 95, at least 98, or at least 99) percent sequence identity to SEQ ID NO:2. For example, a variant SPT polypeptide can have one or more (e.g., 2, 3, 4, 5, 6, 7, 8, 9, or 10) amino acid modifications (e.g., substitutions) relative to SEQ ID NO:2.

In some cases, oilseed plants described herein (e.g., oilseed plants having reduced seedpod shatter) can have one or more modifications in an SPT gene (e.g., coding sequence). For example, a pennycress plant having reduced seedpod shatter can include a substitution (e.g., a single base-pair substitution) relative to the wild type pennycress SPT gene (e.g., coding sequence). In some cases, a modified SPT gene can include a single base-pair substitution of the cytosine (C) at nucleotide residue 157 in a wild type pennycress SPT gene (e.g., SEQ ID NO:1). The C at nucleotide residue 157 can be substituted with any appropriate nucleotide (e.g., thymine (T), adenine (A), and guanine (G)). For example, a single base-pair substitution can be a C to T substitution at nucleotide residue 157 in a wild type pennycress SPT gene (see, e.g., FIG. 2). A representative modified pennycress SPT gene having a loss-of-function single base pair substitution is as set forth in SEQ ID NO:3. In some cases, oilseed plants having reduced seedpod shatter as described herein (e.g., oilseed plants having reduced seedpod shatter) can have one or more modifications in an SPT polypeptide (e.g., an SPT polypeptide encoded by an SPT gene having one or more modifications). For example, a modified pennycress SPT gene (e.g., coding sequence) having a loss-of-function single base pair substitution (e.g., SEQ ID NO:3) can encode a modified SPT polypeptide (e.g., a modified SPT polypeptide having reduced SPT polypeptide expression and/or reduced SPT polypeptide function). For example, a modified pennycress SPT gene having a single base-pair substitution (e.g., SEQ ID NO:3) can encode a modified SPT polypeptide. In some cases, a modified SPT polypeptide can include a substitution of the arginine (R) at amino acid residue 53 in a wild type pennycress SPT protein (e.g., SEQ ID NO:2). The R at residue 53 can be substituted with any appropriate amino acid (e.g., tryptophan (W)). For example, a modified SPT polypeptide can include a single W substituted for the R at amino acid residue 53 in a wild type pennycress SPT polypeptide (see, e.g., FIG. 2). A representative modified pennycress SPT polypeptide is as set forth in SEQ ID NO:4.

In some cases, oilseed plants having reduced seedpod shatter as described herein can include one or more modifications (e.g., one or more loss-of-function modifications) in a ALC gene (e.g., in a ALC coding sequence) such that the one or more modifications are effective to reduce ALC polypeptide expression and/or ALC polypeptide function. A representative wild type pennycress ALC gene (e.g., coding sequence) is as set forth in SEQ ID NO:5. In some cases, a wild type pennycress ALC gene (e.g., coding sequence) can have a sequence that deviates from the sequence set forth in SEQ ID NO:5, sometimes referred to as a variant sequence, provided the variant sequence encodes a wild type pennycress ALC polypeptide. A representative wild type pennycress ALC polypeptide is as set forth in SEQ ID NO:6. In some cases, a wild type pennycress ALC polypeptide can have a sequence that deviates from the polypeptide sequence set forth above (SEQ ID NO:6), sometimes referred to as a variant sequence, provided the polypeptide maintains its wild type function. For example, a ALC polypeptide can have at least 80 (e.g., at least 85, at least 90, at least 95, at least 98, or at least 99) percent sequence identity to SEQ ID NO:6. An ALC polypeptide can have one or more (e.g., 2, 3, 4, 5, 6, 7, 8, 9, or 10) amino acid modifications (e.g., substitutions) relative to SEQ ID NO:6.

In some cases, oilseed plants described herein (e.g., oilseed plants having reduced seedpod shatter) can have one or more modifications in an ALC gene (e.g., coding sequence). For example, a pennycress plant having reduced seedpod shatter can include a deletion and/or an insertion (e.g., a combination of a deletion and an insertion in the location of the deletion) relative to the wild type pennycress ALC gene (e.g., coding sequence). The deletion can include any number of nucleotides (e.g., 1, 2, 3, 4, 5, 6, 7, 8, 9, 10, 11, 12, 13, 14 or 15 nucleotides). For example, a deletion can be a 5 base pair deletion or a 10 base pair deletion (see, e.g., FIG. 15). The insertion can include any appropriate number of nucleotides (e.g., 1, 2, 3, 4, 5, 6, 7, 8, or 9 nucleotides). For example, an insertion can be a 4 base pair insertion or a 5 base pair insertion (see, e.g., FIG. 15). The insertion can include any appropriate nucleotides (e.g., T, A, G, or C) in any appropriate sequence. For example, a 4 base pair insertion can have the sequence TCTC. In some cases, an oilseed plant having reduced seedpod shatter as described herein can include a 10 base pair deletion in a wild type pennycress ALC gene (e.g., SEQ ID NO:5) and a 4 base pair insertion in the location of the deletion. For example, an oilseed plant having reduced seedpod shatter as described herein can include a 10 base pair deletion of residues 827 to 836 in a wild type pennycress ALC gene, and a 4 base pair TCTC insertion following nucleotide residue 827 in a wild type pennycress ALC gene. A representative modified pennycress ALC gene (e.g., coding sequence) having a loss-of-function 4 base pair insertion in the location of a 10 base pair deletion is as set forth in SEQ ID NO:7. In some cases, oilseed plants having reduced seedpod shatter as described herein (e.g., oilseed plants having reduced seedpod shatter) can have one or more modifications in an ALC polypeptide (e.g., an ALC polypeptide encoded by an ALC gene having one or more modifications). For example, a modified pennycress ALC gene (e.g., coding sequence) having a loss-of-function 10 base pair deletion and a 4 base pair insertion in the location of the deletion (e.g., SEQ ID NO:7) can encode a modified ALC polypeptide (e.g., a modified ALC polypeptide having reduced ALC polypeptide expression and/or reduced ALC polypeptide function). In some cases, a modified pennycress ALC gene having a loss-of-function 10 base pair deletion and a 4 base pair insertion in the location of the deletion can encode a modified ALC polypeptide having a deletion of four amino acids, and an insertion of two different amino acids (e.g., SEQ ID NO:8). The deletion can include any number of amino acids (e.g., 1, 2, 3, 4, 5, 6, 7, 8, or 9 amino acids). For example, a deletion can be a 4 amino acid deletion. Any sequence of amino acids can be deleted. For example, the amino acids at residues 160-163 in a wild type pennycress ALC protein (e.g., SEQ ID NO:6) can be deleted. The insertion can include any appropriate number of amino acids (e.g., 1, 2, 3, or 4 amino acids). For example, an insertion can be a 2 amino acid insertion. The insertion can include any appropriate amino acids (e.g., isoleucine (I), serine (S), or W) in any appropriate sequence. For example, a 2 amino acid insertion can have the sequence IS. In some cases, a modified ALC polypeptide can include a deletion of the amino acid sequence asparagine-proline-methionine-arginine (NPMR) at residues 160-163 in a wild type pennycress ALC protein (e.g., SEQ ID NO:6), and an insertion of the amino acid sequence isoleucine-serine (IS) at residues 160-161 in the wild type pennycress ALC protein. A representative modified pennycress ALC polypeptide is as set forth in SEQ ID NO:8.

In some cases, oilseed plants having reduced seedpod shatter as described herein can include one or more modifications (e.g., one or more loss-of-function modifications) in a IND gene (e.g., in a IND coding sequence) such that the one or more modifications are effective to reduce IND polypeptide expression and/or IND polypeptide function. Representative wild type pennycress IND genes (e.g., coding sequences) are as set forth in SEQ ID NO:9 and SEQ ID NO:69. In some cases, a wild type pennycress IND gene (e.g., coding sequence) can have a sequence that deviates from the sequence set in SEQ ID NO:9 or SEQ ID NO:69, sometimes referred to as a variant sequence, provided the variant sequence encodes a wild type pennycress IND polypeptide. Representative wild type pennycress IND polypeptides are as set forth in SEQ ID NO:10 and SEQ ID NO:70. In some cases, a wild type pennycress IND polypeptide can have a sequence that deviates from the polypeptide sequence set forth in SEQ ID NO:10 or SEQ ID NO:70, sometimes referred to as a variant sequence, provided the polypeptide maintains its wild type function. For example, a variant IND polypeptide can have at least 80 (e.g., at least 85, at least 90, at least 95, at least 98, or at least 99) percent sequence identity to SEQ ID NO:10 or SEQ ID NO:70. For example, a variant IND polypeptide can have one or more (e.g., 2, 3, 4, 5, 6, 7, 8, 9, or 10) amino acid modifications (e.g., substitutions) relative to SEQ ID NO:10 or SEQ ID NO:70. In some cases, oilseed plants described herein (e.g., oilseed plants having reduced seedpod shatter) can have one or more modifications in an IND gene (e.g., coding sequence). For example, a pennycress plant having reduced seedpod shatter can include a substitution (e.g., a single base-pair substitution) relative to the wild type pennycress IND gene (e.g., coding sequence). In some cases, a modified IND gene can include a single base-pair substitution of the C at nucleotide residue 247 in a wild type pennycress IND gene (e.g., SEQ ID NO:9). The C at nucleotide residue 247 can be substituted with any appropriate nucleotide (e.g., T, A, and G). For example, a single base-pair substitution can be a C to T substitution at nucleotide residue 247 in a wild type pennycress IND gene (see, e.g., FIG. 4). A representative modified pennycress IND gene having a loss-of-function single base pair substitution is as set forth in SEQ ID NO:11. In some cases, oilseed plants having reduced seedpod shatter as described herein (e.g., oilseed plants having reduced seedpod shatter) can have one or more modifications in an IND polypeptide (e.g., an IND polypeptide encoded by an IND gene having one or more modifications). For example, a modified pennycress IND gene (e.g., coding sequence) having a loss-of-function single base pair substitution (e.g., SEQ ID NO:11) can encode a modified IND polypeptide (e.g., a modified IND polypeptide having reduced IND polypeptide expression and/or reduced IND polypeptide function). For example, a modified pennycress IND gene having a single base-pair substitution (e.g., SEQ ID NO:11) can encode a modified IND polypeptide. In some cases, a modified IND polypeptide can include a substitution of the proline (P) at amino acid residue 83 in a wild type pennycress IND protein (e.g., SEQ ID NO:10). The P at residue 83 can be substituted with any appropriate amino acid (e.g., serine (S)). For example, a modified IND polypeptide can include a single S substituted for the P at amino acid residue 83 in a wild type pennycress IND polypeptide (see, e.g., FIG. 4). A representative modified pennycress IND polypeptide is as set forth in SEQ ID NO:12. In some cases, a modified pennycress IND gene can have a modification as described relative to SEQ ID NO:9 in the corresponding residue in SEQ ID NO:69. In some cases, a modified pennycress IND polypeptide can have a modification as described relative to SEQ ID NO:10 in the corresponding residue in SEQ ID NO:70.

In some cases, a modified IND gene can include a single base-pair substitution of the G at nucleotide residue 260 in a wild type pennycress IND gene (e.g., SEQ ID NO:9). The G at nucleotide residue 260 can be substituted with any appropriate nucleotide (e.g., T, A, and C). For example, a single base-pair substitution can be a G to A substitution at nucleotide residue 260 in a wild type pennycress IND gene (see, e.g., FIG. 4). A representative modified pennycress IND gene having a loss-of-function single base pair substitution is as set forth in SEQ ID NO:13. In some cases, oilseed plants having reduced seedpod shatter as described herein (e.g., oilseed plants having reduced seedpod shatter) can have one or more modifications in an IND polypeptide (e.g., an IND polypeptide encoded by an IND gene having one or more modifications). For example, a modified pennycress IND gene (e.g., coding sequence) having a loss-of-function single base pair substitution (e.g., SEQ ID NO:13) can encode a modified IND polypeptide (e.g., a modified IND polypeptide having reduced IND polypeptide expression and/or reduced IND polypeptide function). For example, a modified pennycress IND gene having a single base-pair substitution (e.g., SEQ ID NO:13) can encode a modified IND polypeptide. In some cases, a modified IND polypeptide can include a substitution of the arginine (R) at amino acid residue 87 in a wild type pennycress IND protein (e.g., SEQ ID NO:10). The F at residue 87 can be substituted with any appropriate amino acid (e.g., histidine (H)). For example, a modified IND polypeptide can include a single H substituted for the R at amino acid residue 87 in a wild type pennycress IND polypeptide (see, e.g., FIG. 4). A representative modified pennycress IND polypeptide is as set forth in SEQ ID NO:14. In some cases, a modified pennycress IND gene can have a modification as described relative to SEQ ID NO:9 in the corresponding residue in SEQ ID NO:69. In some cases, a modified pennycress IND polypeptide can have a modification as described relative to SEQ ID NO:10 in the corresponding residue in SEQ ID NO:70.

In some cases, a modified IND gene can include a single base-pair substitution of the A at nucleotide residue 301 in a wild type pennycress IND gene (e.g., SEQ ID NO:9). The A at nucleotide residue 301 can be substituted with any appropriate nucleotide (e.g., T, G, and C). For example, a single base-pair substitution can be a G to A substitution at nucleotide residue 301 in a wild type pennycress IND gene (see, e.g., FIG. 4). A representative modified pennycress IND gene having a loss-of-function single base pair substitution is as set forth in SEQ ID NO:15. In some cases, oilseed plants having reduced seedpod shatter as described herein (e.g., oilseed plants having reduced seedpod shatter) can have one or more modifications in an IND polypeptide (e.g., an IND polypeptide encoded by an IND gene having one or more modifications). For example, a modified pennycress IND gene (e.g., coding sequence) having a loss-of-function single base pair substitution (e.g., SEQ ID NO:15) can encode a modified IND polypeptide (e.g., a modified IND polypeptide having reduced IND polypeptide expression and/or reduced IND polypeptide function). For example, a modified pennycress IND gene having a single base-pair substitution (e.g., SEQ ID NO:15) can encode a modified IND polypeptide. In some cases, a modified IND polypeptide can include a substitution of the alanine (A) at amino acid residue 101 in a wild type pennycress IND protein (e.g., SEQ ID NO:10). The A at residue 101 can be substituted with any appropriate amino acid (e.g., threonine (T)). For example, a modified IND polypeptide can include a single T substituted for the A at amino acid residue 101 in a wild type pennycress IND polypeptide (see, e.g., FIG. 4). A representative modified pennycress IND polypeptide is as set forth in SEQ ID NO:16. In some cases, a modified pennycress IND gene can have a modification as described relative to SEQ ID NO:9 in the corresponding residue in SEQ ID NO:69. In some cases, a modified pennycress IND polypeptide can have a modification as described relative to SEQ ID NO:10 in the corresponding residue in SEQ ID NO:70.

In some cases, sequences of modified IND genes and modified IND polypeptides can be as described elsewhere (see, e.g., Girin et al., 2010, *Plant J.*, 63:329-338).

In some cases, sequences of modified RPL genes and modified RPL polypeptides can be as described elsewhere (see, e.g., Roeder et al., 2003, *Curr. Biol.*, 13:1630-1635).

In some cases, oilseed plants having reduced seedpod shatter as described herein can include one or more modifications (e.g., one or more loss-of-function modifications) in a SHP1 gene (e.g., in a SHP1 coding sequence) such that the one or more modifications are effective to reduce SHP1 polypeptide expression and/or SHP1 polypeptide function. A representative wild type pennycress SHP1 gene (e.g., coding sequence) is as set forth in SEQ ID NO:17. In some cases, a wild type pennycress SHP1 gene (e.g., coding sequence) can have a sequence that deviates from the sequence set in SEQ ID NO:17, sometimes referred to as a variant sequence, provided the variant sequence encodes a wild type pennycress SHP1 polypeptide. A representative wild type pennycress SHP1 polypeptide is as set forth in SEQ ID NO:18. In some cases, a wild type pennycress SHP1 polypeptide can have a sequence that deviates from the polypeptide sequence set forth in SEQ ID NO:18, sometimes referred to as a variant sequence, provided the polypeptide maintains its wild type function. For example, a variant SHP1 polypeptide can have at least 80 (e.g., at least 85, at least 90, at least 95, at least 98, or at least 99) percent sequence identity to SEQ ID NO:18. For example, a variant SHP1 polypeptide can have one or more (e.g., 2, 3, 4, 5, 6, 7, 8, 9, or 10) amino acid modifications (e.g., substitutions) relative to SEQ ID NO:18.

In some cases, oilseed plants described herein (e.g., oilseed plants having reduced seedpod shatter) can have one or more modifications in an SHP1 gene (e.g., coding sequence). For example, a pennycress plant having reduced seedpod shatter can include a substitution (e.g., a single base-pair substitution) relative to the wild type pennycress SHP1 gene (e.g., coding sequence). In some cases, a modified SHP1 gene can include a single base-pair substitution of the G at nucleotide residue 17 in a wild type pennycress SHP1 gene (e.g., SEQ ID NO:17). The G at nucleotide residue 17 can be substituted with any appropriate nucleotide (e.g., T, A, and C). For example, a single base-pair substitution can be a G to A substitution at nucleotide residue 17 in a wild type pennycress SHP1 gene (see, e.g., FIG. 5). A representative modified pennycress SHP1 gene having a loss-of-function single base pair substitution is as set forth in SEQ ID NO:19. In some cases, oilseed plants having reduced seedpod shatter as described herein (e.g., oilseed plants having reduced seedpod shatter) can have one or more modifications in an SHP1 polypeptide (e.g., an SHP1 polypeptide encoded by an SHP1 gene having one or more modifications). For example, a modified pennycress SHP1 gene (e.g., coding sequence) having a loss-of-function single base pair substitution (e.g., SEQ ID NO:19) can encode a modified SHP1 polypeptide (e.g., a modified SHP1 polypeptide having reduced SHP1 polypeptide expression and/or reduced SHP1 polypeptide function). For example, a modified pennycress SHP1 gene having a single base-pair substitution (e.g., SEQ ID NO:19) can encode a modified SHP1 polypeptide. In some cases, a modified SHP1 polypeptide can include a substitution of the serine (S) at amino acid residue 6 in a wild type pennycress SHP1 protein (e.g., SEQ ID NO:18). The S at residue 6 can be substituted with any appropriate amino acid (e.g., asparagine (N)). For example, a modified SHP1 polypeptide can include a single S substituted for the S at amino acid residue 6 in a wild type pennycress SHP1 polypeptide (see, e.g., FIG. 5). A representative modified pennycress SHP1 polypeptide is as set forth in SEQ ID NO:20. In some cases, sequences of modified SHP1 genes and modified SHP1 polypeptides can be as described elsewhere (see, e.g., Liljegren et al., 2000, *Nature*, 404:766-770).

In some cases, oilseed plants having reduced seedpod shatter as described herein can include one or more modifications (e.g., one or more loss-of-function modifications) in a SHP2 gene (e.g., in a SHP2 coding sequence) such that the one or more modifications are effective to reduce SHP2 polypeptide expression and/or SHP1 polypeptide function. A representative wild type pennycress SHP2 gene (e.g., coding sequence) is as set forth in SEQ ID NO:21. In some cases, a wild type pennycress SHP2 gene (e.g., coding sequence) can have a sequence that deviates from the sequence set in SEQ ID NO:21, sometimes referred to as a variant sequence, provided the variant sequence encodes a wild type pennycress SHP2 polypeptide. A representative wild type pennycress SHP2 polypeptide is as set forth in SEQ ID NO:22. In some cases, a wild type pennycress SHP2 polypeptide can have a sequence that deviates from the polypeptide sequence set forth in SEQ ID NO:22, sometimes referred to as a variant sequence, provided the polypeptide maintains its wild type function. For example, a variant SHP2 polypeptide can have at least 80 (e.g., at least 85, at least 90, at least 95, at least 98, or at least 99) percent sequence identity to SEQ ID NO:22. For example, a variant SHP2 polypeptide can have one or more (e.g., 2, 3, 4, 5, 6, 7, 8, 9, or 10) amino acid modifications (e.g., substitutions) relative to SEQ ID NO:22.

In some cases, oilseed plants described herein (e.g., oilseed plants having reduced seedpod shatter) can have one or more modifications in an SHP2 gene (e.g., coding sequence). For example, a pennycress plant having reduced seedpod shatter can include a substitution (e.g., a single base-pair substitution) relative to the wild type pennycress SHP2 gene (e.g., coding sequence). In some cases, a modified SHP2 gene can include a single base-pair substitution of the G at nucleotide residue 175 in a wild type pennycress SHP2 gene (e.g., SEQ ID NO:21). The G at nucleotide residue 175 can be substituted with any appropriate nucleotide (e.g., T, A, and C). For example, a single base-pair substitution can be a G to A substitution at nucleotide residue 175 in a wild type pennycress SHP2 gene (see, e.g., FIG. 6). A representative modified pennycress SHP2 gene having a loss-of-function single base pair substitution is as set forth in SEQ ID NO:23. In some cases, oilseed plants having reduced seedpod shatter as described herein (e.g., oilseed plants having reduced seedpod shatter) can have one or more modifications in an SHP2 polypeptide (e.g., an SHP2 polypeptide encoded by an SHP2 gene having one or more modifications). For example, a modified pennycress SHP2 gene (e.g., coding sequence) having a loss-of-function single base pair substitution (e.g., SEQ ID NO:23) can encode a modified SHP2 polypeptide (e.g., a modified SHP2 polypeptide having reduced SHP2 polypeptide expression and/or reduced SHP2 polypeptide function). For example, a modified pennycress SHP2 gene having a single base-pair substitution (e.g., SEQ ID NO:23) can encode a modified SHP2 polypeptide. In some cases, a modified SHP2 polypeptide can include a substitution of the alanine (A) at amino acid residue 59 in a wild type pennycress SHP2 protein (e.g., SEQ ID NO:22). The A at residue 59 can be substituted with any appropriate amino acid (e.g., threonine (T)). For example, a modified SHP2 polypeptide can include a single T substituted for the A at amino acid residue 59 in a wild type pennycress SHP2 polypeptide (see, e.g., FIG. 6). A representative modified pennycress SHP2 polypeptide is as set forth in SEQ ID NO:24. In some cases, sequences of modified SHP2 genes and modified SHP2 polypeptides can be as described elsewhere (see, e.g., Liljegren et al., 2000, *Nature,* 404:766-770).

In some cases, sequences of modified FUL genes and modified FUL polypeptides can be as described elsewhere (see, e.g., Ferrándiz et al., 2000, *Science,* 289:436-438).

In some cases, oilseed plants having reduced seedpod shatter as described herein can include one or more modifications (e.g., one or more loss-of-function modifications) in a PID gene (e.g., in a PID coding sequence) such that the one or more modifications are effective to reduce PID polypeptide expression and/or PID polypeptide function. A representative wild type pennycress PID gene (e.g., coding sequence) is as set forth in SEQ ID NO:25. In some cases, a wild type pennycress PID gene (e.g., coding sequence) can have a sequence that deviates from the sequence set in SEQ ID NO:25, sometimes referred to as a variant sequence, provided the variant sequence encodes a wild type pennycress PID polypeptide. A representative wild type pennycress PID polypeptide is as set forth in SEQ ID NO:26. In some cases, a wild type pennycress PID polypeptide can have a sequence that deviates from the polypeptide sequence set forth in SEQ ID NO:26, sometimes referred to as a variant sequence, provided the polypeptide maintains its wild type function. For example, a variant PID polypeptide can have at least 80 (e.g., at least 85, at least 90, at least 95, at least 98, or at least 99) percent sequence identity to SEQ ID NO:26. For example, a variant PID polypeptide can have one or more (e.g., 2, 3, 4, 5, 6, 7, 8, 9, or 10) amino acid modifications (e.g., substitutions) relative to SEQ ID NO:26.

In some cases, oilseed plants described herein (e.g., oilseed plants having reduced seedpod shatter) can have one or more modifications in a PID gene (e.g., coding sequence). For example, a pennycress plant having reduced seedpod shatter can include a substitution (e.g., a single base-pair substitution) relative to the wild type pennycress PID gene (e.g., coding sequence). In some cases, a modified PID gene can include a single base-pair substitution of the G at nucleotide residue 470 in a wild type pennycress PID gene (e.g., SEQ ID NO:25). The G at nucleotide residue 470 can be substituted with any appropriate nucleotide (e.g., T, A, and C). For example, a single base-pair substitution can be a G to A substitution at nucleotide residue 470 in a wild type pennycress PID gene (see, e.g., FIG. 7). A representative modified pennycress PID gene having a loss-of-function single base pair substitution is as set forth in SEQ ID NO:27. In some cases, oilseed plants having reduced seedpod shatter as described herein (e.g., oilseed plants having reduced seedpod shatter) can have one or more modifications in a PID polypeptide (e.g., a PID polypeptide encoded by a PID gene having one or more modifications). For example, a modified pennycress PID gene (e.g., coding sequence) having a loss-of-function single base pair substitution (e.g., SEQ ID NO:27) can encode a modified PID polypeptide (e.g., a modified PID polypeptide having reduced PID polypeptide expression and/or reduced PID polypeptide function). For example, a modified pennycress PID gene having a single base-pair substitution (e.g., SEQ ID NO:27) can encode a modified PID polypeptide. In some cases, a modified PID polypeptide can include a substitution of the cysteine (C) at amino acid residue 157 in a wild type pennycress PID protein (e.g., SEQ ID NO:26). The C at residue 157 can be substituted with any appropriate amino acid (e.g., tyrosine (Y)). For example, a modified PID polypeptide can include a single Y substituted for the C at amino acid residue 157 in a wild type pennycress PID polypeptide (see, e.g., FIG. 7). A representative modified pennycress PID polypeptide is as set forth in SEQ ID NO:28.

In some cases, oilseed plants having reduced seedpod shatter as described herein can include one or more modifications (e.g., one or more loss-of-function modifications) in a ADPG1 gene (e.g., in a ADPG1 coding sequence) such that the one or more modifications are effective to reduce ADPG1 polypeptide expression and/or ADPG1 polypeptide function. A representative wild type pennycress ADPG1 gene (e.g., coding sequence) is as set forth in SEQ ID NO:29. In some cases, a wild type pennycress ADPG1 gene (e.g., coding sequence) can have a sequence that deviates from the sequence set in SEQ ID NO:29, sometimes referred to as a variant sequence, provided the variant sequence encodes a wild type pennycress ADPG1 polypeptide. A representative wild type pennycress ADPG1 polypeptide is as set forth in SEQ ID NO:30. In some cases, a wild type pennycress ADPG1 polypeptide can have a sequence that deviates from the polypeptide sequence set forth in SEQ ID NO:30, sometimes referred to as a variant sequence, provided the polypeptide maintains its wild type function. For example, a variant ADPG1 polypeptide can have at least 80 (e.g., at least 85, at least 90, at least 95, at least 98, or at least 99) percent sequence identity to SEQ ID NO:30. For example, a variant ADPG1 polypeptide can have one or more (e.g., 2, 3, 4, 5, 6, 7, 8, 9, or 10) amino acid modifications (e.g., substitutions) relative to SEQ ID NO:30.

In some cases, oilseed plants having reduced seedpod shatter as described herein (e.g., oilseed plants having reduced seedpod shatter) can have one or more modifications in an ADPG1 gene (e.g., coding sequence). For example, a pennycress plant having reduced seedpod shatter can include a deletion relative to the wild type pennycress ALC gene (e.g., coding sequence). The deletion can include any number of nucleotides (e.g., 1, 2, 3, 4, 5, 6, 7, 8, 9, 10, 11, 12, 13, 14 or 15 nucleotides). For example, a deletion can be a single base pair deletion or a 4 base pair deletion (see, e.g., FIG. 8). In some cases, an oilseed plant having reduced seedpod shatter as described herein can include a single base pair deletion in a wild type pennycress ADPG1 gene (e.g., SEQ ID NO:29). For example, an oilseed plant having reduced seedpod shatter as described herein can include a single base pair deletion of residue 104 in a wild type pennycress ADPG1 gene. A representative modified pennycress ALC gene (e.g., coding sequence) having a loss-of-function single base pair deletion is as set forth in SEQ ID NO:31. In some cases, oilseed plants having reduced seedpod shatter as described herein (e.g., oilseed plants having reduced seedpod shatter) can have one or more modifications in an ADPG1 polypeptide (e.g., an ADPG1 polypeptide encoded by an ADPG1 gene having one or more modifications). For example, a modified pennycress ADPG1 gene (e.g., coding sequence) having a loss-of-function single base pair deletion (e.g., SEQ ID NO:31) can encode a modified ADPG1 polypeptide (e.g., a modified ADPG1 polypeptide having reduced ADPG1 polypeptide expression and/or reduced ADPG1 polypeptide function). In some cases, a modified pennycress ADPG1 gene having a loss-of-function single base pair deletion can encode a modified ADPG1 polypeptide that is truncated relative to a wild type ADPG1 polypeptide (e.g., SEQ ID NO:30). In some cases, a single base pair deletion can result in a frameshift such that a modified ADPG1 polypeptide can include an aberrant amino acid sequence (e.g., an aberrant C-terminal amino acid sequence). A representative modified pennycress ALC polypeptide is as set forth in SEQ ID NO:32.

In some cases, an oilseed plant having reduced seedpod shatter as described herein can include a 4 base pair deletion in a wild type pennycress ADPG1 gene (e.g., SEQ ID NO:29). For example, an oilseed plant having reduced seedpod shatter as described herein can include a 4 base pair deletion of residues 101 to 104 in a wild type pennycress ADPG1 gene. A representative modified pennycress ALC gene (e.g., coding sequence) having a loss-of-function single base pair deletion is as set forth in SEQ ID NO:33. In some cases, oilseed plants having reduced seedpod shatter as described herein (e.g., oilseed plants having reduced seedpod shatter) can have one or more modifications in an ADPG1 polypeptide (e.g., an ADPG1 polypeptide encoded by an ADPG1 gene having one or more modifications). For example, a modified pennycress ADPG1 gene (e.g., coding sequence) having a loss-of-function 4 base pair deletion (e.g., SEQ ID NO:33) can encode a modified ADPG1 polypeptide (e.g., a modified ADPG1 polypeptide having reduced ADPG1 polypeptide expression and/or reduced ADPG1 polypeptide function). In some cases, a modified pennycress ADPG1 gene having a loss-of-function 4 base pair deletion can encode a modified ADPG1 polypeptide that is truncated relative to a wild type ADPG1 polypeptide (e.g., SEQ ID NO:30). In some cases, a 4 base pair deletion can result in a frameshift such that a modified ADPG1 polypeptide can include an aberrant amino acid sequence (e.g., an aberrant C-terminal amino acid sequence). A representative modified pennycress ALC polypeptide is as set forth in SEQ ID NO:34.

Any appropriate method can be used to introduce one or more modifications into a gene encoding a polypeptide involved in seedpod shatter to produce oilseed plants described herein (e.g., oilseed plants having reduced seedpod shatter).

In some cases, mutagenesis (e.g., chemical mutagenesis) can be used to produce oilseed plants having reduced seedpod shatter. For example, mutagenesis can be used to modify one or more genes encoding a polypeptide involved in seedpod shatter. Mutagenesis can be performed using any appropriate mutagen. A mutagen can be a chemical mutagen. Examples of mutagens that can be used to produce oilseed plants having reduced seedpod shatter include, without limitation, ethyl methane sulphonate (EMS), 1-methyl-1-nitrosourea, 1-ethyl-1-nitrosourea, fast neutrons (FN), gamma rays, x-rays, ultraviolet light, T-DNAs, RNA interference (RNAi), and micro RNAs. For example, EMS can be used to induce G to A substitutions and/or C to T substitutions in a nucleotide sequence. In cases where mutagenesis is used to produce oilseed plants having one or more modifications in a gene encoding a polypeptide involved in seedpod shatter, one or more genes encoding a polypeptide involved in seedpod shatter and/or one or more polypeptides involved in seedpod shatter can be sequenced to determine whether or not a modification described herein (e.g., a modification effective to result in reduced seedpod shatter) is present.

Figure 3E:

In some cases, genome editing can be used to produce oilseed plants having reduced seedpod shatter. For example, genome editing can be used to modify one or more genes encoding a polypeptide involved in seedpod shatter. Genome editing, or genome editing with engineered nucleases (GEEN) can insert, replace, or remove DNA from a genome using one or more site-specific nucleases (SSN) and, in some cases, a repair template (RT). Nucleases can be targeted to a specific position in the genome, where their action can introduce a particular modification to the endogenous sequences. For example, a SSN can introduce a targeted double-strand break (DSB) in the genome, such that cellular DSB repair mechanisms incorporate a RT into the genome in a configuration that produces heritable glyphosate resistance in the cell, in a plant regenerated from the cell, and in any progeny of the regenerated plant. Nucleases useful for genome editing include, without limitation, CRISPR-associated nucleases (e.g., Cas9, SpCas9, SaCas9, and Cpf1), zinc finger nucleases (ZFNs), transcription activator-like effector nucleases (TALE nucleases), and homing endonucleases (HE; also referred to as meganucleases). For example, a CRISPR-Cas9 system can be used to introduce one or more loss-of-function modifications described herein into a gene (e.g., coding sequence) encoding a polypeptide involved in seedpod shatter. For example, a CRISPR-Cas9 vector can include at least one guide sequence specific to a wild type pennycress ALC sequence (see, e.g., SEQ ID NO:5, FIG. 3, and Example 3) and/or at least one guide sequence specific to a pennycress ADPG1 sequence (see, e.g., SEQ ID NO:29, FIG. 8, and Example 4) upstream of a PAM. A Cas enzyme will bind to and cleave within the gene only if the target site is followed by a PAM sequence. For example, the canonical PAM is the sequence 5'-NGG-3', where N is any nucleotide followed by two guanine (G) nucleotides. The Cas9 component of a CRISPR-Cas9 system designed to introduce one or more loss-of-function modifications described herein can be any appropriate Cas9. In some cases, the Cas9 of a CRISPR-Cas9 system described herein can be a *Staphylococcus aureus* Cas9 (SaCas9). One example of a SaCas9 is described in, for example, Steinert et al., 2015 *Plant J.* 84:1295-305.

The genome editing reagents described herein can be introduced into an oilseed plant by any appropriate method. In some cases, nucleic acids encoding the genome editing reagents can be introduced into a plant cell using *Agrobacterium* or Ensifer mediated transformation, particle bombardment, liposome delivery, nanoparticle delivery, electroporation, polyethylene glycol (PEG) transformation, or any other method suitable for introducing a nucleic acid into a plant cell. In some cases, the SSN or other expressed gene editing reagents can be delivered as RNAs or as proteins to a plant cell and the RT, if one is used, can be delivered as DNA.

The invention will be further described in the following examples, which do not limit the scope of the invention described in the claims.

EXAMPLES

Example 1: Domesticated Pennycress Plants

To identify domestication genes in pennycress plants, pennycress seeds were mutagenized with several different mutagens, including ethyl methanesulfonate (EMS), fast neutrons (FN) and gamma rays (γ rays). Treatment of dry plant seeds with mutagens results in the generation of distinct sets of mutations in every cell in the seed. The fate of many of these cells can be followed when a mutation in one of these cells results in a visible phenotype creating a marked plant sector. For example, mutations that induce the formation of either yellow or pale sectors have been used to generate embryonic cellular fate maps in *Arabidopsis*. These fate maps make predictions about the contribution of cells in the embryonic meristem to development of subsequent plant structures. The largest of such sectors can be used to estimate the number of cells (known as the genetically effective cells) that give rise to the gametes in the treated dry M1 seeds. In such sectors, both the pollen and egg cells share common progenitor cells. After meiosis in commonly derived anthers and ovules, one quarter of the seeds will be homozygous for any mutations carried in common progenitor cells. Sectors similar to those seen in mutagenized *Arabidopsis* populations were observed in the EMS mutagenized M1 pennycress plants. The largest sectors observed in pennycress encompassed approximately a third of the floral meristem, which is consistent with the presence of three genetically effective cells in the dry seed. Thus, a pool of seeds collected from 10 M1 plants would represent approximately 30 different mutagenic events.

Pennycress plants exhibiting domestication enabling traits such as reduced seedpod shatter were analyzed and loss of function mutations in domestication genes were identified.
Materials and Methods
Mutagenesis (EMS, FN, and Gamma Ray).

Figures 10A, 10B, 10C:
FIGS. 10A-10G show an analysis of seedpod shatter in pennycress plants. A-C) Images showing field grown mature pods from wild type pennycress plants (A), a mutant pennycress plant having a modified SPT gene (line MNA7-129) (B), and a mutant pennycress plant having a modified SPT gene (line MNA7-236)(C). D) A gene model for a mutant pennycress plant having a modified SPT gene (line MNA7-129). E) A graph showing losses due to shatter induced by environmental conditions or by mechanical harvest machinery. F) A graph showing gram-force needed to break open wild type (line MN 106) and mutant (lines MNA7-129 and MNA7-236) seedpods. G) Greater force is required to break open the seedpods of the mutant pennycress plants having a modified SPT gene.
Figure 10D:
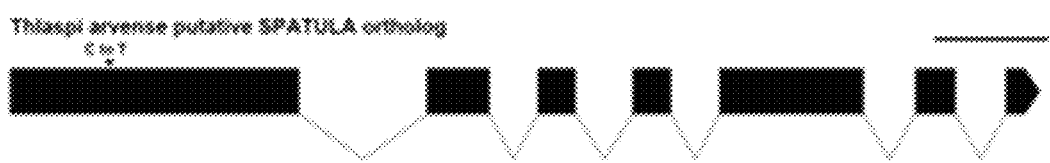
Figure 10E:
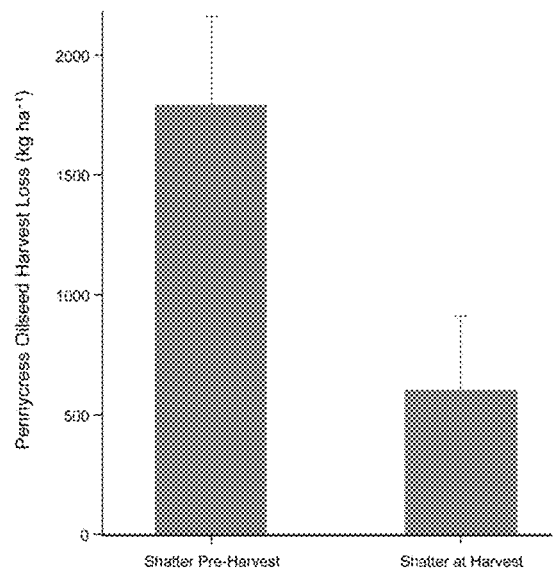

Seeds treated with 0.2% EMS showed somatic chlorophyll sectoring in the leaves (comparable to what is seen with EMS mutagenized *Arabidopsis*) and all of the treated plants set seeds. Approximately 40,000 seeds were treated with EMS and planted in the field. The seeds germinated and a stand of pennycress was established. Approximately 1-2% of the seedlings showed somatic chlorophyll sectoring in the leaves. In addition to EMS, batches of seeds (40,000 per batch) were exposed to different levels of fast neutrons and gamma rays. Seeds were treated with gamma rays with levels ranging from 5 to 45 kilorads (kR) and were treated with fast neutrons (FN) with levels from 8 to 30 gray (Gy). All treated seeds germinated at similar levels and some somatic sectors were noted in seedlings treated with 30 Gy FN. These seeds were considered to be the progenitors of the M1 generation of plants.
Growth of Plants Winter annual pennycress mutagenized M1 seeds were planted into small plots during the summer. In addition, M1 seeds from an EMS treated spring line were grown in growth chambers. M2 seeds were collected from mutagenized M1 plants and were either grown in the field or in growth chambers. The resulting M2 plants were screened for interesting morphological traits such as altered growth, early flowering and senescence, shatter resistance, and reduced stature. In addition, M3 seeds were collected from approximately 15,000 randomly selected individual M2 plants.
Impact of Shatter in the Field Images were taken of field grown wild type and mutant plants at a time past normal harvest date (FIGS. 2C-D). To measure pre harvest losses due to environmental conditions, plastic containing of known area were place under the canopy of wild type pennycress plants two weeks prior to normal harvest date. Weight of seeds that dropped pre harvest into the container divided by the container area were converted to kg/ha as shown in FIG. 10E. New plastic container were placed in the field immediately prior to harvest. Seeds that dropped into the containing during the harvest were used to calculate loss during harvest as shown in FIG. 10E.
Measuring Shatter Resistance Shatter resistance was quantitatively measured using a gram force meter attached to an alligator clip. One lateral side of a pod was clipped and the other side was manually pulled until the pod split apart at the septum. The maximum force recorded by the meter was consider the force needed to break open the pod.
Sequencing PCR primers were designed to amplify the candidate pennycress genes (Table 1) and the products were subject to Sanger sequencing.

TABLE 1

PCR primers.

| primer | forward primer sequence | SEQ ID NO: | reverse primer sequence | SEQ ID NO: |
|---|---|---|---|---|
| SPT | GGGCAATGTTATTACCTCCG | 51 | GGCTCTATGACAGACCAATC | 52 |

Results

Figure 10F:
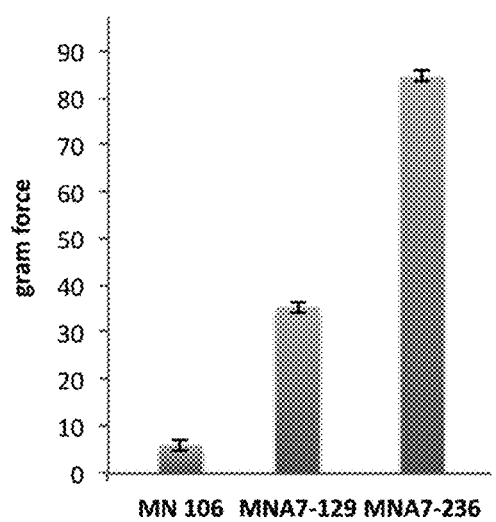
Figure 10G:
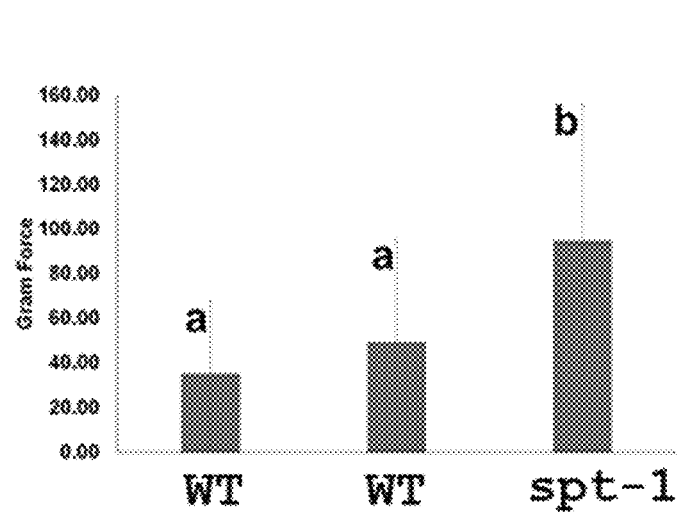
Figure 11A:
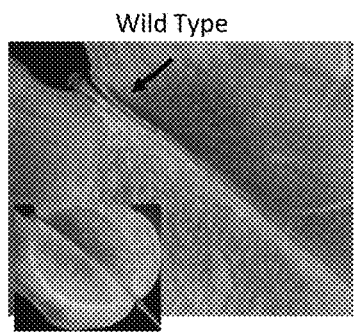
FIGS. 11A-11E show an analysis of seedpod shatter in pennycress plants. A-C) Microscopic images of seedpods from a wild type pennycress plant (A), mutant pennycress plant having a modified ALCATRAZ gene (line ME5) (B), and seedpods from a mutant pennycress plant having a modified ALCATRAZ gene (line alc-4) (C). D) A graph with averages of the amounts of pulling force necessary to break the pods open. Asterisks represent significant differences compared to wild type as determined by Student's t-test. Bars represent standard deviations; n=12. E) Greater force is required to break open the seedpods from a mutant pennycress plant having a modified ALCATRAZ gene (lines alc-1, alc-2, alc-3, and alc-4).
Figure 11B:
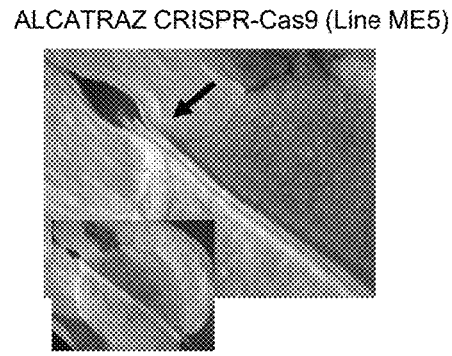
Figure 11C:
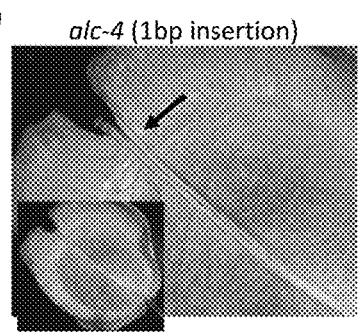
Figure 11D:
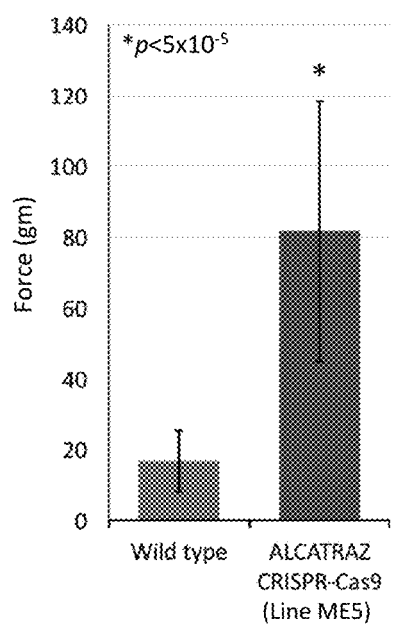
Figure 11E:
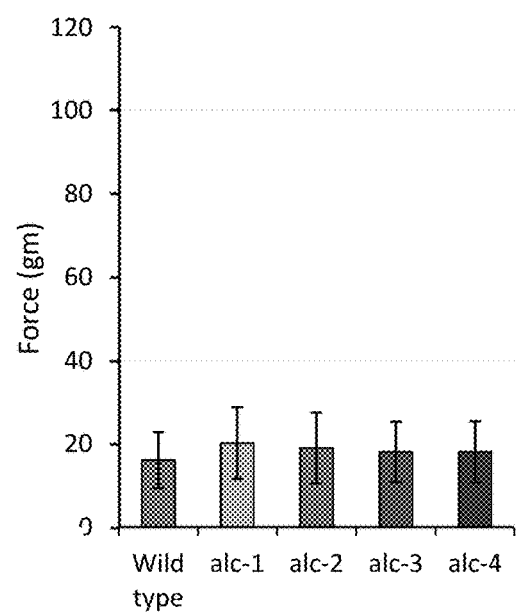

Pod shatter can drastically reduce yield, either from natural pod breakage in the field or due to losses during harvest (FIG. 10E). Several M2 lines showing reduced seedpod shatter were identified. The reanalysis of M3 progeny from two of these lines, MN A7-129 and MN A7-236, is shown in FIGS. 10F and 10G. The mutant pods required statistically significant greater force than wild type for breakage. Furthermore, these mutants exhibited reduced shattering under field conditions relative to wild type (FIGS. 10A-10C). WGS revealed the presence of a mutation in a putative *Arabidopsis* ortholog of SPATULA (SPT) in MN A7-129 (FIG. 9 and FIG. 10D). The mutation results in the substitution of tryptophan for a highly conserved arginine. Importantly in *Arabidopsis*, spt mutants exhibit increased pod shatter resistance.

These results demonstrate that a domesticated pennycress plant with reduced seedpod shatter can be designed by modifying the SPT gene.

Example 2: Generation and Characterization of Indehiscent (Ind; Also Referred to as Reduced Pod Shatter1-1 (rps1-1)) Line E42

Materials and Methods
Solutions:

| | | |
|---|---|---|
| A) | 0.2M sodium phosphate monobasic (NaH$_2$PO$_4$*H$_2$O) | 6.9 g/250 mL |
| B) | 0.2M sodium phosphate dibasic (NaH$_2$PO$_4$ anhydrous) | 7.1 g/250 mL |
| | For 50 mL of 0.1M sodium phosphate buffer at pH 7: | |
| | 9.75 mL | A |
| | 15.25 mL | B |
| | 25.0 mL | dH$_2$O |
| | 0.2% EMS in buffer: | |
| | 20 mL 0.1M Sodium Phosphate Buffer, pH 7 | |
| | 40 µL EMS liquid (Sigma #M0880-5G) | |
| | 0.1M sodium thiosulfate at pH 7.3: | |
| | 12.4 g sodium thiosulfate in 500 mL | |

Primary Seed Surface Sterilization

Wild-type pennycress (*Thlaspi arvense*) seeds (Spring 32 ecotype) were surface sterilized for 10 minutes in a 30% bleach, 0.05% SDS solution before being rinsed 3× with sterile water. Sterilized seeds were immediately subjected to EMS treatment.

Ethyl Methane Sulfonate (EMS) Treatment of Pennycress Seeds

Sterilized pennycress seeds (41 g) were agitated in distilled water overnight. Four 250 mL Erlenmeyer flasks with 10 g seed each, and 1 g in a separate small flask as a control, were agitated. The water was decanted.

25 MIA of 0.2% EMS in 0.1M sodium phosphate buffer (pH 7) was added. The control received only phosphate buffer with no EMS. The flasks were shaken in fume hood for 18 hours. The EMS solution was decanted off into an EMS waste bottle.

To rinse the seeds, 25 mLs of dH2O was added to each flask, and the flasks were shaken for 20 minutes. The rinse water was decanted into the EMS waste bottle.

To deactivate the EMS, seeds were washed for 20 minutes in 0.1M sodium thiosulfate (pH 7.3). The sodium thiosulfate solution was decanted into the EMS waste bottle.

The seeds were rinsed 4 times with dH2O for 15 minutes.

The seeds were suspended in 0.1% agarose, and germinated directly in autoclaved Reddiearth soil at a density of approximately 10 seeds per 4-inch pot.

Plant Growth Conditions

EMS-treated pennycress seeds were germinated and grown in an environmental growth chamber at 21° C., 16:8 6400K fluorescent light/dark, 50% humidity. Approximately 14 days after planting, plants were thinned and transplanted to a density of 4 plants per 4-inch pot. These $M_1$-generation plants showed telltale chlorotic leaf sectors that are indicative of a successful mutagenesis.

After dry down, these $M_1$-generation plants were catalogued and harvested. The M2-generation seeds were surface sterilized, planted and grown according to the protocols previously described.

Results

Identification and Characterization of RPS1-1 Mutant Line E42

Figures 13E, 13F:
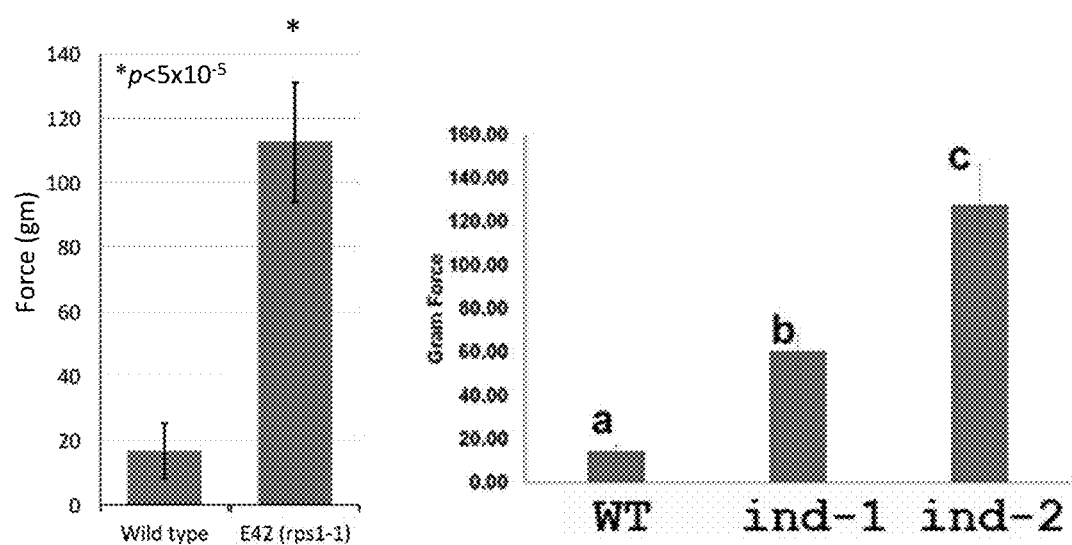

Putative reduced seedpod shatter mutants in the M2-generation were identified as those requiring relatively more force to rupture the pods compared to wild type when harvesting with a closed hand. Seeds (M3-generation) from putative M2-generation mutants were planted and grown in potting soil-containing 4-inch pots in a growth chamber and the pod shatter phenotype re-assessed upon plant senescence. Siblings from only one line (line E42, herein named reduced pod shatter1-1 or rps1-1; also herein named ind-3) reproduced an obvious reduced seedpod shatter phenotype (FIG. 13). That phenotype was also observed in overwintered field-grown $F_2$-generation plants arising from the following crosses: rps1-1×wild-type Elizabeth; rps1-1× wild-type MN106.

Figure 16:
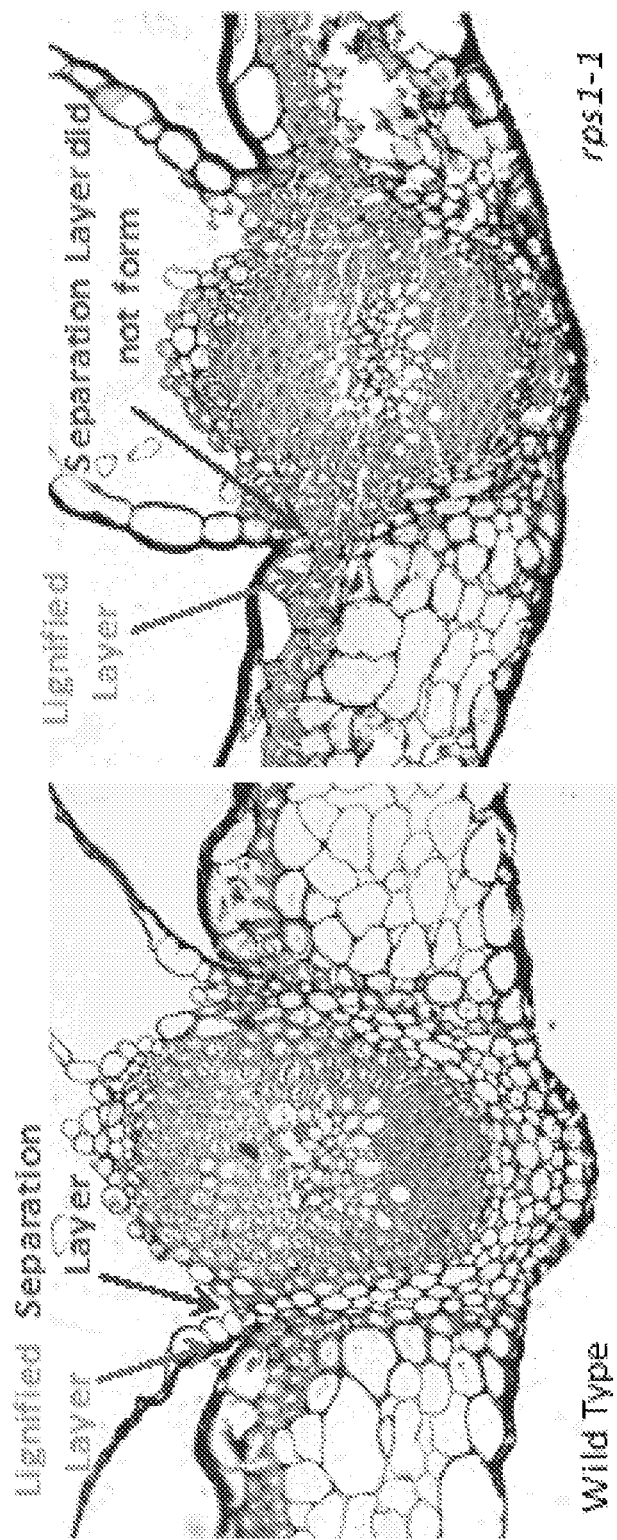
FIG. 16 contains microscopic images of toluidine blue-stained cross sections of a wild-type seedpod (left panel) and a seedpod from a pennycress plant having a modified IND gene (line ind-3 (rps1-1) right panel)) showing that the separation layer of cells did not form in the rps1-1 pod dehiscence zone.
Figures 18A, 18B:
FIGS. 18A-18C show an analysis of seedpod shatter in pennycress plants. A) An image showing field grown mature pods for a wild type pennycress plant. B) An image showing field grown mature pods for a representative mutant pennycress plant having a modified PID gene (line pid-1). The pennycress plant having a modified PID gene shows few shattered pods as highlighted by arrows in the wild type image. C) Greater force is required to break open the seedpods from a mutant pennycress plant having a modified PID gene (line pid-1). Bars represent standard deviations. Letters that are different represent significant differences based on ANOVA.
Figure 18C:
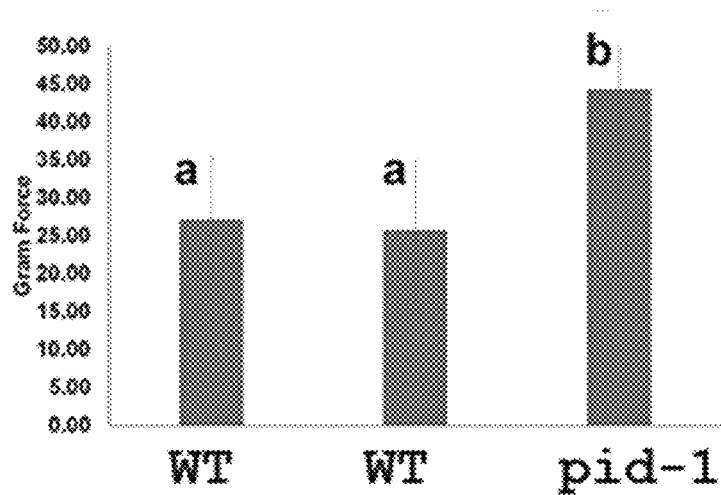
Figure 20:
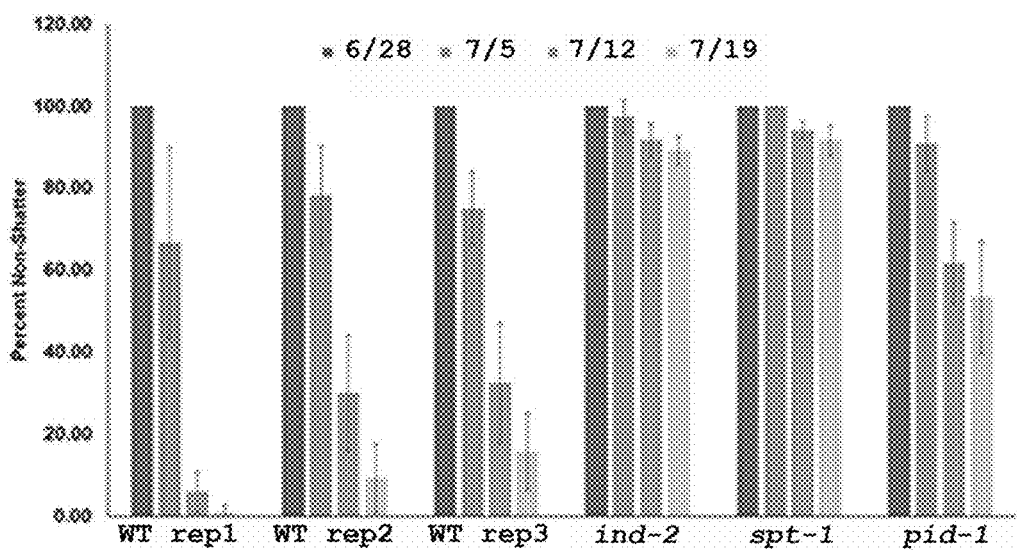
FIG. 20 is a graph showing the percent of non-shattered pods on plants over time. The percent of pods remaining on plants was measured at one-week intervals after pod maturation. All three reps of wild type showed nearly a 100% loss after three weeks whereas ind-2, spt-1, and pid-1 lines retained 60-90% of their seedpods during the same timeframe. All mutant phenotypes at the later time points are significantly different from wild type based on an ANOVA statistical analysis. Bars represent standard deviations.

The growth of rps1-1 plants was indistinguishable from that of wild-type plants (FIG. 13). When pulling the senesced seedpods apart with fingers, rps1-1 pods did not break at the dehiscence zone like wild type, but instead tore within the valve. Microscopic examination of the seedpod dehiscence zone showed that wild type pods often-times were slightly breaking apart, which was a phenotype not observed in rps1-1 pods (FIG. 13). Microscopic examination of toluidine blue-stained sections of rps1-1 seedpods revealed the lignified layer and separation layer within the dehiscence zone were poorly formed or absent (FIG. 16).

Genetic crosses were also made between rps1-1 plants and wild-type Spring plants. Ft-generation plants exhibited wild-type pod shatter whereas $F_2$-generation plants segregated 3:1 wild-type to reduced seedpod shatter (61 plants out of 217 showed the pod shatter phenotype=28.1%). These results confirmed the rps1-1 mutation to be recessive and segregated in a Mendelian fashion.

Figure 14A:
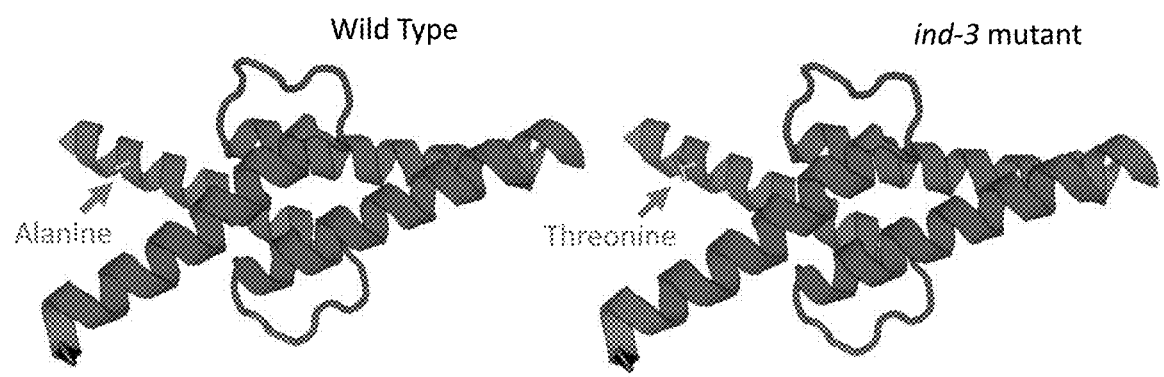
FIGS. 14A-14B show an exemplary mechanism for IND loss of function in seedpods from a mutant pennycress plant having a modified IND gene (line ind-3). A) Protein modeling of IND was performed using SWISS-MODEL (swiss-model.expasy.org/). B) The alanine to threonine amino acid substitution in ind-3 likely affects protein binding to the DNA. IND encodes a transcription factor that regulates expression of seedpod shatter-related genes.
Figure 14B:
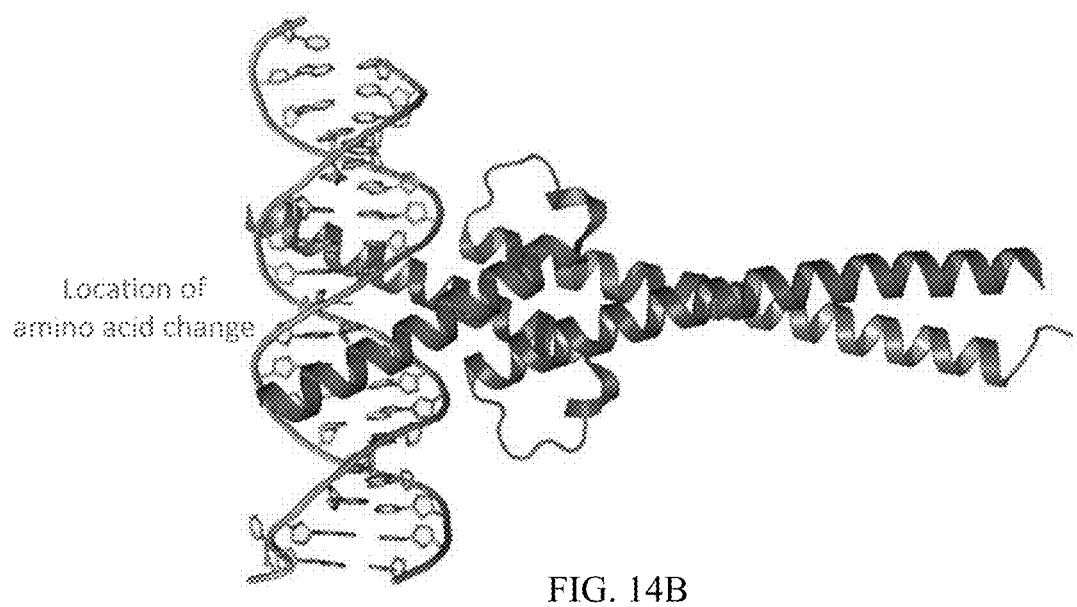

EMS mutagenesis typically introduces single-nucleotide transition mutations (e.g. G to A) into plant genomes. To identify the mutation in rps1-1 plants, DNA was extracted from rps1-1 and wild-type leaf tissue using either the CTAB protocol (below) or the Qiagen DNeasy Plant Mini Kit (product number 69106). PCR amplification of the INDEHISCENT (IND; also referred to as REDUCED SEEDPOD SHATTER (RPS)), SPATULA (SPT), ALCATRAZ (ALC), and REPLUMLESS (RPL) genes was performed and the resultant DNA sequenced. No mutations were initially identified in these genes. To resolve this, DNA from 42 $F_2$-generation×wild-type Spring 32 plants was extracted using the Qiagen DNeasy Plant Mini Kit and pooled. The pooled DNA was sequenced using a HiSeq 2500 sequencer. Detailed sequence analyses confirmed that a G to A transition mutation in the IND gene coding sequence co-segregated with the reduced seedpod shatter phenotype. This transition mutation at nucleotide residue 301 as set forth in SEQ ID NO:15 results in an alanine (A) to threonine (T) amino acid change at residue 101 in the amino acid sequence set forth in SEQ ID NO:16. The amino acid change resides in the DNA binding domain of the IND polypeptide (FIG. 14A, B) and likely disrupts binding of the IND transcription factor to promoters of seedpod shatter-related genes it regulates.

Example 3: Shatter Generation and Characterization of ALC Mutant Lines ME3, ME5, and ME6 by Direct Targeting of ALC with CRISPR-SaCas9

Materials and Methods
Construction of the Pennycress ALCATRAZ (ALC) Gene-Specific CRISPR-saCas9 Vector The constructs and cloning procedures for generation of *Thlaspi arvense* (pennycress) ALC-specific CRISPR-Sa-Cas9 constructs were as described elsewhere (see, e.g., Steinert et al., 2015, *Plant J.*, 84:1295-305; and Fauser et al., 2014, *Plant J.*, 79: 348-359).

The plant selectable marker (formerly NPT) was replaced with a hygromycin resistance (Hygromycin phosphotransferase (HPT)) gene in the pDe-SaCas9 binary vector.

Oligos were annealed to create a 20mer protospacer specific to the pennycress ALC sequence:

```
PennyALC_CRISPR-SaCAS9_FWD:
                             (SEQ ID NO: 53)
5' ATTGTGCGATTACCACCAACACAG 3'

PennyALC_CRISPR-SaCAS9_REV:
                             (SEQ ID NO: 54)
5' AAACCTGTGTTGGTGGTAATCGCA 3'
```

Vector Transformation into *Agrobacterium*

The pDe-SaCas9_Hyg vector containing the *Staphylococcus aureus* Cas9 (SaCas9) cassette with the pennycress ALC sequence-specific protospacer was transformed into *Agrobacterium tumefaciens* strain GV3101 using the freeze/thaw method described elsewhere (see, e.g., indiana.edu/~pikweb/Protocols%20page.html) The transformation product was plated on 1% agar Luria Broth (LB) plates with gentamycin (50 µg/ml) rifampicin (50 µg/ml) and spectinomycin (75 µg/ml). Single colonies were selected after two days of growth at 28° C.

Plant Transformation—Pennycress Floral Dip

Day One:
5 mL of LB+5 uL with appropriate antibiotics (Rifampin (50), Spectinomycin (75), and/or Gentamycin (50)) were inoculated with *Agrobacterium*. The cultures were allowed to grow, with shaking, overnight at 28° C.

Day Two (Early Morning):
25 mL of Luria Broth+25 uL appropriate antibiotics (Rifampin (50), Spectinomycin (75), and/or Gentamycin (50)) were inoculated with the initial culture from day one. The cultures were allowed to grow, with shaking, overnight at 28° C.

Day Two (Late Afternoon):
250 mL of Luria Broth+250 uL appropriate antibiotic (Rifampin (50), Spectinomycin (75), and/or Gentamycin (50)) were inoculated with 25 mL culture. The cultures were allowed to grow, with shaking, overnight at 28° C.

Day Three:
When the culture had grown to an $OD_{600}$ of ~1 (or looks thick and silky), the culture was decanted into large centrifuge tubes (all evenly weighted with analytical balance), and spun at 3,500 RPM at room temperature for 10 minutes to pellet cells. The supernatant was decanted off. The pelleted cells were resuspended in a solution of 5% sucrose and 0.02% Silwet L-77. The suspension was poured into clean beakers and placed in a vacuum chamber.

Newly flowering inflorescences of pennycress were fully submerged into the beakers, and subjected to a pressure of 30 PSI for 10 minutes.

After racemes of pennycress plants (Spring32 variety; these plants were 5 generations removed from seeds) were dipped, they were covered loosely with Saran wrap to maintain humidity and kept in the dark overnight before being uncovered and placed back in the environmental growth chamber.

Screening Transgenic Plants and Growth Condition

Pennycress seeds were surface sterilized by first rinsing in 70% ethanol then incubating 10 minutes in a 30% bleach, 0.05% SDS solution before being rinsed two times with sterile water and plated on selective plates (0.8% agar/one half-strength Murashige and Skoog salts with hygromycin B selection at 40 U ml$^{-1}$. Plates were wrapped in parafilm and kept in an environmental growth chamber at 21° C., 16:8 day/night for 8 days until hygromycin selection was apparent.

Surviving hygromycin-resistant T1-generation seedlings were transplanted into autoclaved Reddiearth soil mix and grown in an environmental growth chamber set to 16 hour days/8 hour nights at 21° C. and 50% humidity. T2-generation seeds were planted, and ~1.5 mg of leaf tissue from each T2-generation plant was harvested with a 3 mm hole punch, then processed using the Thermo Scientific™ Phire™ Plant Direct PCR Kit (Catalog # F130WH) as per manufacturer's instructions. PCR (20 µl volume) was performed on samples from six plants whose pods putatively required more hand force than wild type to shatter upon plant senescence. For the PCR, the following two primers were used, which amplified a 679 base pair fragment containing the protospacer location where the CRISPR-SaCas9 guide RNA and endonuclease had been targeted to bind and cut the genomic DNA:

```
ALCPCRF2:
                             (SEQ ID NO: 55)
AGGAGCTAAACATCGAAATTCGTTGAAGAG

ALCPCRR2:
                             (SEQ ID NO: 56)
TGTCGCAGATACTAGAGGAACATCACATCA
```

10 µl of the PCR product was digested with T7 Endonuclease I (Fisher Scientific catalog #M0302L) as per manufacturer's instructions then electrophoresed in a 1% agarose gel (FIG. 15). T7 endonuclease cleaves DNA that contains CRISPR-Cas9-induced DNA mismatches, in this case producing ~185 base pair fragment and a ~494 base pair fragment. The PCR products from all six plants were sequenced, and the three that gave positive results from the T7 endonuclease assay (lines ME3, ME5, and ME6) were found to have mutations in each chromosome pair in the locations expected for CRISPR-Cas9-induced mutations (e.g. at the protospacer adjacent to the NNGGGT PAM site where the guide was targeted to bind. Sequence chromatograms and descriptions of the mutations can be found in FIG. 15.

Example 4: Shatter Generation and Characterization of ADPG1 Mutant Lines by Direct Targeting of ADPG1 with CRISPR-SaCas9

Materials and Methods

The protocols used to generate ADPG1-specific CRISPR-SpCas9 constructs and to identify adpg1 mutations and mutant lines were the same as described in Example 4 above, except instead of using an SaCas9 vector, a modified SpCas9 vector as described in Fauser et al., 2014, *Plant J.*, 79: 348-359 was used. As with the pDe-SaCas9 binary vector, we replaced the plant selectable marker (formerly NPT) in the pDe-SpCas9 binary vector with a hygromycin resistance (Hygromycin phosphotransferase (HPT)) gene. The ADPG1-targeting gRNA protospacer sequence that was used in this vector (highlighted in bold and underlined in SEQ ID NO:29), which is adjacent to the NGG PAM site (underlined and italicized in SEQ ID NO:29), is as follows:

PennyADPG1_CRISPR-SpCAS9_FWD:
(SEQ ID NO: 57)
5' GATGGATATGGTCATGAAGA 3'

PennyADPG1_CRISPR-SpCAS9_REV:
(SEQ ID NO: 58)
5' TCTTCATGACCATATCCATC 3'

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pennycress plant comprising a loss-of-function modification in a gene sequence encoding a polypeptide involved in seedpod shatter; wherein said loss-of-function modification in said gene sequence comprises a guanine (G) to adenine (A) substitution at position 470 in the pinoid (PID) nucleic acid sequence set forth in SEQ ID NO:27 and encodes a modified PID polypeptide comprising the amino acid sequence set forth in SEQ ID NO:28,
   wherein seedpods of said pennycress plant require greater than about 20 grams of force to shatter.

2. The pennycress plant of claim 1, wherein said pennycress plant comprises seedpods that require about 20 grams to about 120 grams pulling force to shatter.

3. The pennycress plant of claim 1, wherein said pennycress plant comprises seedpods that are resistant to shatter under less than about 20 grams force.

4. A seed produced by the pennycress plant of claim 1, wherein the seed comprises the loss-of-function modification in the PID nucleic acid sequence and encodes the modified PID polypeptide.

* * * * *